United States Patent
Jeong et al.

(10) Patent No.: US 10,604,487 B2
(45) Date of Patent: Mar. 31, 2020

(54) PYRIDINOL DERIVATIVE OR PHARMACEUTICALLY ACCEPTABLE SALT THEREOF, AND PHARMACEUTICAL COMPOSITION CONTAINING SAME AS ACTIVE INGREDIENT

(71) Applicants: Research Cooperation Foundation of Yeungnam University, Gyeongsan-si (KR); Industry-University Cooperation Foundation Hanyang University Erica Campus, Ansan-si (KR)

(72) Inventors: Byeong-Seon Jeong, Daegu (KR); Jung-Ae Kim, Daegu (KR); Tae-gyu Nam, Suwon-si (KR)

(73) Assignees: Research Cooperation Foundation of Yeungnam University, Gyeongsan-si (KR); Industry-University Cooperation Foundation Hanyang University Erica Campus, Ansan-si (KR)

( * ) Notice: Subject to any disclaimer, the term of this patent is extended or adjusted under 35 U.S.C. 154(b) by 0 days.

(21) Appl. No.: 16/070,279

(22) PCT Filed: Jan. 13, 2017

(86) PCT No.: PCT/KR2017/000457
§ 371 (c)(1),
(2) Date: Jul. 15, 2018

(87) PCT Pub. No.: WO2017/123038
PCT Pub. Date: Jul. 20, 2017

(65) Prior Publication Data
US 2019/0010125 A1    Jan. 10, 2019

(30) Foreign Application Priority Data

Jan. 14, 2016  (KR) .................. 10-2016-0004871

(51) Int. Cl.
*C07D 213/75* (2006.01)
*C07D 213/69* (2006.01)
*C07D 213/76* (2006.01)

(52) U.S. Cl.
CPC ......... *C07D 213/75* (2013.01); *C07D 213/69* (2013.01); *C07D 213/76* (2013.01)

(58) Field of Classification Search
CPC ................................... C07D 213/75
USPC ..................................... 546/293
See application file for complete search history.

(56) References Cited

FOREIGN PATENT DOCUMENTS

| | | |
|---|---|---|
| KN | 10-2014-0049027 | 4/2014 |
| KR | 10-2008-0016649 | 2/2008 |
| KR | 10-2008-0069265 | 7/2008 |
| KR | 10-1103426 | 1/2012 |
| KR | 10-2013-0072166 | 7/2013 |
| KR | 10-12014-0125738 | 10/2014 |
| WO | 2005/121125 A1 * | 12/2005 |
| WO | WO 2017/123038 | 7/2017 |

OTHER PUBLICATIONS

King, Med. Chem: Principle and Practice (1994), pp. 206-208.*
International Search Report and the Written Opinion dated Apr. 18, 2017 From the International Searching Authority Re. Application No. PCT/KR2017/000457 and Its Translation of Search Report Into English. (12 Pages).

* cited by examiner

*Primary Examiner* — Taofiq A Solola

(57) ABSTRACT

The present invention relates to a pharmaceutical composition for preventing or treating inflammatory bowel disease, containing, as an active ingredient, a pyridinol derivative or a pharmaceutically acceptable salt thereof. A pyridinol derivative represented by chemical formula 1 or a pharmaceutically acceptable salt thereof has an excellent colitis inhibitory effect in an inflammatory bowel disease model, and thus can be useful as a medicine for preventing or treating inflammatory bowel disease.

10 Claims, No Drawings

PYRIDINOL DERIVATIVE OR PHARMACEUTICALLY ACCEPTABLE SALT THEREOF, AND PHARMACEUTICAL COMPOSITION CONTAINING SAME AS ACTIVE INGREDIENT

RELATED APPLICATIONS

This application is a National Phase of PCT Patent Application No. PCT/KR2017/000457 having International filing date of Jan. 13, 2017, which claims the benefit of priority of Korean Patent Application No. 10-2016-0004871 filed on Jan. 14, 2016. The contents of the above applications are all incorporated by reference as if fully set forth herein in their entirety.

FIELD AND BACKGROUND OF THE INVENTION

The present invention relates to a pyridinol derivative or pharmaceutically acceptable salt thereof, and a pharmaceutical composition for preventing or treating an inflammatory bowel disease containing the derivative or salt as an active ingredient.

An inflammatory bowel disease (IBD) is classified into two types of diseases such as ulcerative colitis and Crohn's disease, which are clinically similar, but different depending on histological opinions, and endoscopic and immunological aspects. It has been known that such IBD is mainly caused by the activation of inflammatory cells.

Continuous or improper activation in a bowel immune system plays a pivotal role for pathological physiology of chronic mucosal inflammation, and particularly, the infiltration of neutrophils, macrophages, lymphocytes and mast cells results in mucosal destruction and ulcers. Infiltrated and activated neutrophils are the critical cause of active oxygen nitrogen species, and such active species, as cytotoxic materials, induce cellular oxidative stress by a cross-linking protein, a lipid and a nucleic acid and result in epithelial dysfunction and damage.

When an inflammatory disease occurs, various inflammatory cytokines are secreted from the mucosa of the intestinal tract. TNF-α is highly expressed in the colonic lumen and colonic epithelial cells in patients with ulcerative colitis. According to a recent study, TNF-α has been known to play an important role in the pathogenesis of ulcerative colitis. An anti-TNF-α antibody, infliximab, has been known to be effective in treatment of Crohn's disease which had not been previously treated, as well as treatment of furuncles. However, these therapies are costly and, in some patients, cause side effects such as fluid reactions or infectious complications.

Monocyte chemoattractant protein-1 (MCP-1) is a 14-kDa member of the C—C chemokine family which mainly recruits and activates monocytes/macrophages in an inflammatory area. It has been reported that MCP-1 is localized and expressed in colonic epithelial cells and associated with monocyte infiltration in the mucosa of IBD patients. Unlike other chemokines, MCP-1 only binds to CCR2, and thus it has been known that the MCP-1/CCR2 binding is a key modulator for monocyte recruitment and plays an important role in IBD.

In addition, it has been known that, in the mucosa of an IBD patient, interleukin-8 (IL-8) significantly increases and promotes microvascular angiogenesis. As the inflammation becomes severe in the colon, IL-8 expression is increased, and therefore, it has been known that, in animal test models using rodents, an IL-8 specific antibody reduces bowel inflammation. Here, an intracellular Ca2+ change acts as a key factor in IL-8 induction.

As currently used IBD therapeutics, 5-aminosalicylic acid (5-ASA)-based drugs that interrupt the generation of prostaglandins, for example, sulfasalazine, have been used, or steroid immunosuppressants have been used.

Sulfasalazine is prone to side effects or adverse effects such as abdominal fullness, headaches, rashes, liver diseases, leukopenia, agranulocytosis, male infertility, etc. In addition, it is not sure whether sulfasalazine has a sufficient effect of inhibiting recurrence in patients with resected lesions or those with improvement.

Steroid immunosuppressants are adrenocortical steroids, which are recognized for short-term effects, but may not improve long-term prognosis. In addition, there are limitations that should only be used in acute cases in terms of side effects such as induced infectious diseases, secondary adrenal insufficiency, peptic ulcers, diabetes, psychiatric disorders, and steroidal kidney diseases.

In other words, since a reliable oral therapy for IBD has not been developed yet, there is a demand for development of an effective and low-cost oral therapeutic for such a disease.

PRIOR ART DOCUMENT

Patent Document

1. Korean Patent No. 1103426

SUMMARY OF THE INVENTION

Therefore, the inventors confirmed that a pyridinol derivative having a specific structure or pharmaceutically acceptable salt thereof has an excellent IBD therapeutic effect, and the present invention was completed based on this finding.

Accordingly, an object of the present invention is to provide a pharmaceutical composition which contains a pyridinol derivative or a pharmaceutically acceptable salt thereof as an active ingredient for the prevention or treatment of IBD.

To achieve the object, the present invention provides a compound represented by Formula 1 below or a pharmaceutically acceptable salt thereof.

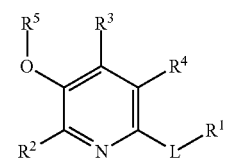

[Formula 1]

In Formula 1,

R2, R3 and R4 are each independently alkyl having 1 to 8 carbon atoms,

R5 is any one selected from the group consisting of hydrogen; halogen; alkyl having 1 to 8 carbon atoms; —Si(R6)3; and aryl having 6 to 18 carbon atoms, wherein the alkyl having 1 to 8 carbon atoms or aryl having 6 to 18 carbon atoms of R5 is each independently substituted with alkyl having 1 to 8 carbon atoms or aryl having 6 to 18 carbon atoms, or not substituted, R6 is any one selected from the group consisting of hydrogen, alkyl having 1 to 8 carbon atoms and aryl having 6 to 18 carbon atoms, R1 is any one selected from the group consisting of hydrogen; sulfonyl; carbonyl; alkyl having 1 to 12 carbon atoms; and aryl having 6 to 18 carbon atoms, wherein the sulfonyl or carbonyl of R1 is each independently substituted or not substituted with one or more substituents selected from the group consisting of alkyl having 1 to 8 carbon atoms, which is substituted or not substituted with a halogen; and aryl having 6 to 18 carbon atoms, which is substituted or not substituted with alkyl having 1 to 8 carbon atoms or halogen, and the alkyl having 1 to 12 carbon atoms or aryl having 6 to 18 carbon atoms of R1 is each independently substituted or not substituted with one or more selected from the group consisting of halogen; —NO2; alkyl having 1 to 8 carbon atoms, which is substituted or not substituted with halogen; alkoxy having 1 to 8 carbon atoms, which is substituted or not substituted with halogen; and aryl having 6 to 18 carbon atoms, which is substituted or not substituted with alkyl having 1 to 8 carbon atoms or halogen, L is —O— or a linker represented by Formula 2 or 3 below,

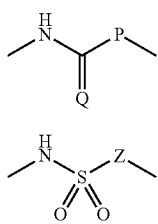

[Formula 2]

[Formula 3]

in Formula 2, Q is O or S, and P is —NH— or —O—, and in Formula 3, Z is a single bond or —NH—.

Since a pyridinol derivative or pharmaceutically acceptable salt thereof according to the present invention inhibits colitis in an IBD model, it can be effectively used as a drug for preventing or treating IBD.

DESCRIPTION OF SPECIFIC EMBODIMENTS OF THE INVENTION

Hereinafter, the configuration of the present invention will be described in detail.

The present invention provides a compound represented by Formula 1 below (hereinafter, a compound of Formula 1) or a pharmaceutically acceptable salt thereof.

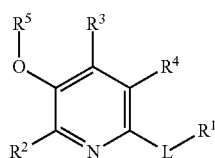

[Formula 1]

In Formula 1,

R2, R3 and R4 are each independently alkyl having 1 to 8 carbon atoms,

R5 is any one selected from the group consisting of hydrogen; halogen; alkyl having 1 to 8 carbon atoms; —Si(R6)3; and aryl having 6 to 18 carbon atoms, wherein the alkyl having 1 to 8 carbon atoms or aryl having 6 to 18 carbon atoms of R5 is each independently substituted with alkyl having 1 to 8 carbon atoms or aryl having 6 to 18 carbon atoms, or not substituted, and R6 is any one selected from the group consisting of hydrogen, alkyl having 1 to 8 carbon atoms; and aryl having 6 to 18 carbon atoms, R1 is any one selected from the group consisting of hydrogen; sulfonyl; carbonyl; alkyl having 1 to 12 carbon atoms; and aryl having 6 to 18 carbon atoms, wherein the sulfonyl or carbonyl of R1 is each independently substituted or not substituted with one or more substituents selected from the group consisting of alkyl having 1 to 8 carbon atoms, which is substituted or not substituted with a halogen; and aryl having 6 to 18 carbon atoms, which is substituted or not substituted with alkyl having 1 to 8 carbon atoms or halogen, and the alkyl having 1 to 12 carbon atoms or aryl having 6 to 18 carbon atoms of R1 is each independently substituted or not substituted with one or more selected from the group consisting of halogen; —NO2; alkyl having 1 to 8 carbon atoms, which is substituted or not substituted with halogen; alkoxy having 1 to 8 carbon atoms, which is substituted or not substituted with halogen; and aryl having 6 to 18 carbon atoms, which is substituted or not substituted with alkyl having 1 to 8 carbon atoms or halogen, L is —O— or a linker represented by Formula 2 or 3 below,

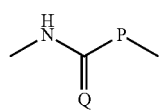

[Formula 2]

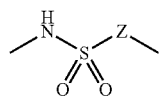

[Formula 3]

in Formula 2, Q is O or S, and P is —NH— or —O—, and in Formula 3, Z is a single bond or —NH—.

In the present invention, the compound of Formula 1 may be named a pyridinol derivative.

In addition, terms used to define a substituent of the compound of the present invention are as follows.

The "alkyl" refers to a linear, branched or cyclic saturated hydrocarbon, which has the stated number of carbon atoms unless specified otherwise.

The "halogen" means fluoro (F), chloro (Cl), bromo (Br) or iodo (I).

The "aryl" means, unless described otherwise, a monovalent or divalent aromatic group such as a 5- or 6-membered aromatic group.

In addition, in this formula, "Bn" refers to benzyl, "TBDPS" refers to tert-butyldiphenylsilyl, and Me refers to methyl.

The "pharmaceutical composition" refers to a mixture of a compound according to the present invention, physiologically/pharmaceutically acceptable salts thereof or prodrugs thereof, in addition to other chemical components such as physiologically/pharmaceutically acceptable vehicles and excipients. The purpose of a pharmaceutical composition is to facilitate administration of the compound to an organism.

The compound of Formula 1 may act as a prodrug. The "prodrug" refers to a material that is converted into a parent drug in a body. The prodrug is generally effective since it is easily administered, compared with a parent drug in some cases.

For example, although the parent drug is not bioavailable upon oral administration, the prodrug can be bioavailable upon oral administration. In addition, the prodrug may exhibit higher solubility than the parent drug in the pharmaceutical composition.

The "physiologically/pharmaceutically acceptable vehicle" refers to a vehicle or diluent that does not induce a significant stimulus to an organism, and does not eliminate biological activity and characteristics of the administered compound.

The "physiologically/pharmaceutically acceptable excipient" refers to a stable material added to facilitate the administration of a compound. As examples of the excipients, calcium carbonate, calcium phosphate, various types of sugar and starch, cellulose derivatives, gelatin, vegetable oil and polyethylene glycol may be used.

The "treat," "treating" and "treatment" refers to a method for reducing or eliminating a disease according to the present invention or symptoms concomitant therewith.

The "organism" includes all of living organisms that consist of at least one cell.

A living organism may be as simple as a eukaryotic single cell, or as complicated as a mammal such as a human.

The "therapeutically effective amount" refers to the amount of an administered compound that reduces one or more symptoms of a treated disease to a certain extent.

In one exemplary embodiment of the present invention, R2, R3 and R4 may be each independently alkyl having 1 to 4 carbon atoms, R5 may be any one selected from the group consisting of hydrogen; alkyl having 1 to 4 carbon atoms, which is substituted or not substituted with aryl having 6 to 12 carbon atoms; and —Si(R6)3, R6 may be alkyl having 1 to 6 carbon atoms or aryl having 6 to 12 carbon atoms, and L may be —O—, —NH—C(O)—NH—, —NH—C(S)—NH—, —NH—C(O)—O—, —NH—S(O)2-NH— or —NH—S(O)2-.

In addition, R2, R3 and R4 may be each independently methyl,

R5 may be any one selected from the group consisting of hydrogen; methyl substituted or not substituted with phenyl; and —Si(R6)3, and R6 may be butyl or phenyl.

In addition, in one exemplary embodiment, R1 may be any one selected from the group consisting of hydrogen; sulfonyl; carbonyl; alkyl having 1 to 10 carbon atoms; and aryl having 6 to 12 carbon atoms, wherein the sulfonyl or carbonyl may be each independently substituted or not substituted with one or more substituents selected from the group consisting of alkyl having 1 to 4 carbon atoms; and aryl having 6 to 12 carbon atoms, the alkyl having 1 to 10 carbon atoms may be substituted or not substituted with one or more substituents selected from the group consisting of halogen; alkoxy having 1 to 4 carbon atoms; and aryl having 6 to 12 carbon atoms, which is substituted or not substituted with alkyl having 1 to 6 carbon atoms or halogen, and the aryl having 6 to 12 carbon atoms may be substituted or not substituted with one or more substituents selected from the group consisting of halogen; —NO2; alkyl having 1 to 4 carbon atoms, which is substituted or not substituted with halogen; and alkoxy having 1 to 4 carbon atoms, which is substituted or not substituted with halogen.

Alternatively, R1 may be any one selected from the group consisting of hydrogen; sulfonyl; carbonyl; alkyl having 1 to 8 carbon atoms; and aryl having 6 to 10, wherein the sulfonyl or carbonyl may be substituted with phenyl, the alkyl having 1 to 8 carbon atoms may be substituted or not substituted with one or more substituents selected from the group consisting of halogen; methoxy; ethoxy; propoxy; and phenyl substituted or not substituted with alkyl having 1 to 4 carbon atoms or halogen, and the aryl having 6 to 10 carbon atoms may be substituted or not substituted with one or more substituents selected from the group consisting of halogen; —NO2; alkyl having 1 to 4 carbon atoms, which is substituted or not substituted with halogen; and alkoxy having 1 to 4 carbon atoms, which is substituted or not substituted with halogen.

In addition, in one exemplary embodiment, R2, R3 and R4 may be each independently methyl, R5 may be hydrogen; methyl substituted or not substituted with phenyl; or a silyl substituted with phenyl and butyl, and R1 may be hydrogen; carbonyl substituted with phenyl; sulfonyl substituted with phenyl; alkyl having 1 to 8 carbon atoms, which is substituted or not substituted with one or more substituents selected from the group consisting of chloro, methoxy, phenyl, chlorophenyl and butylphenyl; phenyl or naphthyl substituted or not substituted with one or more substituents selected from the group consisting of chloro, fluoro, bromo, methyl, ethyl, propyl, butyl, trifluoromethyl, nitro, methoxy and trifluoromethoxy.

More specifically, the compound according to the present invention may be any one selected from the group consisting of compounds represented by the following formulas.

Pyridinol-urea derivatives may be represented by the following formulas.

TABLE 1

| Example | Structure | Name |
|---|---|---|
| 15-1 | 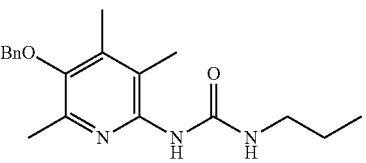 [SMILES: CCCNC(=O)Nc1nc(C)c(OCc2ccccc2)c(C)c1C] | (1-(5-Benzyloxy-3,4,6-trimethylpyridin-2-yl)-3-propylurea) |

TABLE 1-continued

| Example | Structure | Name |
|---------|-----------|------|
| 16-1 | 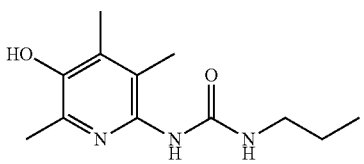 [SMILES: CCCNC(=O)Nc1nc(C)c(O)c(C)c1C] | (1-(5-Hydroxy-3,4,6-trimethylpyridin-2-yl)-3-propylurea) |
| 15-2 | 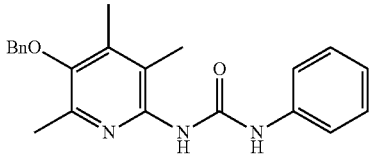 | (1-(5-Benzyloxy-3,4,6-trimethylpyridin-2-yl)-3-phenylurea) |
| 16-2 | 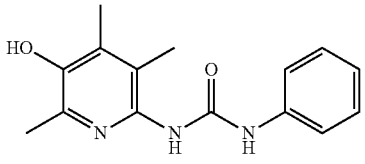 [SMILES: Cc1nc(NC(=O)Nc2ccccc2)c(C)c(C)c1O] | (1-(5-Hydroxy-3,4,6-trimethylpyridin-2-yl)-3-phenylurea) |
| 15-3 | 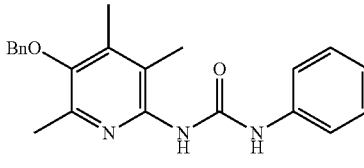 | (1-(5-Benzyloxy-3,4,6-trimethylpyridin-2-yl)-3-(4-chlorophenyl)urea) |
| 16-3 | 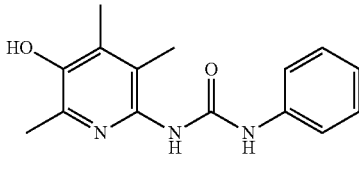 | (1-(4-Chlorophenyl)-3-(5-hydroxy-3,4,6-trimethylpyridin-2-yl)urea) |
| 15-4 | 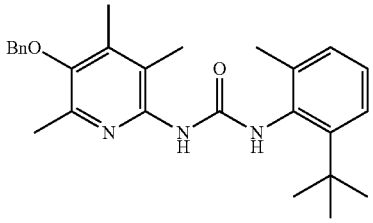 [SMILES: Cc1cccc(C(C)(C)C)c1NC(=O)Nc1nc(C)c(OCc2ccccc2)c(C)c1C] | (1-(5-Benzyloxy-3,4,6-trimethylpyridin-2-yl)-3-(2-tert-butyl-6-methylphenyl)urea) |
| 16-4 | 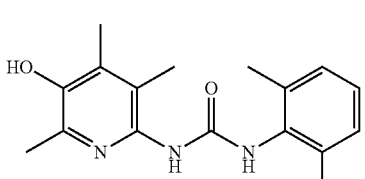 | (1-(2-tert-butyl-6-methylphenyl)-3-(5-hydroxy-3,4,6-trimethylpyridin-2-yl)urea) |
| 15-5 | 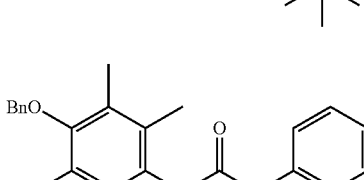 | (1-(5-Benzyloxy-3,4,6-trimethylpyridin-2-yl)-3-(naphthalen-1-yl)urea) |

TABLE 1-continued

| Example | Structure | Name |
|---|---|---|
| 16-5 | 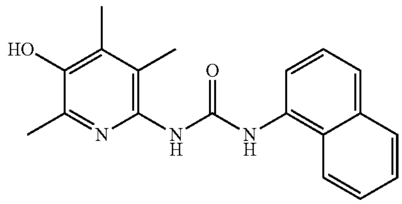 [SMILES: Cc1nc(NC(=O)Nc2cccc3ccccc23)c(C)c(C)c1O] | (1-(5-Hydroxy-3,4,6-trimethylpyridin-2-yl)-3-(naphthalen-1-yl)urea) |
| 15-6 | 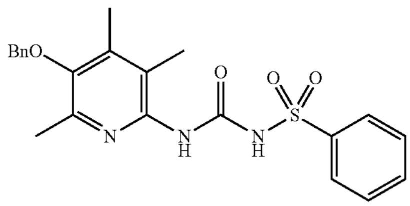 [SMILES: Cc1nc(NC(=O)NS(=O)(=O)c2ccccc2)c(C)c(C)c1OCc1ccccc1] | (N-((5-Benzyloxy-3,4,6-trimethylpyridin-2-yl)carbamoyl)benzenesulfonamide) |
| 16-6 | 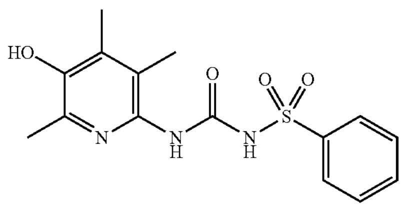 [SMILES: Cc1nc(NC(=O)NS(=O)(=O)c2ccccc2)c(C)c(C)c1O] | (N-((5-Hydroxy-3,4,6-trimethylpyridin-2-yl)carbamoyl)benzenesulfonamide) |
| 15-7 | 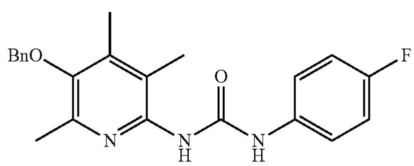 [SMILES: Cc1nc(NC(=O)Nc2ccc(F)cc2)c(C)c(C)c1OCc1ccccc1] | (1-(5-Benzyloxy-3,4,6-trimethylpyridin-2-yl)-3-(4-fluorophenyl)urea) |
| 16-7 | 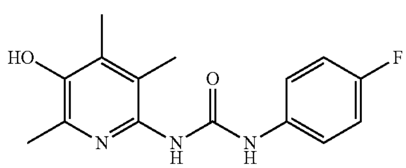 [SMILES: Cc1nc(NC(=O)Nc2ccc(F)cc2)c(C)c(C)c1O] | (1-(4-Fluorophenyl)-3-(5-hydroxy-3,4,6-trimethylpyridin-2-yl)urea) |
| 15-8 | 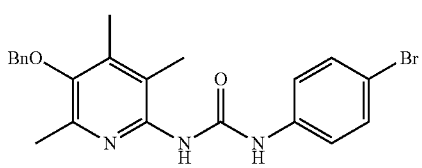 [SMILES: Cc1nc(NC(=O)Nc2ccc(Br)cc2)c(C)c(C)c1OCc1ccccc1] | (1-(5-Benzyloxy-3,4,6-trimethylpyridin-2-yl)-3-(4-bromophenyl)urea) |
| 16-8 | 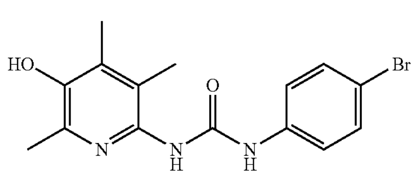 [SMILES: Cc1nc(NC(=O)Nc2ccc(Br)cc2)c(C)c(C)c1O] | (1-(4-Bromophenyl)-3-(5-hydroxy-3,4,6-trimethylpyridin-2-yl)urea) |
| 15-9 | 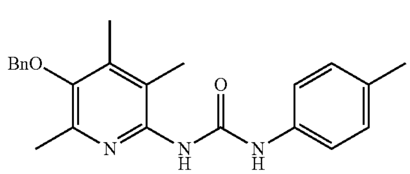 | (1-(5-Benzyloxy-3,4,6-trimethylpyridin-2-yl)-3-(p-tolyl)urea) |

TABLE 1-continued

| Example | Structure | Name |
|---|---|---|
| 16-9 | 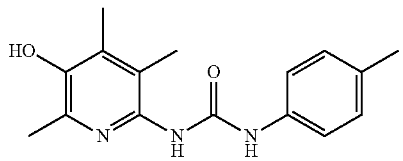 | (1-(5-Hydroxy-3,4,6-trimethylpyridin-2-yl)-3-(p-tolyl)urea) |
| 15-10 | 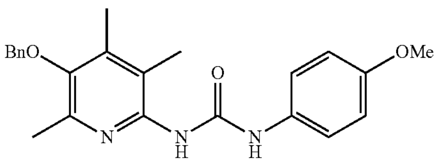 [SMILES: COc1ccc(NC(=O)Nc2nc(C)c(OCc3ccccc3)c(C)c2C)cc1] | (1-(5-Benzyloxy-3,4,6-trimethylpyridin-2-yl)-3-(4-methoxyphenyl)urea) |
| 16-10 | 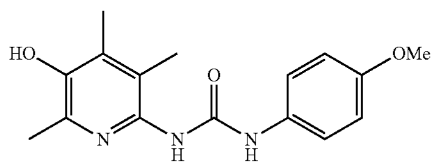 | (1-(5-Hydroxy-3,4,6-trimethylpyridin-2-yl)-3-(4-methoxyphenyl)urea) |
| 15-11 | 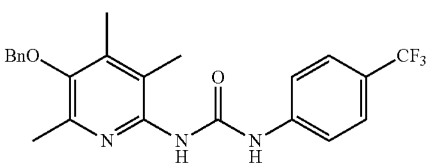 [SMILES: Cc1nc(NC(=O)Nc2ccc(C(F)(F)F)cc2)c(C)c(C)c1OCc1ccccc1] | (1-(5-Benzyloxy-3,4,6-trimethylpyridin-2-yl)-3-(4-(trifluoromethyl)phenyl)urea) |
| 16-11 | 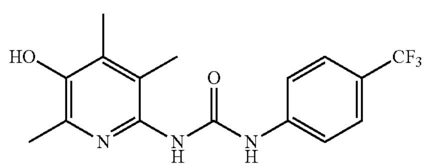 | (1-(5-Hydroxy-3,4,6-trimethylpyridin-2-yl)-3-(4-(trifluoromethyl)phenyl)urea) |
| 15-12 | 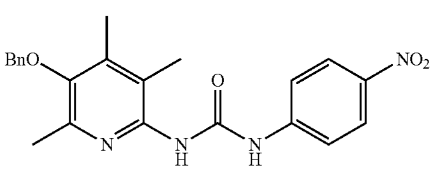 [SMILES: Cc1nc(NC(=O)Nc2ccc([N+](=O)[O-])cc2)c(C)c(C)c1OCc1ccccc1] | (1-(5-Benzyloxy-3,4,6-trimethylpyridin-2-yl)-3-(4-nitrophenyl)urea) |
| 16-12 | 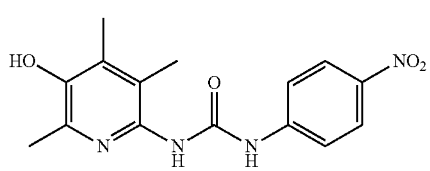 [SMILES: Cc1nc(NC(=O)Nc2ccc([N+](=O)[O-])cc2)c(C)c(C)c1O] | (1-(5-Hydroxy-3,4,6-trimethylpyridin-2-yl)-3-(4-nitrophenyl)urea) |
| 15-13 | 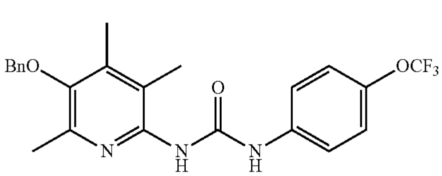 [SMILES: Cc1nc(NC(=O)Nc2ccc(OC(F)(F)F)cc2)c(C)c(C)c1OCc1ccccc1] | (1-(5-Benzyloxy-3,4,6-trimethylpyridin-2-yl)-3-(4-(trifluoromethoxy)phenyl)urea) |
| 16-13 | 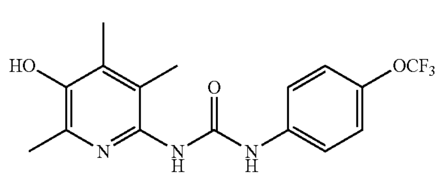 [SMILES: Cc1nc(NC(=O)Nc2ccc(OC(F)(F)F)cc2)c(C)c(C)c1O] | (1-(5-Hydroxy-3,4,6-trimethylpyridin-2-yl)-3-(4-(trifluoromethoxy)phenyl)urea) |

TABLE 1-continued

| Example | Structure | Name |
|---|---|---|
| 15-14 | 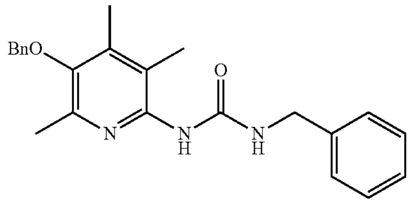 [SMILES: Cc1nc(NC(=O)NCc2ccccc2)c(C)c(C)c1OCc1ccccc1] | (1-Benzyl-3-(5-benzyloxy-3,4,6-trimethylpyridin-2-yl)urea) |
| 16-14 | 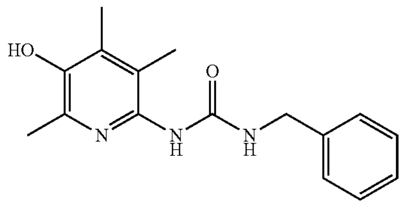 [SMILES: Cc1nc(NC(=O)NCc2ccccc2)c(C)c(C)c1O] | (1-Benzyl-3-(5-hydroxy-3,4,6-trimethylpyridin-2-yl)urea) |
| 15-15 | 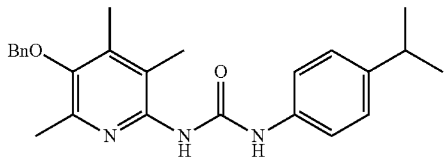 [SMILES: Cc1nc(NC(=O)Nc2ccc(C(C)C)cc2)c(C)c(C)c1OCc1ccccc1] | (1-(5-Benzyloxy-3,4,6-trimethylpyridin-2-yl)-3-(4-isopropylphenyl)urea) |
| 16-15 | 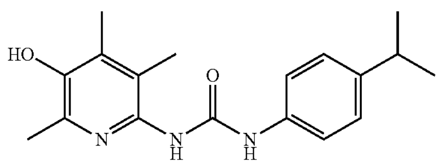 [SMILES: Cc1nc(NC(=O)Nc2ccc(C(C)C)cc2)c(C)c(C)c1O] | (1-(5-Hydroxy-3,4,6-trimethylpyridin-2-yl)-3-(4-isopropylphenyl)urea) |
| 15-16 | 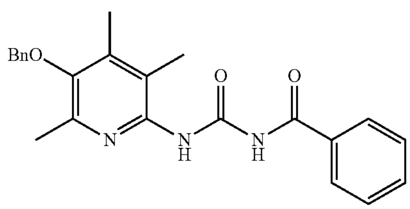 [SMILES: Cc1nc(NC(=O)NC(=O)c2ccccc2)c(C)c(C)c1OCc1ccccc1] | (N-((5-Benzyloxy-3,4,6-trimethylpyridin-2-yl)carbamoyl)benzamide) |
| 16-16 | 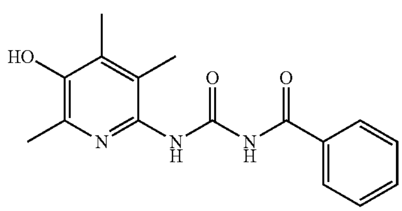 [SMILES: Cc1nc(NC(=O)NC(=O)c2ccccc2)c(C)c(C)c1O] | (N-((5-Hydroxy-3,4,6-trimethylpyridin-2-yl)carbamoyl)benzamide) |

Pyridinol-thiourea derivatives may be represented by the following formulas.

TABLE 2

| Example | Structure | Name |
|---|---|---|
| 17-1a | 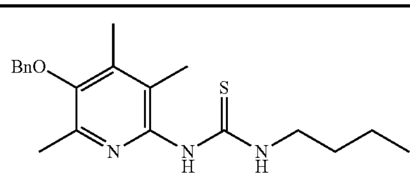 | (1-(5-Benzyloxy-3,4,6-trimethylpyridin-2-yl)-3-butylthiourea) |

TABLE 2-continued

| Example | Structure | Name |
|---------|-----------|------|
| 18-1 | 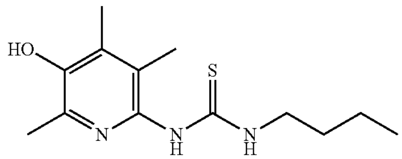 [SMILES: CCCCNC(=S)Nc1nc(C)c(O)c(C)c1C] | (1-Butyl-3-(5-hydroxy-3,4,6-trimethylpyridin-2-yl)thiourea) |
| 17-2a | 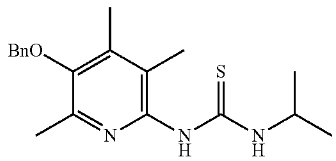 [SMILES: Cc1nc(NC(=S)NC(C)C)c(C)c(C)c1OCc1ccccc1] | (1-(5-Benzyloxy-3,4,6-trimethylpyridin-2-yl)-3-isopropylthiourea) |
| 18-2 | 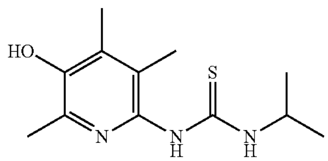 [SMILES: Cc1nc(NC(=S)NC(C)C)c(C)c(C)c1O] | (1-(5-Hydroxy-3,4,6-trimethylpyridin-2-yl)-3-isopropylthiourea) |
| 17-3a | 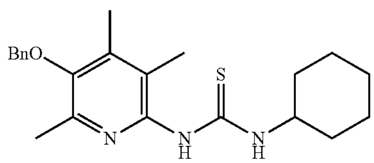 [SMILES: Cc1nc(NC(=S)NC2CCCCC2)c(C)c(C)c1OCc1ccccc1] | (1-(5-Benzyloxy-3,4,6-trimethylpyridin-2-yl)-3-cyclohexylthiourea) |
| 18-3 | 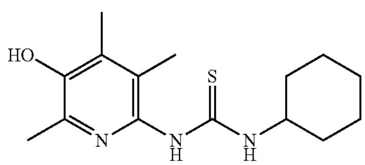 [SMILES: Cc1nc(NC(=S)NC2CCCCC2)c(C)c(C)c1O] | (1-Cyclohexyl-3-(5-hydroxy-3,4,6-trimethylpyridin-2-yl)thiourea) |
| 17-4a | 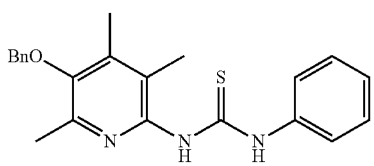 [SMILES: Cc1nc(NC(=S)Nc2ccccc2)c(C)c(C)c1OCc1ccccc1] | (1-(5-Benzyloxy-3,4,6-trimethylpyridin-2-yl)-3-phenylthiourea) |
| 18-4 | 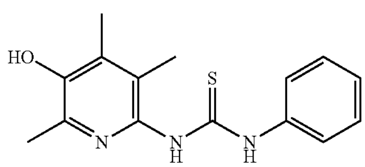 [SMILES: Cc1nc(NC(=S)Nc2ccccc2)c(C)c(C)c1O] | (1-(5-Hydroxy-3,4,6-trimethylpyridin-2-yl)-3-phenylthiourea) |
| 17-5c | 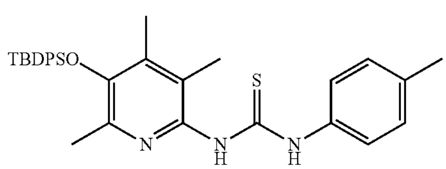 | (1-(5-((tert-butyldiphenylsilyl)oxy)-3,4,6-trimethylpyridin-2-yl)-3-(p-tolyl)thiourea) |
| 18-5 | 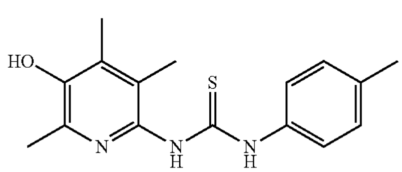 | (1-(5-Hydroxy-3,4,6-trimethylpyridin-2-yl)-3-(p-tolyl)thiourea) |

TABLE 2-continued

| Example | Structure | Name |
|---------|-----------|------|
| 17-6a | 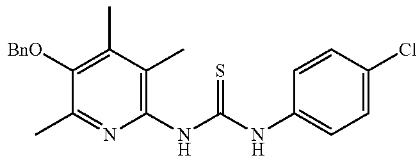 [SMILES: Cc1nc(NC(=S)Nc2ccc(Cl)cc2)c(C)c(C)c1OCc1ccccc1] | (1-(5-Benzyloxy-3,4,6-trimethylpyridin-2-yl)-3-(4-chlorophenyl)thiourea) |
| 18-6 | 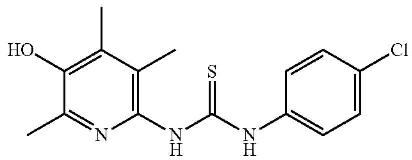 [SMILES: Cc1nc(NC(=S)Nc2ccc(Cl)cc2)c(C)c(C)c1O] | (1-(4-Chlorophenyl)-3-(5-hydroxy-3,4,6-trimethylpyridin-2-yl)thiourea) |
| 17-7c | 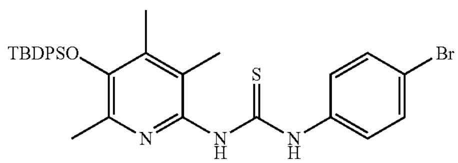 | (1-(4-Bromophenyl)-3-(5-((tert-butyldiphenylsilyl)oxy)-3,4,6-trimethylpyridin-2-yl)thiourea) |
| 18-7 | 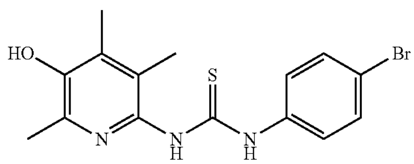 [SMILES: Cc1nc(NC(=S)Nc2ccc(Br)cc2)c(C)c(C)c1O] | (1-(4-Bromophenyl)-3-(5-hydroxy-3,4,6-trimethylpyridin-2-yl)thiourea) |
| 17-8a | 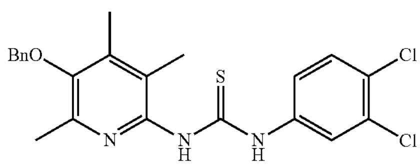 [SMILES: Cc1nc(NC(=S)Nc2ccc(Cl)c(Cl)c2)c(C)c(C)c1OCc1ccccc1] | (1-(5-Benzyloxy-3,4,6-trimethylpyridin-2-yl)-3-(3,4-dichlorophenyl)thiourea) |
| 17-8b | 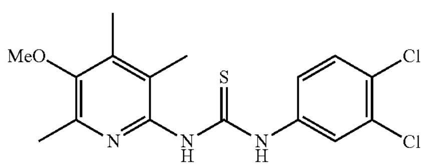 [SMILES: COc1c(C)nc(NC(=S)Nc2ccc(Cl)c(Cl)c2)c(C)c1C] | (1-(3,4-Dichlorophenyl)-3-(5-methoxy-3,4,6-trimethylpyridin-2-yl)thiourea) |
| 17-8c | 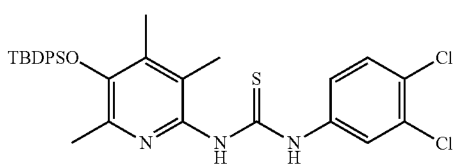 | (1-(5-((tert-Butyldiphenylsilyl)oxy)-3,4,6-trimethylpyridin-2-yl)-3-(3,4-dichlorophenyl)thiourea) |
| 18-8 | 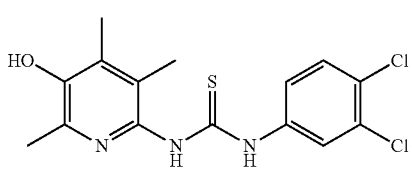 [SMILES: Cc1nc(NC(=S)Nc2ccc(Cl)c(Cl)c2)c(C)c(C)c1O] | (1-(3,4-Dichlorophenyl)-3-(5-hydroxy-3,4,6-trimethylpyridin-2-yl)thiourea) |
| 17-9a | 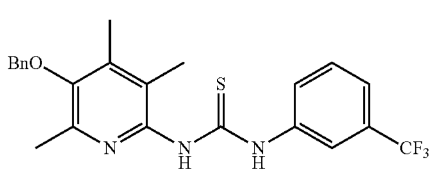 [SMILES: Cc1nc(NC(=S)Nc2cccc(C(F)(F)F)c2)c(C)c(C)c1OCc1ccccc1] | (1-(5-Benzyloxy-3,4,6-trimethylpyridin-2-yl)-3-(3-(trifluoromethyl)phenyl)thiourea) |

TABLE 2-continued

| Example | Structure | Name |
|---|---|---|
| 17-9b | [structure] | (1-(5-Methoxy-3,4,6-trimethylpyridin-2-yl)-3-(3-(trifluoromethyl)phenyl)thiourea) |
| 17-9c | [structure] | (1-(5-((tert-Butyldiphenylsilyl)oxy)-3,4,6-trimethylpyridin-2-yl)-3-(3-(trifluoromethyl)phenyl)thiourea) |
| 18-9 | [structure] | (1-(5-Hydroxy-3,4,6-trimethylpyridin-2-yl)-3-(3-(trifluoromethyl)phenyl)thiourea) |
| 17-10c | [structure] | (1-(5-((tert-Butyldiphenylsilyl)oxy)-3,4,6-trimethylpyridin-2-yl)-3-(4-(trifluoromethyl)phenyl)thiourea) |
| 18-10 | [structure] | (1-(5-Hydroxy-3,4,6-trimethylpyridin-2-yl)-3-(4-(trifluoromethyl)phenyl)thiourea) |
| 17-11c | [structure] | (1-(5-((tert-Butyldiphenylsilyl)oxy)-3,4,6-trimethylpyridin-2-yl)-3-(4-nitrophenyl)thiourea) |
| 18-11 | [structure] | (1-(5-Hydroxy-3,4,6-trimethylpyridin-2-yl)-3-(4-nitrophenyl)thiourea) |
| 17-12c | [structure] | (1-(5-((tert-Butyldiphenylsilyl)oxy)-3,4,6-trimethylpyridin-2-yl)-3-(4-methoxyphenyl)thiourea) |
| 18-12 | [structure] | (1-(5-Hydroxy-3,4,6-trimethylpyridin-2-yl)-3-(4-methoxyphenyl)thiourea) |

TABLE 2-continued

| Example | Structure | Name |
|---|---|---|
| 17-13a | 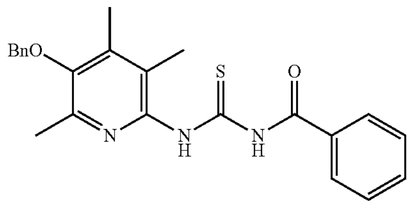 [SMILES: Cc1nc(NC(=S)NC(=O)c2ccccc2)c(C)c(C)c1OCc1ccccc1] | (N-((5-Benzyloxy-3,4,6-trimethylpyridin-2-yl)carbamothioyl)benzamide) |
| 18-13 | 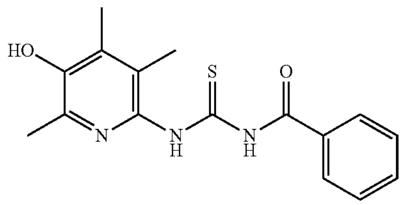 [SMILES: Cc1nc(NC(=S)NC(=O)c2ccccc2)c(C)c(C)c1O] | (N-((5-Hydroxy-3,4,6-trimethylpyridin-2-yl)carbamothioyl)benzamide) |

Pyridinol-carbamate derivatives may be represented by the following formulas.

TABLE 3

| Example | Structure | Name |
|---|---|---|
| 19-1 | 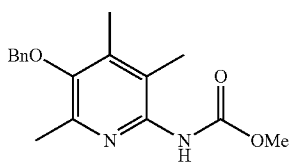 [SMILES: COC(=O)Nc1nc(C)c(OCc2ccccc2)c(C)c1C] | (Methyl (5-benzyloxy-3,4,6-trimethylpyridin-2-yl)carbamate) |
| 20-1 | 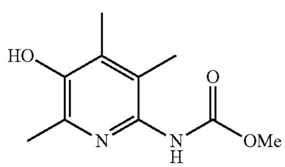 | (Methyl (5-hydroxy-3,4,6-trimethylpyridin-2-yl)carbamate) |
| 19-2 | 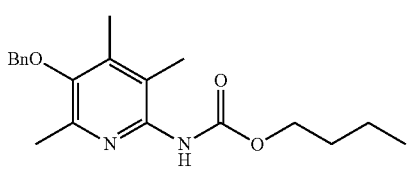 [SMILES: CCCCOC(=O)Nc1nc(C)c(OCc2ccccc2)c(C)c1C] | (Butyl (5-benzyloxy-3,4,6-trimethylpyridin-2-yl)carbamate) |
| 20-2 | 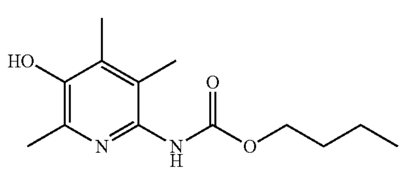 [SMILES: CCCCOC(=O)Nc1nc(C)c(O)c(C)c1C] | (Butyl (5-hydroxy-3,4,6-trimethylpyridin-2-yl)carbamate) |
| 19-3 | 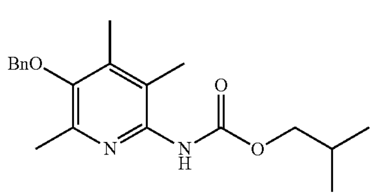 [SMILES: Cc1nc(NC(=O)OCC(C)C)c(C)c(C)c1OCc1ccccc1] | (Isobutyl (5-benzyloxy-3,4,6-trimethylpyridin-2-yl)carbamate) |

TABLE 3-continued

| Example | Structure | Name |
|---|---|---|
| 20-3 | 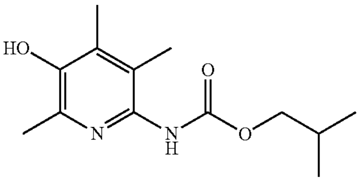 [SMILES: Cc1nc(NC(=O)OCC(C)C)c(C)c(C)c1O] | (Isobutyl (5-hydroxy-3,4,6-trimethylpyridin-2-yl)carbamate) |
| 19-4 | 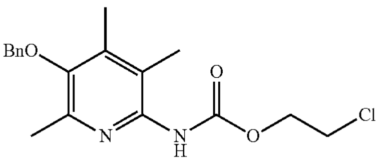 [SMILES: Cc1nc(NC(=O)OCCCl)c(C)c(C)c1OCc1ccccc1] | (2-Chloroethyl (5-benzyloxy-3,4,6-trimethylpyridin-2-yl)carbamate) |
| 20-4 | 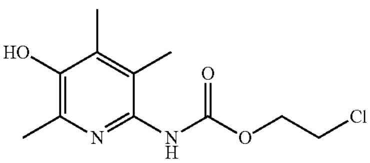 [SMILES: Cc1nc(NC(=O)OCCCl)c(C)c(C)c1O] | (2-Chloroethyl (5-hydroxy-3,4,6-trimethylpyridin-2-yl)carbamate) |
| 19-5 | 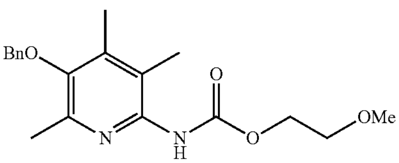 [SMILES: COCCOC(=O)Nc1nc(C)c(OCc2ccccc2)c(C)c1C] | (2-Methoxyethyl (5-benzyloxy-3,4,6-trimethylpyridin-2-yl)carbamate) |
| 20-5 | 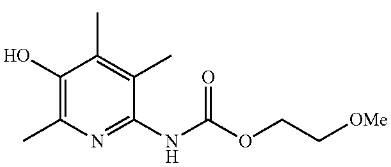 [SMILES: COCCOC(=O)Nc1nc(C)c(O)c(C)c1C] | (2-Methoxyethyl (5-hydroxy-3,4,6-trimethylpyridin-2-yl)carbamate) |

Pyridinol-sulfonamide derivatives may be represented by the following formulas.

TABLE 4

| Example | Structure | Name |
|---|---|---|
| 21-1 | 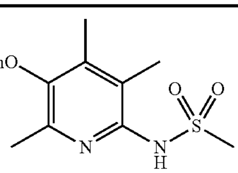 | (N-(5-Benzyloxy-3,4,6-trimethylpyridin-2-yl)methanesulfonamide) |
| 22-1 | 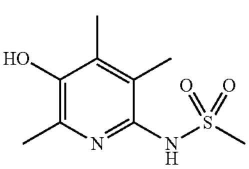 | (N-(5-Hydroxy-3,4,6-trimethylpyridin-2-yl)methanesulfonamide) |
| 21-2 | 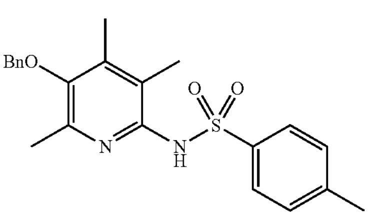 | (N-(5-Benzyloxy-3,4,6-trimethylpyridin-2-yl)-4-methylbenzenesulfonamide) |

TABLE 4-continued

| Example | Structure | Name |
|---|---|---|
| 22-2 | 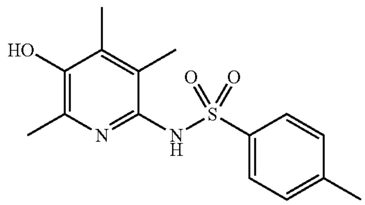 | (N-(5-Hydroxy-3,4,6-trimethylpyridin-2-yl)-4-methylbenzenesulfonamide) |
| 21-3 | 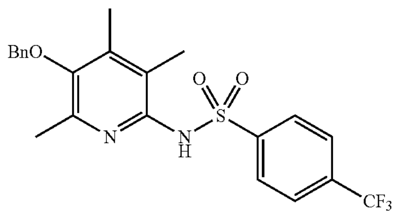 [SMILES: Cc1nc(NS(=O)(=O)c2ccc(C(F)(F)F)cc2)c(C)c(C)c1OCc1ccccc1] | (N-(5-Benzyloxy-3,4,6-trimethylpyridin-2-yl)-4-(trifluoromethyl)benzenesulfonamide) |
| 22-3 | 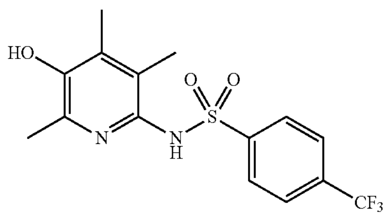 [SMILES: Cc1nc(NS(=O)(=O)c2ccc(C(F)(F)F)cc2)c(C)c(C)c1O] | (N-(5-Hydroxy-3,4,6-trimethylpyridin-2-yl)-4-(trifluoromethyl)benzenesulfonamide) |
| 21-4 | 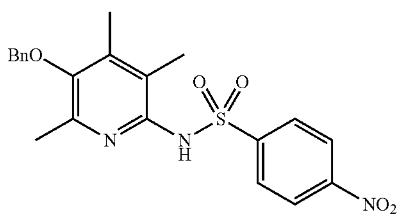 [SMILES: Cc1nc(NS(=O)(=O)c2ccc([N+](=O)[O-])cc2)c(C)c(C)c1OCc1ccccc1] | (N-(5-Benzyloxy-3,4,6-trimethylpyridin-2-yl)-4-nitrobenzenesulfonamide) |
| 22-4 | 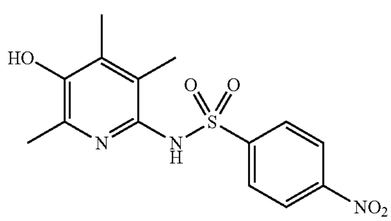 | (N-(5-Hydroxy-3,4,6-trimethylpyridin-2-yl)-4-nitrobenzenesulfonamide) |
| 21-5 | 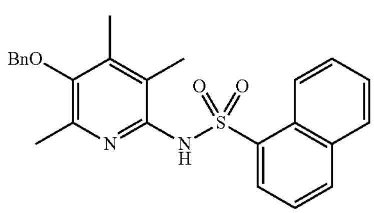 [SMILES: Cc1nc(NS(=O)(=O)c2cccc3ccccc23)c(C)c(C)c1OCc1ccccc1] | (N-(5-Benzyloxy-3,4,6-trimethylpyridin-2-yl)naphthalene-1-sulfonamide) |
| 22-5 | 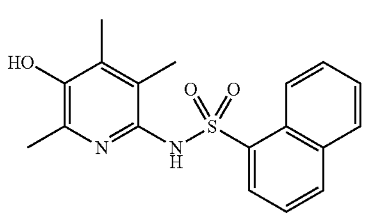 [SMILES: Cc1nc(NS(=O)(=O)c2cccc3ccccc23)c(C)c(C)c1O] | (N-(5-Hydroxy-3,4,6-trimethylpyridin-2-yl)naphthalene-1-sulfonamide) |

Pyridinol-sulfamide derivatives may be represented by the following formulas.

TABLE 5

| Example | Structure | Name |
|---|---|---|
| 24-1 | 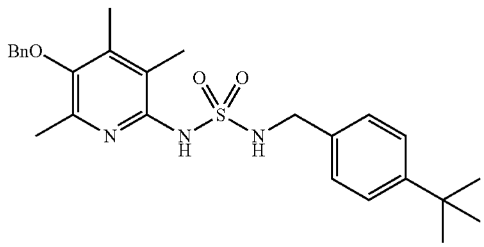 [SMILES: Cc1nc(NS(=O)(=O)NCc2ccc(C(C)(C)C)cc2)c(C)c(C)c1OCc1ccccc1] | (N-(5-Benzyloxy-3,4,6-trimethyl-2-pyridinyl)-N'-(4-(tert-butyl)benzyl)sulfamide) |
| 25-1 | 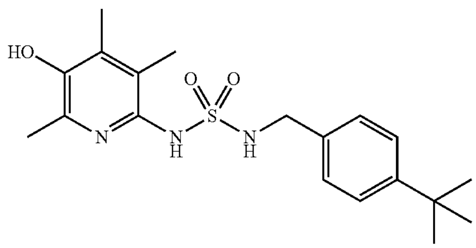 [SMILES: Cc1nc(NS(=O)(=O)NCc2ccc(C(C)(C)C)cc2)c(C)c(C)c1O] | (N-(5-Hydroxy-3,4,6-trimethyl-2-pyridinyl)-N'-(4-(tert-butyl)benzyl)sulfamide) |
| 24-2 | 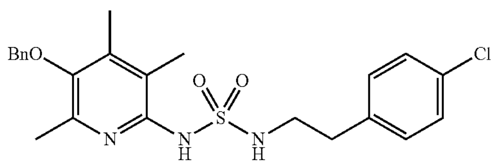 [SMILES: Cc1nc(NS(=O)(=O)NCCc2ccc(Cl)cc2)c(C)c(C)c1OCc1ccccc1] | (N-(5-Benzyloxy-3,4,6-trimethyl-2-pyridinyl)-N'-(4-chlorophenethyl)sulfamide) |
| 25-2 | 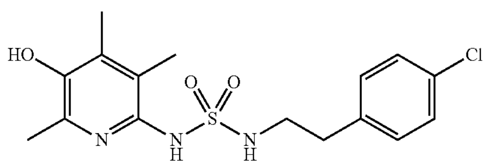 [SMILES: Cc1nc(NS(=O)(=O)NCCc2ccc(Cl)cc2)c(C)c(C)c1O] | (N-(5-Hydroxy-3,4,6-trimethyl-2-pyridinyl)-N'-(4-chlorophenethyl)sulfamide) |

In addition, pyridinol-alkoxide derivatives may be represented by the following formulas.

TABLE 6

| Example | Structure | Name |
|---|---|---|
| 27-1 | 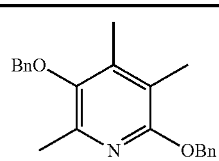 | (2,5-Bis(benzyloxy)-3,4,6-trimethylpyridine) |
| 28-1 | 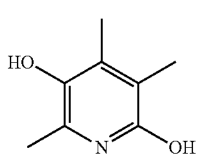 | (3,4,6-Trimethylpyridine-2,5-diol) |
| 27-2 | 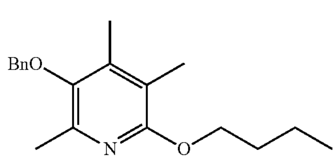 [SMILES: CCCCOc1nc(C)c(OCc2ccccc2)c(C)c1C] | (3-Benzyloxy-6-butoxy-2,4,5-trimethylpyridine) |

TABLE 6-continued

| Example | Structure | Name |
|---|---|---|
| 28-2 | 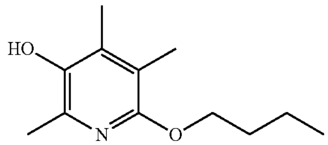 | (6-Butoxy-2,4,5-trimethylpyridin-3-ol) |
| 27-3 | 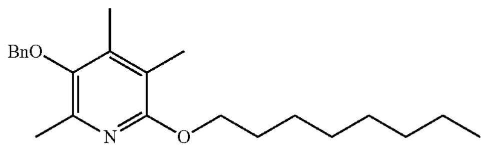 [SMILES: CCCCCCCCOc1nc(C)c(OCc2ccccc2)c(C)c1C] | (3-Benzyloxy-2,4,5-trimethyl-6-(octyloxy)pyridine) |
| 28-3 | 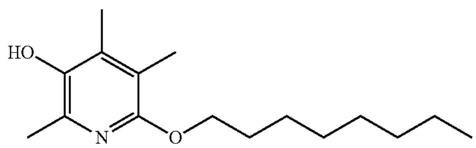 [SMILES: CCCCCCCCOc1nc(C)c(O)c(C)c1C] | (2,4,5-Trimethyl-6-(octyloxy)pyridin-3-ol) |
| 27-4 | 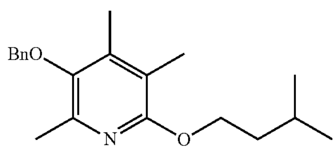 [SMILES: Cc1nc(OCCC(C)C)c(C)c(C)c1OCc1ccccc1] | (3-Benzyloxy-6-isopentyloxy-2,4,5-trimethylpyridine) |
| 28-4 | 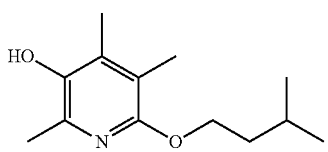 [SMILES: Cc1nc(OCCC(C)C)c(C)c(C)c1O] | (6-Isopentyloxy-2,4,5-trimethylpyridin-3-ol) |
| 27-5 | 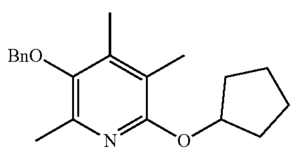 [SMILES: Cc1nc(OC2CCCC2)c(C)c(C)c1OCc1ccccc1] | (3-Benzyloxy-6-cyclopentyloxy-2,4,5-trimethylpyridine) |
| 28-5 | 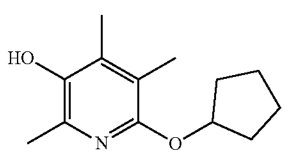 [SMILES: Cc1nc(OC2CCCC2)c(C)c(C)c1O] | (6-Cyclopentyloxy-2,4,5-trimethylpyridin-3-ol) |
| 27-6 | 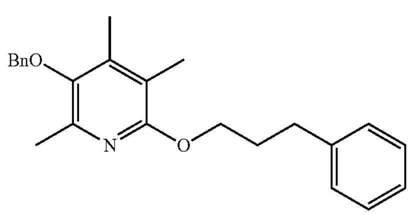 [SMILES: Cc1nc(OCCCc2ccccc2)c(C)c(C)c1OCc1ccccc1] | (3-Benzyloxy-2,4,5-trimethyl-6-(3-phenylpropoxy)pyridine) |
| 28-6 | 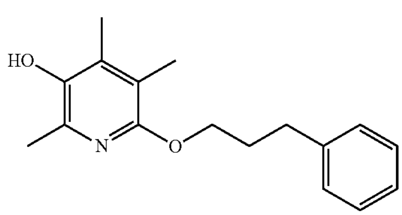 [SMILES: Cc1nc(OCCCc2ccccc2)c(C)c(C)c1O] | (2,4,5-Trimethyl-6-(3-phenylpropoxy)pyridin-3-ol) |

In the present invention, the pharmaceutically acceptable salt may be the form of an acid addition salt formed by an organic acid selected from the group consisting of oxalic acid, maleic acid, fumaric acid, malic acid, tartaric acid, citric acid and benzoic acid, or an inorganic acid selected from the group consisting of hydrochloric acid, sulfuric acid, phosphoric acid and hydrobromic acid.

In addition, the present invention provides a method for preparing a compound of Formula 1. The compound of Formula 1 may be prepared by, for example, reacting a compound of Formula 4 below with a compound of Formula 5 or 6 below;

reacting a compound of Formula 4 below with a compound of Formula 7 below, thereby obtaining a compound of Formula 8, and reacting the compound of Formula 8 with a compound of Formula 9 below; or converting a compound of Formula 4 below into a compound of Formula 10 below, and reacting the compound of Formula 10 with a compound of Formula 11 below.

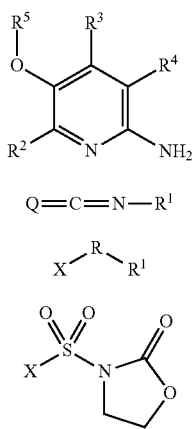

In Formulas 1 to 9, as R1 to R5, and Q and L, the above-described compounds may be used, and R may be carbonyl or sulfonyl, and X may be halogen.

In one exemplary embodiment, the compound of Formula 1 may be prepared by a preparation method illustrated in Reaction Scheme 1 or 2.

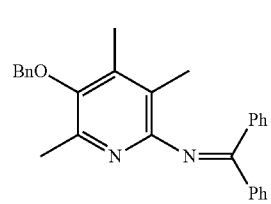 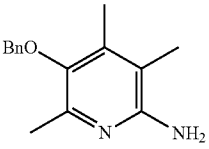 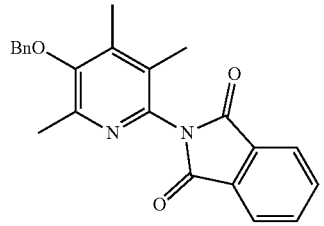
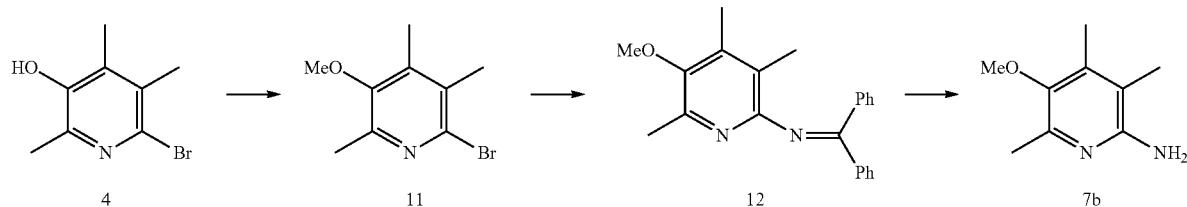
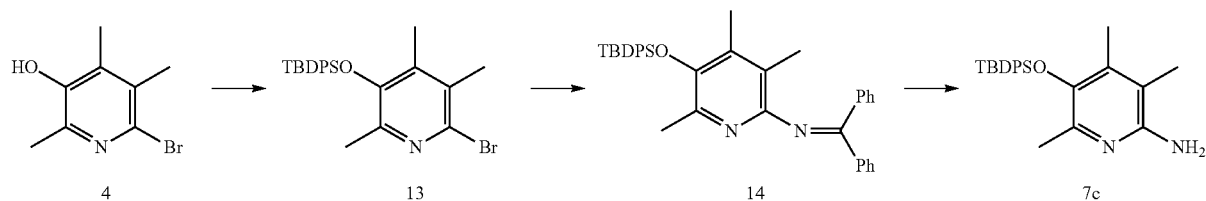
[Reaction Scheme 2]
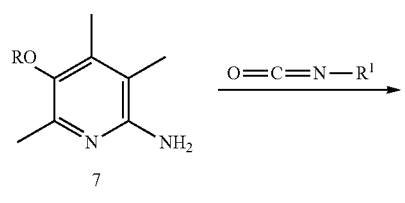
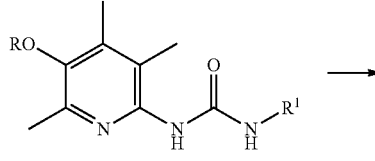
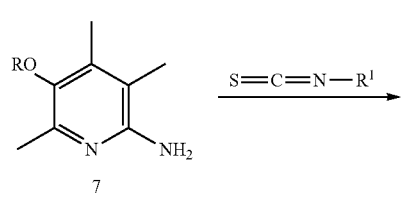
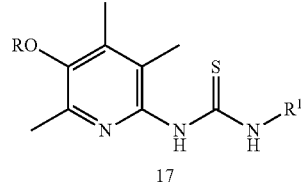
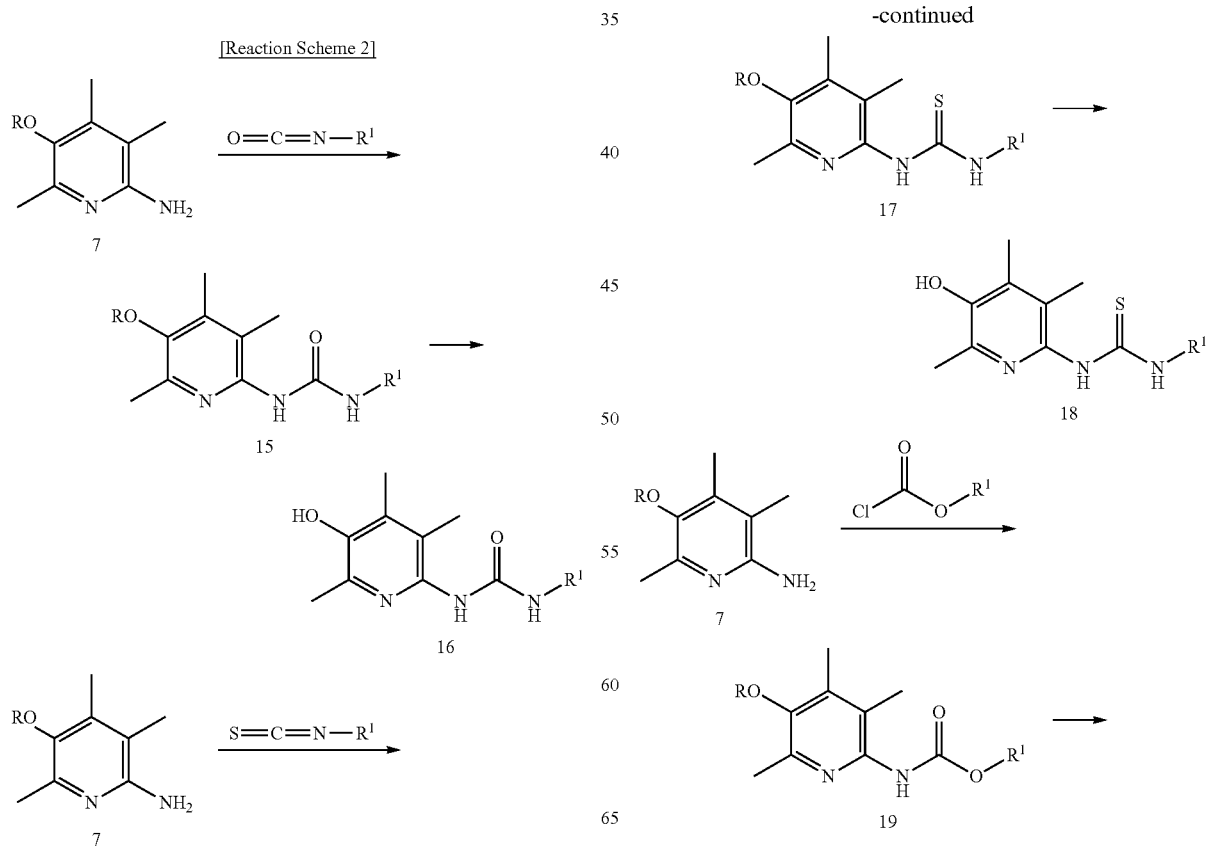

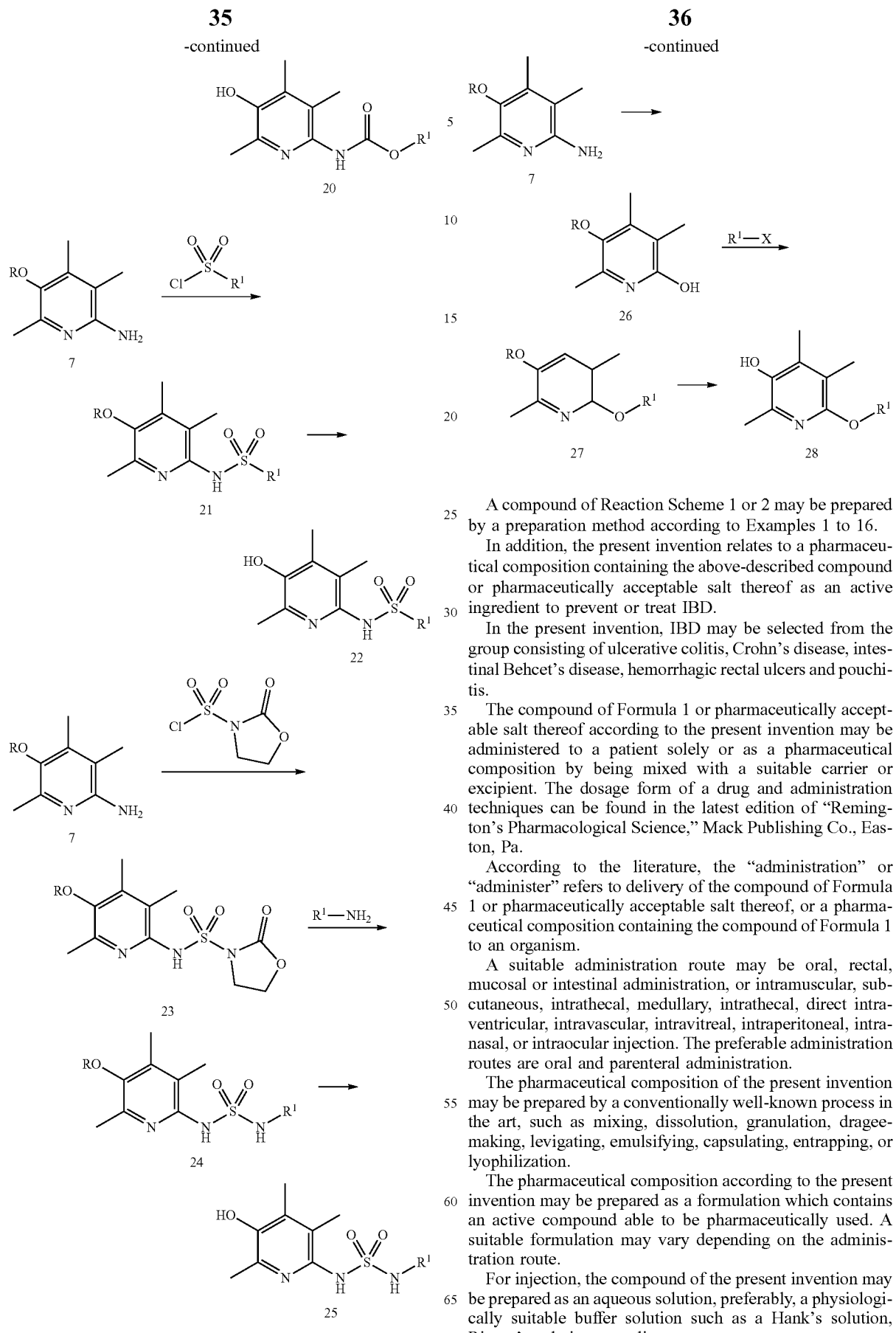

A compound of Reaction Scheme 1 or 2 may be prepared by a preparation method according to Examples 1 to 16.

In addition, the present invention relates to a pharmaceutical composition containing the above-described compound or pharmaceutically acceptable salt thereof as an active ingredient to prevent or treat IBD.

In the present invention, IBD may be selected from the group consisting of ulcerative colitis, Crohn's disease, intestinal Behcet's disease, hemorrhagic rectal ulcers and pouchitis.

The compound of Formula 1 or pharmaceutically acceptable salt thereof according to the present invention may be administered to a patient solely or as a pharmaceutical composition by being mixed with a suitable carrier or excipient. The dosage form of a drug and administration techniques can be found in the latest edition of "Remington's Pharmacological Science," Mack Publishing Co., Easton, Pa.

According to the literature, the "administration" or "administer" refers to delivery of the compound of Formula 1 or pharmaceutically acceptable salt thereof, or a pharmaceutical composition containing the compound of Formula 1 to an organism.

A suitable administration route may be oral, rectal, mucosal or intestinal administration, or intramuscular, subcutaneous, intrathecal, medullary, intrathecal, direct intraventricular, intravascular, intravitreal, intraperitoneal, intranasal, or intraocular injection. The preferable administration routes are oral and parenteral administration.

The pharmaceutical composition of the present invention may be prepared by a conventionally well-known process in the art, such as mixing, dissolution, granulation, dragee-making, levigating, emulsifying, capsulating, entrapping, or lyophilization.

The pharmaceutical composition according to the present invention may be prepared as a formulation which contains an active compound able to be pharmaceutically used. A suitable formulation may vary depending on the administration route.

For injection, the compound of the present invention may be prepared as an aqueous solution, preferably, a physiologically suitable buffer solution such as a Hank's solution, Ringer's solution, or saline.

For nasal administration, a surface-penetrating agent may be used in the formulation so as to allow an active ingredient to penetrate a barrier. Generally, such a surface-penetrating agent may be well known in the art.

For oral administration, the compound may be prepared in combination with a pharmaceutically acceptable carrier. In this case, to administer such a carrier-combined compound through the mouth of a patient, the compound of the present invention may be prepared as tablets, pills, lozenge, dragees, capsules, a liquid, a gel, a syrup, slurries, or a suspension. To make the core of a tablet or lozenge, the pharmaceutical formulation for oral administration may be prepared by adding another suitable additive, if needed, and then adding a solid excipient. Here, optionally, the prepared mixture may be grinded, thereby forming granules. Available excipients may include saccharides such as lactose, sucrose, mannitol or solbitol; fibrous formulations such as corn starch, wheat starch, rice starch, and potato starch; and fillers such as gelatins, gum, rubber sap, methylcellulose, hydroxypropyl-methyl-cellulose, and/or polyvinyl-pyrrolidone (PVP). If needed, a disintegrating agent such as crosslinked PVP, agar or alginic acid may be added. In addition, a salt such as sodium alginate may be added.

The core region of a dragee may be suitably coated. To this end, concentrated sugar solutions containing gum arabic, polyvinylpyrrolidone, carbopol gel, polyethylene glycol and/or titanium dioxide, and a lacquer solution may be optionally used.

Pharmaceutical compositions for oral administration may include a soft encapsulation capsule made of gelatin and a plasticizer such as glycerol or sorbitol, and a push-fit capsule made of gelatin. In the soft capsule, an active compound may be dissolved or suspended in a suitable solution such as fatty oil, liquid paraffin or liquid polyethylene glycol. In addition, a stabilizer may be added to the composition.

The pharmaceutical composition used herein may include a hard gelatin capsule.

Capsules may be contained in a brown glass or plastic bottle to protect an active compound from light. The container having the active compound-contained capsules may be stored at a controlled room temperature (15 to 30° C.).

For inhalation, the compound according to the present invention may be easily administered in the form of a compressed container, a nebulizer, or an aerosol spray using a suitable propellant such as dichlorodifluoromethane, trichlorofluoromethane, dichlorotetra-fluoroethane or carbon dioxide.

In addition, the compound may be prepared to be parenterally administered through, for example, bolus injection or continuous, intravenous injection. An injectable preparation may be provided in the preservative-added form of a unit administration volume, for example, ampoules or multi-dose containers. The composition may be prepared in the form of an oil- or aqueous-phase vehicle such as a suspension, a solution or an emulsion, and include additives for preparation including a suspending agent, a stabilizer and/or a dispersing agent.

Pharmaceutical compositions for parenteral administration may include water-soluble solution forms, such as a water-soluble solution containing a salt as an active compound. In addition, an active compound suspension may be prepared with a lipophilic vehicle. Suitable lipophilic vehicles may include materials such as synthetic fatty acid esters such as fatty oil, ethyl oleate and triglycerides, and liposomes. A water-soluble injectable suspension may contain a material that increases the viscosity of a suspension, such as sodium carboxy methyl cellulose, sorbitol or dextran. In addition, optionally, the suspension may contain a material that can allow the preparation of a high concentration solution by increasing the solubility of a suitable stabilizer and/or compound.

In addition, the compound may be prepared as a compound for rectal administration such as a suppository using a conventional suppository base such as cocoa butter or a glyceride, or an oil-containing enema.

In addition, other than the above-described preparations, the compound may be prepared in the form of a depot preparation. Such a long-acting preparation is administered by implantation (e.g., subcutaneous or intramuscular administration) or intramuscular injection. The compound of the present invention may be prepared to be administered by such a route with a water-insoluble derivative such as a suitable polymeric or hydrophobic material (e.g., an emulsion made of a pharmaceutically acceptable oil), an ion exchange resin or a water-insoluble salt (but not limited thereto).

The pharmaceutical composition according to the present invention refers to a composition including a sufficient amount of active compound to achieve a desired object such as prevention or treatment of any one of diseases selected from the group consisting of the above-described diseases, for example, ulcerative colitis, Crohn's disease, intestinal Behcet's disease, hemorrhagic rectal ulcers and pouchitis.

Here, the therapeutically effective amount refers to a dose that can prevent, alleviate or improve the symptoms of a disease, or prolong the survival of a prescribed patient.

The pyridinol derivative or pharmaceutically acceptable salt thereof according to the present invention inhibits colitis in an IBD model, and thus can be effectively used to prevent or treat IBD.

The pharmaceutical composition according to the present invention may include 0.1 to 50 wt % of the pyridinol derivative or pharmaceutically acceptable salt thereof with respect to the total weight of the composition.

An amount of the pyridinol derivative or pharmaceutically acceptable salt thereof according to the present invention used herein may vary depending on a patient's age, sex and body weight, but may be administered at 0.001 to 100 mg/kg, preferably 0.01 to 10 mg/kg one to several times a day. In addition, a dosage of the pyridinol derivative or pharmaceutically acceptable salt thereof may be changed according to an administration route, the severity of a disease, sex, body weight or age. Accordingly, the dosage does not limit the scope of the present invention in any way.

The pharmaceutical composition may be administered by various routes to mammals such as rats, mice, livestock, and humans. The administration may be performed by any expected method such as oral, rectal or intravenous, intramuscular, subcutaneous, intrauterine or intracerebroventricular injection.

The pyridinol derivative or pharmaceutically acceptable salt thereof according to the present invention has a lethal concentration 50% (LC50) of 2 g/kg or more, thereby securing stability, and thus can be used in the pharmaceutical composition of the present invention.

Hereinafter, the present invention will be described in detail to help in understanding the present invention. However, it should be understood that the following examples are merely used to illustrate the disclosure of the present invention, and thus the scope of the present invention is not limited thereto.

EXAMPLES

<Example 1> Preparation of 4,5-bis(chloromethyl)-2-methylpyridin-3-ol hydrochloride (2)

30 mL of thionyl chloride and 0.2 mL (2.583 mmol) of DMF were added to 5 g (24.31 mmol) of pyridoxine HCl, and then stirred at 80° C. for 3 hours while refluxing. After the reaction solution was cooled to room temperature, 70 mL of Et2O was added thereto, and then the resulting mixture was stirred for 1 hour while ice-cooling. A precipitated solid was subjected to vacuum filtration, and the filtered solid was washed with Et2O and then dried, thereby obtaining a white solid, Compound 2 (5.5 g, 93%).

1H-NMR ((CD3)2SO) δ 8.42 (s, 1H), 4.99 (s, 2H), 4.96 (s, 2H), 2.63 (s, 3H) ppm.

<Example 2> Preparation of 2,4,5-trimethylpyridin-3-ol (3)

8.08 g (123.69 mmol) of zinc (Zn) powder was added in small amounts into 50 mL of an AcOH suspension containing 10 g (41.23 mmol) of Compound 2, and stirred at 130° C. for 2 hours. After being cooled to room temperature, the reaction solution was subjected to vacuum filtration, and a 10 M NaOH aqueous solution was used to adjust a pH of the filtrate to 6. The resulting solution was saturated with salt, and extracted with EtOAc (6×100 mL). The EtOAc solution was washed with saturated brine, dried with anhydrous MgSO4, filtered, and then concentrated under reduced pressure. A residue was purified by column chromatography (CHCl3:MeOH=20:1), thereby obtaining white solid, compound 3 (5.2 g, 92%).

1H-NMR ((CD3)2SO) δ 8.49 (s, 1H), 7.72 (s, 1H), 2.31 (s, 3H), 2.12 (s, 3H), 2.08 (s, 3H) ppm.

<Example 3> Preparation of 6-bromo-2,4,5-trimethylpyridin-3-ol (4)

2.5 g (9.11 mmol) of 1,3-dibromo-5,5-dimethylhydantoin (DBDMH) was added to 30 mL of a THF suspension solution containing 2.5 g (18.22 mmol) of compound 3, and stirred at room temperature for 3 hours. After the reaction solution was concentrated, a residue was diluted with 500 mL of EtOAc and 20 mL of water, and then an aqueous layer was extracted with EtOAc (3×100 mL). The EtOAc solution was washed with saturated brine, dried with anhydrous MgSO4, filtered and then concentrated under reduced pressure. A residue was purified by column chromatography (EtOAc:Hex=1:4), thereby obtaining a pale yellow solid, Compound 4 (3.22 g, 80%).

1H-NMR (CDCl3) δ 5.56 (br s, 1H), 2.42 (s, 3H), 2.31 (s, 3H), 2.25 (s, 3H) ppm.

<Example 4> Preparation of 3-benzyloxy-6-bromo-2,4,5-trimethylpyridine (5)

20.78 g (150.04 mmol) of K2CO3 and 5.2 mL (45.12 mmol) of benzyl chloride were sequentially added to 15 mL of a DMF solution containing 6.5 g (30.08 mmol) of compound 4 and stirred at room temperature for 12 hours. The reaction solution was diluted with 700 mL of EtOAc and washed with water (10×20 mL). The EtOAc solution was washed with saturated brine, dried with anhydrous MgSO4, filtered and concentrated under reduced pressure. A residue was purified by column chromatography (EtOAC:Hex=1:20), thereby obtaining a white solid, Compound 5 (8.9 g, 97%).

1H-NMR (CDCl3) δ 7.38-7.43 (m, 5H), 4.77 (s, 2H), 2.46 (s, 3H), 2.32 (s, 3H), 2.24 (s, 3H) ppm.

<Example 5> Preparation of 5-benzyloxy-N-(diphenylmethylene)-3,4,6-trimethylpyridin-2-amine (6)

1.73 mL (9.80 mmol) of benzophenone imine was added to 30 mL of a toluene solution containing 3 g (9.80 mmol) of Compound 5, 203 mg (0.20 mmol) of tris(dibenzylideneacetone)dipalladium (0) (Pd2(DBA)3), 249 mg (0.39 mmol) of 2,2'-bis(diphenylphosphino)-1,1'-binaphthyl (BINAP) and 1.36 g (13.71 mmol) of NaOtBu, and stirred at 120° C. for 12 hours while refluxing. After the reaction solution was cooled to room temperature, it was diluted with EtOAc (700 mL) and water (10 mL), and the EtOAc solution was washed with saturated brine (5×30 mL). The EtOAc solution was dried with anhydrous MgSO4, filtered, and concentrated under reduced pressure. A residue was purified by column chromatography (EtOAc:Hex=1:4), thereby obtaining a yellow solid, Compound 6 (3.28 g, 83%).

1H-NMR (CDCl3) δ 7.80 (d, J=7.1 Hz, 2H), 7.17-7.48 (m, 13H), 4.69 (s, 2H), 2.29 (s, 3H), 2.03 (s, 3H), 1.91 (s, 3H) ppm.

<Example 6> Preparation of 5-benzyloxy-3,4,6-trimethylpyridin-2-amine (7a)

A solution in which 2 mL of acetyl chloride was slowly added to 50 mL of cold methanol was added to a solution of Compound 6 (2 g, 4.920 mmol) containing 50 mL of MeOH-5 mL of THF and stirred at room temperature for 12 hours. The reaction solution was concentrated under reduced pressure, diluted with 300 mL of EtOAc, and washed with a saturated NaHCO3 solution (4×20 mL). The EtOAc solution was washed with saturated brine (20 mL), dried with anhydrous MgSO4, filtered and concentrated under vacuum pressure. A residue was purified by column chromatography (CHCl3:MeOH=20:1), thereby obtaining a pale yellow solid, Compound 7a (992 mg, 83%).

1H-NMR (CDCl3) δ 7.31-7.45 (m, 5H), 4.68 (s, 2H), 4.25 (br s, 1H), 2.34 (s, 3H), 2.16 (s, 3H), 1.99 (s, 3H) ppm.

<Example 7> Preparation of 3-benzyloxy-2,4,5-trimethylpyridine (8)

2.5 g (18.224 mmol) of K2CO3 and 0.63 mL (5.467 mmol) of benzyl chloride were added to 10 mL of a DMF suspension containing Compound 3 (500 mg, 3.644 mmol), and stirred at room temperature for 12 hours. After the reaction solution was concentrated, a residue was diluted with 300 mL of EtOAc, and the EtOAc solution was washed with water (3×30 mL). The EtOAc solution was dried with anhydrous MgSO4, filtered, and concentrated under reduced pressure. A residue was purified by column chromatography (EtOAc:Hex=1:20), thereby obtaining a yellow liquid containing Compound 8 (593 mg, 71%).

1H-NMR (CDCl3) δ 8.03 (s, 1H), 7.33-7.46 (m, 5H), 4.77 (s, 2H), 2.47 (s, 3H), 2.19 (s, 3H), 2.17 (s, 3H) ppm.

<Example 8> Preparation of 3-benzyloxy-2,4,5-trimethylpyridine 1-oxide (9)

549 mg of m-chloroperbenzoic acid (m-CPBA, 2.226 mmol) was added to 10 mL of a CH2Cl2 suspension containing Compound 8 (460 mg, 2.023 mmol), and stirred at room temperature for 1 hour. A saturated NaHCO$_3$ aqueous solution was added to the reaction solution and extracted with CH2Cl2 (3×30 mL). The CH2Cl2 solution was dried with anhydrous MgSO4, filtered and concentrated under reduced pressure. A residue was purified by column chromatography (CHCl3:MeOH=30:1), thereby obtaining a white solid, Compound 9 (463 mg, 94%).

1H-NMR (CDCl3) δ 8.00 (s, 1H), 7.36-7.41 (m, 5H), 4.77 (s, 2H), 2.44 (s, 3H), 2.17 (s, 3H), 2.13 (s, 3H) ppm.

<Example 9> Preparation of 2-(5-benzyloxy-3,4,6-trimethylpyridin-2-yl)isoindoline-1,3-dione (10)

82 mg (0.557 mmol) of phthalimide, 133 mg (0.696 mmol) of p-toluenesulfonyl chloride and 242.5 μL (1.392 mmol) of N,N-diisopropylethylamine were added to 2 mL of a CH2Cl2 suspension containing Compound 9 (113 mg, 0.464 mmol) and stirred at room temperature for 15 hours. The reaction solution was diluted with CH2Cl2, and washed with a saturated NaHCO$_3$ aqueous solution and saturated brine. The CH2Cl2 solution was dried with anhydrous MgSO4, filtered and concentrated under reduced pressure. A residue was purified by column chromatography (EtOAc:Hex=1:5), thereby obtaining a white solid, Compound 10 (136 mg, 79%).

1H-NMR (CDCl3) δ 7.90-7.95 (m, 2H), 7.74-7.81 (m, 2H), 7.36-7.50 (m, 5H), 4.83 (s, 2H), 2.52 (s, 3H), 2.28 (s, 3H), 2.10 (s, 3H) ppm.

<Example 10> Preparation of 5-benzyloxy-3,4,6-trimethylpyridin-2-amine (7a)

0.84 mL of hydrazine hydrate was added to a THF-EtOH (1:1, 12 mL) suspension containing Compound 10 (454 mg, 1.222 mmol), and stirred at room temperature for 1 hour. The reaction solution was concentrated and diluted with CH2Cl2 and a saturated NaHCO$_3$ aqueous solution, and an aqueous layer was extracted with CH2Cl2 (3×100 mL). The CH2Cl2 solution was dried with anhydrous MgSO4, filtered and concentrated under reduced pressure. A residue was purified by column chromatography (EtOAc:Hex=1:5), thereby obtaining a white solid, Compound 7a (249 mg, 84%).

1H-NMR (CDCl3) δ 7.31-7.45 (m, 5H), 4.68 (s, 2H), 4.25 (br s, 1H), 2.34 (s, 3H), 2.16 (s, 3H), 1.99 (s, 3H) ppm.

<Example 11> Preparation of 2-bromo-5-methoxy-3,4,6-trimethylpyridine (11)

213 mg (1.0 mmol) of Compound 4 was dissolved in 10 mL of CH3CN, and 0.12 mL (2.0 mmol) of iodomethane and 207 mg (1.5 mmol) of K2CO3 were added thereto and then stirred at 50° C. for 16 hours. The reaction solution was diluted with 100 mL of EtOAc, and sequentially washed with a 1 N HCl aqueous solution, water and saturated saline. The EtOAc solution was dried with anhydrous MgSO4, filtered and concentrated under reduced pressure. A residue was purified by column chromatography (EtOAc:Hex=1:9), thereby obtaining a yellow solution containing Compound 11 (154 mg, 67%).

1H-NMR (CDCl3) δ 3.67 (s, 3H), 2.44 (s, 3H), 2.30 (s, 3H), 2.24 (s, 3H) ppm.

<Example 12> Preparation of N-(diphenylmethylene)-5-methoxy-3,4,6-trimethylpyridin-2-amine (12)

42 mg (0.067 mmol) of BINAP, 31 mg (0.034 mmol) of Pd2(dba)3, 71 mg (0.74 mmol) of NaOtBu and 0.11 mL (0.67 mmol) of benzophenone imine were added to 5 mL of a toluene suspension containing Compound 11 (155 mg, 0.67 mmol), and stirred for 16 hours while refluxing. The reaction solution was diluted with 50 mL of EtOAc, and washed with water and saturated brine. The EtOAc solution was dried with anhydrous MgSO4, filtered and concentrated under reduced pressure. A residue was purified by column chromatography (EtOAc:Hex=1:4), thereby obtaining a yellow solid, Compound 12 (170 mg, 77%).

1H-NMR (CDCl3) 7.80-7.36 (m, 10H), 3.66 (s, 3H), 2.52 (s, 3H), 2.29 (s, 3H), 2.10 (s, 3H) ppm.

<Example 13> Preparation of 5-methoxy-3,4,6-trimethylpyridin-2-amine (7b)

A THF-MeOH (1:10, 5.5 mL) solution of Compound 12 (168 mg, 0.51 mmol) was cooled to 0° C., 1.0 mL of a CH3COCl-MeOH mixed solution (1:10) was slowly added and stirred at room temperature for 18 hours. The reaction solution was concentrated under reduced pressure, and a residue was diluted with 100 mL of water and 100 mL of EtOAc. An aqueous layer and an organic layer were separated, and the organic layer was extracted with 50 mL of water. Aqueous solutions were collected, and a 1 N NaOH aqueous solution was added thereto, adjusted to a pH of 10 and extracted with EtOAc (3×50 mL). The EtOAc solution was dried with anhydrous MgSO4, filtered and concentrated under reduced pressure. A residue was purified by column chromatography (CH2Cl2:MeOH=30:1), thereby obtaining a gray solid, Compound 7b (54 mg, 64%).

1H-NMR ((CD3)2SO) δ 5.22 (s, 2H), 3.52 (s, 3H), 2.17 (s, 3H), 2.06 (s, 3H), 1.91 (s, 3H) ppm.

<Example 14> Preparation of 2-bromo-5-(tert-butyldiphenylsilyloxy)-3,4,6-trimethylpyridine (13)

759 mg (11.15 mmol) of imidazole was added to 9 mL of a DMF solution of Compound 4 (964 mg, 4.46 mmol), and stirred for 20 minutes. 1.4 mL of tert-butyldiphenylchlorosilane (TBDPSCl, 5.35 mmol) was added thereto, and stirred at room temperature for 24 hours. The reaction product was diluted with 100 mL of Et2O and washed with water. The Et2O solution was dried with anhydrous MgSO4, filtered and concentrated under reduced pressure. A residue was purified by column chromatography (EtOAc:Hex=1:45), thereby obtaining a colorless liquid, Compound 13 (1.75 g, yield: 87%).

1H-NMR (CDCl3) δ 7.68-7.60 (m, 4H), 7.44-7.38 (m, 2H), 7.36-7.31 (m, 4H), 2.21 (s, 3H), 2.16 (s, 3H), 1.98 (s, 3H), 1.10 (s, 9H) ppm.

<Example 15> Preparation of 5-(tert-Butyldiphenylsilyloxy)-N-(diphenylmethylene)-3,4,6-trimethylpyridin-2-amine (14)

0.65 mL (3.84 mmol) of benzophenone imine was added to 19 mL of a toluene suspension containing Compound 13 (1.74 g, 3.84 mmol), 389 mg (4.23 mmol) of NaOtBu, 176 mg (0.19 mmol) of Pd2(dba)3 and 239 mg (0.39 mmol) of BINAP, and stirred for 5 hours while refluxing. The reaction product was cooled to room temperature, diluted with 100 mL of EtOAc, and washed with saturated brine. The EtOAc solution was dried with anhydrous MgSO4, filtered and concentrated under reduced pressure. A residue was purified by column chromatography (EtOAc:Hex=1:45), thereby obtaining a yellow solid, Compound 14 (1.88 g, 89%).

1H-NMR ((CD3)2SO) δ 7.70-7.64 (m, 2H), 7.60-7.55 (m, 4H), 7.55-7.51 (m, 1H), 7.50-7.44 (m, 4H), 7.41-7.27 (m, 7H), 7.07-7.02 (m, 2H), 1.87 (s, 3H), 1.85 (s, 3H), 1.84 (s, 3H), 1.02 (s, 9H) ppm.

<Example 16> Preparation of 5-(tert-butyldiphenyl-silyloxy)-3,4,6-trimethylpyridin-2-amine (7c)

A THF-MeOH (1:10, 22 mL) solution of Compound 14 (2.29 g, 4.14 mmol) was cooled to 0° C., 1.0 mL of a CH3COCl-MeOH mixed solution (1:10) was slowly added dropwise, and stirred at room temperature for 24 hours. The reaction solution was concentrated under reduced pressure, a residue was diluted with 200 mL of EtOAc, and washed with a saturated NaHCO$_3$ aqueous solution. The EtOAc solution was dried with anhydrous MgSO4, filtered and concentrated under reduced pressure. A residue was purified by column chromatography (CH2Cl2:MeOH=45:1), thereby obtaining a brown liquid, Compound 7c (1.49 g, 93%).

1H-NMR ((CD3)2SO) δ 7.66-7.61 (m, 4H), 7.49-7.43 (m, 2H), 7.43-7.37 (m, 4H), 5.03 (s, 2H), 1.92 (s, 3H), 1.86 (s, 3H), 1.85 (s, 3H), 1.04 (s, 9H) ppm.

Example 17. Preparation of pyridinol-urea derivatives

<Example 17-1> Preparation of 1-(5-benzyloxy-3,4,6-trimethylpyridin-2-yl)-3-propylurea (15-1)

46.4 μl of propyl isocyanate was added to 5 mL of a CH2Cl2 suspension containing Compound 7a (100 mg, 0.413 mmol), and stirred at room temperature for 40 hours. Silica gel was added to the reaction solution for concentration, and then a residue was purified by column chromatography (CHCl3:MeOH=50:1→20:1), thereby obtaining a white solid, Compound 15-1 (125 mg, 92%).

1H-NMR (CDCl3) 9.77 (s, 1H), 7.48-7.30 (m, 5H), 6.67 (s, 1H), 4.72 (s, 2H), 3.33 (td, J=6.9, 5.6 Hz, 2H), 2.38 (s, 3H), 2.20 (s, 3H), 2.08 (s, 3H), 1.62 (dd, J=14.3, 7.1 Hz, 2H), 1.00 (t, J=7.4 Hz, 3H) ppm.

<Example 17-2> Preparation of 1-(5-hydroxy-3,4,6-trimethylpyridin-2-yl)-3-propylurea (16-1)

21 mg of 10% palladium on activated carbon was added to 4 mL of a CH2Cl2 suspension containing Compound 15-1 (105 mg, 0.321 mmol), and stirred at room temperature for 2 hours under a hydrogen atmosphere. The reaction solution was filtrated with Celite, and the filtrate was concentrated under reduced pressure. A residue was purified by column chromatography (CH2Cl2:MeOH=20:1), thereby obtaining a white solid, Compound 16-1 (58 mg, 75%).

1H-NMR ((CD3)2SO) δ 8.88 (s, 1H), 8.20 (s, 1H), 7.71 (s, 1H), 3.31 (s, 2H), 3.14 (dd, J=12.4, 6.7 Hz, 2H), 2.29 (s, 3H), 2.12 (s, 3H), 2.05 (s, 3H), 1.56-1.40 (m, 2H), 0.91 (t, J=7.4 Hz, 3H) ppm.

<Example 17-3> Preparation of 1-(5-benzyloxy-3,4,6-trimethylpyridin-2-yl)-3-phenylurea (15-2)

47.5 μl (0.289 mmol) of phenyl isocyanate was added to 3 mL of a CH2Cl2 suspension containing Compound 7a (70 mg, 0.289 mmol) and stirred at room temperature for 7 hours. Silica gel was added to the reaction solution for concentration, and a residue was purified by column chromatography (CH2Cl2:MeOH=20:1), thereby obtaining a white solid, Compound 15-2 (99 mg, 95%).

1H-NMR ((CD3)2SO) δ 11.64 (s, 1H), 8.41 (s, 1H), 7.56-7.35 (m, 7H), 7.34-7.25 (m, 2H), 7.05-6.96 (m, 1H), 4.78 (s, 2H), 2.43 (s, 3H), 2.21 (s, 3H), 2.15 (s, 3H) ppm.

<Example 17-4> Preparation of 1-(5-hydroxy-3,4,6-trimethylpyridin-2-yl)-3-phenylurea (16-2)

15.8 mg of 10% palladium on activated carbon was added to 4 mL of a MeOH—CH2Cl2 suspension containing Compound 15-2 (79 mg, 0.219 mmol), and stirred at room temperature for 3 hours under a hydrogen atmosphere. The reaction solution was filtrated with Celite, and the filtrate was concentrated under reduced pressure. A residue was dissolved in MeOH and filtrated with a membrane filter, and the filtrate was concentrated under a reduced pressure, thereby obtaining a white solid, Compound 16-2 (58 mg, 97%).

1H-NMR ((CD3)2SO) δ 11.38-11.33 (m, 1H), 8.27 (s, 1H), 7.51 (d, J=7.6 Hz, 2H), 7.29 (t, J=7.9 Hz, 2H), 6.98 (t, J=7.3 Hz, 1H), 2.38 (s, 3H), 2.15 (s, 3H), 2.09 (s, 3H) ppm.

<Example 17-5> Preparation of 1-(5-benzyloxy-3,4,6-trimethylpyridin-2-yl)-3-(4-chlorophenyl)urea (15-3)

63.4 mg (0.413 mmol) of 4-chlorophenyl isocyanate was added to 5 mL of a CH2Cl2 suspension containing Compound 7a (100 mg, 0.413 mmol), and stirred at room temperature for 7 hours. Silica gel was added to the reaction solution for concentration, and a residue was purified by column chromatography (CH2Cl2:MeOH=50:1→20:1), thereby obtaining a white solid, Compound 15-3 (64 mg, 79%).

1H-NMR (CDCl3) δ 12.47 (s, 1H), 7.57-7.48 (m, 2H), 7.47-7.34 (m, 5H), 7.30-7.24 (m, 2H), 6.87 (s, 1H), 4.75 (s, 2H), 2.47 (s, 3H), 2.24 (s, 3H), 2.14 (s, 3H) ppm.

<Example 17-6> Preparation of 1-(4-Chlorophenyl)-3-(5-hydroxy-3,4,6-trimethylpyridin-2-yl)urea (16-3)

72 mg (0.486 mmol) of pentamethylbenzene was added to 4 mL of a CH2Cl2 suspension containing Compound 15-3 (64 mg, 0.162 mmol), 0.32 mL of boron trichloride (1 M BCl3 in CH2Cl2) was slowly added thereto, and the resulting solution was stirred at 0° C. for 3 hours. 1 mL of a CHCl3-MeOH solution (9:1) was added to the reaction solution and stirred for 30 minutes, and then the reaction solution was concentrated. A residue was purified by column chromatography (CHCl3:MeOH=30:1), thereby obtaining a white solid, Compound 16-3 (28 mg, 57%).

1H-NMR ((CD3)2SO) δ 10.75 (s, 1H), 10.03 (s, 2H), 7.57-7.49 (m, 2H), 7.41-7.33 (m, 2H), 2.53 (s, 3H), 2.32 (s, 3H), 2.28 (s, 3H) ppm.

<Example 17-7> Preparation of 1-(5-benzyloxy-3,4,6-trimethylpyridin-2-yl)-3-(2-tert-butyl-6-methylphenyl)urea (15-4)

58.2 μl (0.289 mmol) of 2-tert-butyl-6-methylphenyl isocyanate was added to 2 mL of a CH2Cl2 suspension containing Compound 7a (70 mg, 0.289 mmol), and stirred at room temperature for 26 hours. Silica gel was added to the reaction solution for concentration, and a residue was purified by column chromatography (CHCl3:MeOH=50:1→30:1), thereby obtaining a white solid, Compound 15-4 (118 mg, 82%).

1H-NMR (CDCl3) δ 11.48 (s, 1H), 7.47-7.27 (m, 6H), 7.18-7.12 (m, 2H), 6.83 (s, 1H), 4.75 (s, 2H), 2.34 (s, 3H), 2.30 (s, 3H), 2.26 (s, 3H), 2.15 (s, 3H), 1.43 (s, 9H) ppm.

<Example 17-8> Preparation of 1-(2-tert-butyl-6-methylphenyl)-3-(5-hydroxy-3,4,6-trimethylpyridin-2-yl)urea (16-4)

10 mg of 10% palladium on activated carbon was added to 3 mL of a MeOH—CH2Cl2 suspension containing Compound 15-4 (50 mg, 0.116 mmol), and stirred at room temperature for 2 hours under a hydrogen atmosphere. The reaction solution was filtrated with Celite, and the filtrate was concentrated under reduced pressure. A residue was dissolved in MeOH and filtrated with a membrane filter, and the filtrate was concentrated under reduced pressure, thereby obtaining a pale yellow solid, Compound 16-4 (35 mg, 88%).

1H-NMR ((CD3)2SO) δ 10.91 (s, 1H), 8.38 (s, 1H), 8.26 (s, 1H), 7.23 (dd, J=8.7, 4.5 Hz, 1H), 7.11 (dd, J=7.4, 5.7 Hz, 2H), 2.26 (s, 3H), 2.18-2.12 (m, 9H), 1.35 (s, 9H) ppm.

<Example 17-9> Preparation of 1-(5-benzyloxy-3,4,6-trimethylpyridin-2-yl)-3-(naphthalen-1-yl)urea (15-5)

42.7 μl (0.289 mmol) of 1-naphthyl isocyanate was added to 3 mL of a CH2Cl2 suspension containing Compound 7a (70 mg, 0.289 mmol) and stirred at room temperature for 12 hours. Silica gel was added to the reaction solution for concentration, and a residue was purified by column chromatography (CHCl3:MeOH=30:1), thereby obtaining a white solid, Compound 15-5 (99 mg, 83%).

1H-NMR (CDCl3) δ 12.68 (s, 1H), 8.35-8.19 (m, 2H), 7.89-7.84 (m, 1H), 7.65-7.34 (m, 9H), 6.91 (s, 1H), 5.28 (s, 2H), 4.78 (s, 2H), 2.56 (s, 3H), 2.27 (s, 3H), 2.19 (s, 3H) ppm.

<Example 17-10> Preparation of 1-(5-hydroxy-3,4,6-trimethylpyridin-2-yl)-3-(naphthalen-1-yl)urea (16-5)

10 mg of 10% palladium on activated carbon was added to 4 mL of a MeOH-THF-CH2Cl2 suspension containing Compound 15-5 (49 mg, 0.119 mmol) and stirred at room temperature for 5 hours under a hydrogen atmosphere. The reaction solution was filtrated with Celite, and the filtrate was concentrated under reduced pressure. A residue was purified by column chromatography (CHCl3:MeOH=20:1), thereby obtaining a pale yellow solid, Compound 16-5 (31 mg, 82%).

1H-NMR ((CD3)2SO) δ 12.08 (s, 1H), 8.43 (s, 1H), 8.22 (dd, J=11.2, 8.0 Hz, 2H), 7.96 (d, J=7.5 Hz, 1H), 7.68-7.45 (m, 4H), 2.50 (s, 3H), 2.20 (s, 6H) ppm.

<Example 17-11> Preparation of N-((5-benzyloxy-3,4,6-trimethylpyridin-2-yl)carbamoyl)benzenesulfonamide (15-6)

31.5 μl (0.206 mmol) of p-toluenesulfonyl isocyanate was added to 1.5 mL of a CH2Cl2 suspension containing Compound 7a (50 mg, 0.206 mmol), and stirred at room temperature for 24 hours. Silica gel was added to the reaction solution for concentration, and a residue was purified by column chromatography (CHCl3:MeOH=40:1), thereby obtaining a white solid, Compound 15-6 (75 mg, 83%).

1H-NMR (CDCl3) δ 7.96 (d, J=8.3 Hz, 2H), 7.43-7.34 (m, 5H), 7.32-7.36 (d, J=8.0 Hz, 2H), 4.74 (s, 2H), 2.45 (s, 3H), 2.39 (s, 3H), 2.21 (s, 3H), 2.06 (s, 3H) ppm.

<Example 17-12> Preparation of N-((5-hydroxy-3,4,6-trimethylpyridin-2-yl)carbamoyl)benzenesulfonamide (16-6)

50 mg of 10% palladium on activated carbon was added to 10 mL of a MeOH—CH2Cl2 suspension containing Compound 15-6 (251 mg, 0.571 mmol), and stirred at room temperature for 3 hours under a hydrogen atmosphere. The reaction solution was filtrated with Celite, and the filtrate was concentrated under reduced pressure. A residue was dissolved in MeOH and filtrated with a membrane filter, and the filtrate was concentrated under reduced pressure, thereby obtaining a white solid, Compound 16-6 (107 mg, 54%).

1H-NMR (CDCl3) δ 7.87 (d, J=8.1 Hz, 2H), 7.20 (d, J=8.1 Hz, 2H), 2.38 (s, 3H), 2.34 (s, 3H), 2.19 (s, 3H), 2.03 (s, 3H) ppm.

<Example 17-13> Preparation of 1-(5-benzyloxy-3,4,6-trimethylpyridin-2-yl)-3-(4-fluorophenyl)urea (15-7)

23 μl (0.206 mmol) of 4-fluorophenyl isocyanate was added to 2 mL of a CH2Cl2 suspension containing Compound 7a (50 mg, 0.206 mmol), and stirred at room temperature for 18 hours. Silica gel was added to the reaction solution for concentration, and a residue was purified by column chromatography (CH2Cl2:MeOH=99:1), thereby obtaining a white solid, Compound 15-7 (67 mg, 86%).

1H-NMR (CDCl3) δ 12.32 (s, 1H), 7.59-7.51 (m, 2H), 7.49-7.37 (m, 5H), 7.05 (t, J=8.7 Hz, 2H), 6.81 (br s, 1H), 4.78 (s, 2H), 2.48 (s, 3H), 2.27 (s, 3H), 2.18 (s, 3H) ppm.

<Example 17-14> Preparation of 1-(4-fluorophenyl)-3-(5-hydroxy-3,4,6-trimethylpyridin-2-yl)urea (16-7)

79 mg (0.530 mmol) of pentamethylbenzene and 0.35 mL (0.353 mmol) of BCl3 were added to 3 mL of a CH2Cl2 suspension containing Compound 15-7 (62 mg, 0.164 mmol), and stirred at room temperature for 2 hours under an argon atmosphere.

The reaction solution was filtrated, thereby obtaining a white solid, Compound 16-7 (43 mg, 90%).

1H-NMR (CD3OD) δ 7.52-7.43 (m, 2H), 7.02 (t, J=8.8 Hz, 2H), 2.43 (s, 3H), 2.23 (s, 3H), 2.17 (s, 3H) ppm.

<Example 17-15> Preparation of 1-(5-benzyloxy-3,4,6-trimethylpyridin-2-yl)-3-(4-bromophenyl)urea (15-8)

61.2 mg (0.309 mmol) of 4-bromophenyl isocyanate was added to 2 mL of a CH2Cl2 suspension containing Compound 7a (50 mg, 0.206 mmol), and stirred at room temperature for 18 hours. Silica gel was added to the reaction solution for concentration, and a residue was purified by column chromatography (CH2Cl2:MeOH=99:1), thereby obtaining a white solid, Compound 15-8 (80 mg, 89%).

1H-NMR (CDCl3) δ 12.44 (s, 1H), 7.55-7.36 (m, 9H), 6.85 (br s, 1H), 4.78 (s, 2H), 2.48 (s, 3H), 2.27 (s, 3H), 2.18 (s, 3H) ppm.

<Example 17-16> Preparation of 1-(4-Bromophenyl)-3-(5-hydroxy-3,4,6-trimethylpyridin-2-yl)urea (16-8)

75 mg (0.505 mmol) of pentamethylbenzene and 0.34 mL (0.337 mmol) of BCl3 were added to 2 mL of a CH2Cl2 suspension containing Compound 15-8 (74 mg, 0.168 mmol), and stirred under an argon atmosphere at room temperature for 2 hours. The reaction solution was filtrated, thereby obtaining a yellow solid, Compound 16-8 (30 mg, 50%).
1H-NMR (CD3OD) δ 7.43 (s, 4H), 2.49 (s, 3H), 2.30 (s, 3H), 2.23 (s, 3H) ppm.

<Example 17-17> Preparation of 1-(5-benzyloxy-3,4,6-trimethylpyridin-2-yl)-3-(p-tolyl)urea (15-9)

26 μl (0.206 mmol) of p-tolyl isocyanate was added to 2 mL of a CH2Cl2 suspension containing Compound 7a (50 mg, 0.206 mmol), and stirred at room temperature for 18 hours. Silica gel was added to the reaction solution for concentration, and a residue was purified by column chromatography (CH2Cl2:MeOH=99:1), thereby obtaining a white solid, Compound 15-7 (76 mg, 98%).
1H-NMR (CDCl3) δ 12.23 (s, 1H), 7.53-7.37 (m, 7H), 7.14 (d, J=8.2 Hz, 2H), 6.86 (brs, 1H), 4.78 (s, 2H), 2.48 (s, 3H), 2.33 (s, 3H), 2.26 (s, 3H), 2.17 (s, 3H) ppm.

<Example 17-18> Preparation of 1-(5-hydroxy-3,4,6-trimethylpyridin-2-yl)-3-(p-tolyl)urea (16-9)

15 mg of 10% palladium on activated carbon was added to 2 mL of a MeOH suspension containing Compound 15-9 (69 mg, 0.185 mmol), and stirred under a hydrogen atmosphere at room temperature for 2 hours. The reaction solution was filtrated with Celite, and the filtrate was concentrated under reduced pressure, thereby obtaining a white solid, Compound 16-9 (26 mg, 49%).
1H-NMR (CD3OD) δ 7.74 (s, 1H), 7.36 (d, J=8.4 Hz, 2H), 7.11 (d, J=8.6 Hz, 2H), 2.45 (s, 3H), 2.29 (s, 3H), 2.24 (s, 3H), 2.18 (s, 3H) ppm.

<Example 17-19> Preparation of 1-(5-benzyloxy-3,4,6-trimethylpyridin-2-yl)-3-(4-methoxyphenyl)urea (15-10)

32 μl (0.248 mmol) of 4-methoxyphenyl isocyanate was added to 2 mL of a CH2Cl2 solution of Compound 7a (50 mg, 0.206 mmol), and stirred at room temperature for 10 hours. After the reaction, a solid precipitated from the reaction solution was filtrated, thereby obtaining a white solid, Compound 15-10 (75 mg, 93%).
1H-NMR (CDCl3) δ 11.88 (s, 1H), 7.55-7.33 (m, 7H), 6.89 (d, J=9.0 Hz, 2H), 4.79 (s, 2H), 3.80 (s, 3H), 2.46 (s, 3H), 2.29 (s, 6H) ppm.

<Example 17-20> Preparation of l-(5-hydroxy-3,4,6-trimethylpyridin-2-yl)-3-(4-methoxyphenyl)urea (16-10)

13 mg of 10% palladium on activated carbon was added to 3 mL of a MeOH suspension containing Compound 15-10 (63 mg, 0.161 mmol), and stirred under a hydrogen atmosphere at room temperature for 2 hours. The reaction solution was filtrated with Celite, and the filtrate was concentrated under reduced pressure, thereby obtaining a pale yellow solid, Compound 16-10 (47 mg, 97%).
1H-NMR (CD3OD) δ 7.42-7.35 (m, 2H), 6.93-6.85 (m, 2H), 3.78 (s, 3H), 2.43 (s, 3H), 2.24 (s, 3H), 2.18 (s, 3H) ppm.

<Example 17-21> Preparation of 1-(5-benzyloxy-3,4,6-trimethylpyridin-2-yl)-3-(4-(trifluoromethyl)phenyl)urea (15-11)

68 μl (0.206 mmol) of 4-trifluoromethylphenyl isocyanate was added to 2 mL of a CH2Cl2 solution of Compound 7a (50 mg, 0.206 mmol), and stirred at room temperature for 10 hours. After the reaction, a solid precipitated from the reaction solution was filtrated, thereby obtaining a white solid, Compound 15-11 (59 mg, 66%).
1H-NMR (CDCl3) δ 12.72 (s, 1H), 7.71 (d, J=8.6 Hz, 2H), 7.58 (d, J=8.7 Hz, 2H), 7.43 (ddd, J=8.7, 4.8, 2.5 Hz, 5H), 6.81 (brs, 1H), 4.79 (s, 2H), 2.50 (s, 3H), 2.28 (s, 3H), 2.19 (s, 3H) ppm.

<Example 17-22> Preparation of 1-(5-hydroxy-3,4,6-trimethylpyridin-2-yl)-3-(4-(trifluoromethyl)phenyl)urea (16-11)

9 mg of 10% palladium on activated carbon was added to 3 mL of a MeOH suspension containing Compound 15-11 (44 mg, 0.103 mmol), and stirred under a hydrogen atmosphere at room temperature for 2 hours. The reaction solution was filtrated with Celite, and the filtrate was concentrated under reduced pressure, thereby obtaining a white solid, Compound 16-11 (33 mg, 95%).
1H-NMR (CD3OD) δ 7.65 (dd, J=27.5, 8.7 Hz, 4H), 2.45 (s, 3H), 2.24 (s, 3H), 2.19 (s, 3H) ppm.

<Example 17-23> Preparation of 1-(5-benzyloxy-3,4,6-trimethylpyridin-2-yl)-3-(4-nitrophenyl)urea (15-12)

40 μl (0.247 mmol) of 4-nitrophenyl isocyanate was added to 2 mL of a CH2Cl2 solution of Compound 7a (50 mg, 0.206 mmol), and stirred at room temperature for 10 hours. After the reaction, a solid was filtrated, thereby obtaining a yellow solid, Compound 15-12 (75 mg, 89%).
1H-NMR ((CD3)2SO) δ 11.80 (s, 1H), 8.82 (s, 1H), 8.21 (t, J=7.9 Hz, 2H), 7.76 (t, J=9.3 Hz, 2H), 7.46 (dd, J=20.2, 7.4 Hz, 5H), 4.80 (s, 2H), 2.44 (s, 3H), 2.22 (s, 3H), 2.15 (s, 3H) ppm.

<Example 17-24> Preparation of 1-(5-hydroxy-3,4,6-trimethylpyridin-2-yl)-3-(4-nitrophenyl)urea (16-12)

15 mg of 10% palladium on activated carbon was added to 3 mL of a MeOH suspension containing Compound 15-12 (74 mg, 0.184 mmol), and stirred under a hydrogen atmosphere at room temperature for 2 hours. The reaction solution was filtrated with Celite, and the filtrate was concentrated under reduced pressure, thereby obtaining a white solid, Compound 16-12 (13.6 mg, 23%).
1H-NMR ((CD3)2SO) δ 11.03 (s, 1H), 8.33 (s, 1H), 7.94 (s, 1H), 7.15 (d, J=8.7 Hz, 2H), 6.52 (d, J=8.6 Hz, 2H), 2.36 (s, 3H), 2.12 (d, J=10.7 Hz, 6H) ppm.

<Example 17-25> Preparation of 1-(5-benzyloxy-3,4,6-trimethylpyridin-2-yl)-3-(4-(trifluoromethoxy)phenyl)urea (15-13)

31 μl (0.206 mmol) of 4-trifluoromethoxyphenyl isocyanate was added to 2 mL of a CH2Cl2 solution of Compound 7a (50 mg, 0.206 mmol), and stirred at room temperature for 10 hours. After the reaction, a solid precipitated from the reaction solution was filtered, thereby obtaining a white solid, Compound 15-13 (67 mg, 73%).

1H-NMR (CD3OD) δ 7.62 (d, J=8.9 Hz, 2H), 7.50-7.35 (m, 5H), 7.23 (d, J=8.2 Hz, 2H), 4.60 (s, 2H), 2.47 (s, 3H), 2.27 (s, 3H), 2.20 (s, 3H) ppm.

<Example 17-26> Preparation of 1-(5-hydroxy-3,4,6-trimethylpyridin-2-yl)-3-(4-(trifluoromethoxy)phenyl)urea (16-13)

13 mg of 10% palladium on activated carbon was added to 3 mL of a MeOH suspension containing Compound 15-13 (67 mg, 0.150 mmol), and stirred under a hydrogen atmosphere at room temperature for 2 hours. The reaction solution was filtrated with Celite, and the filtrate was concentrated under reduced pressure, thereby obtaining a white solid, Compound 16-13 (50 mg, 95%).

1H-NMR (CD3OD) δ 7.60 (d, 2H), 7.24 (d, J=9.1 Hz, 2H), 2.50 (s, 3H), 2.31 (s, 3H), 2.24 (s, 3H) ppm.

<Example 17-27> Preparation of 1-benzyl-3-(5-benzyloxy-3,4,6-trimethylpyridin-2-yl)urea (15-14)

43 μl (0.351 mmol) of benzyl isocyanate was added to 2 mL of a CH2Cl2 solution of Compound 7a (50 mg, 0.206 mmol), and stirred at room temperature for 10 hours. After the reaction, a solid precipitated from the reaction solution was filtered, thereby obtaining a white solid, Compound 15-14 (38 mg, 50%).

1H-NMR (CDCl3) δ 7.49-7.28 (m, 10H), 4.75 (s, 2H), 4.59 (d, J=5.5 Hz, 2H), 2.32 (s, 6H), 2.26 (s, 3H) ppm.

<Example 17-28> Preparation of 1-benzyl-3-(5-hydroxy-3,4,6-trimethylpyridin-2-yl)urea (16-14)

6 mg of 10% palladium on activated carbon was added to 3 mL of a MeOH suspension containing Compound 15-14 (31 mg, 0.082 mmol), and stirred under a hydrogen atmosphere at room temperature for 2 hours. The reaction solution was filtrated with Celite, and the filtrate was concentrated under reduced pressure, thereby obtaining a white solid, Compound 16-14 (23 mg, 100%).

1H-NMR ((CD3)2SO) δ 9.16 (s, 1H), 8.27 (brs, 1H), 7.93 (s, 1H), 7.37-7.23 (m, 5H), 4.40 (d, J=7.5 Hz, 2H), 2.24 (s, 3H), 2.12 (s, 3H), 2.06 (s, 3H) ppm.

<Example 17-29> Preparation of 1-(5-benzyloxy-3,4,6-trimethylpyridin-2-yl)-3-(4-isopropylphenyl)urea (15-15)

40 μl (0.248 mmol) of 4-isopropylphenyl isocyanate was added to 2 mL of a CH2Cl2 solution of Compound 7a (50 mg, 0.206 mmol), and stirred at room temperature for 10 hours. After the reaction, a solid was filtrated, thereby obtaining a white solid, Compound 15-15 (56 mg, 67%).

1H-NMR (CDCl3) δ 7.50 (d, J=8.5 Hz, 2H), 7.42 (s, 5H), 7.20 (d, J=8.5 Hz, 2H), 4.80 (s, 2H), 2.95-2.82 (m, 1H), 2.45 (s, 3H), 2.29 (s, 6H), 1.24 (d, J=6.9 Hz, 6H) ppm.

<Example 17-30> Preparation of 1-(5-hydroxy-3,4,6-trimethylpyridin-2-yl)-3-(4-isopropylphenyl)urea (16-15)

10 mg of 10% palladium on activated carbon was added to 3 mL of a MeOH suspension containing Compound 15-15 (49 mg, 0.121 mmol), and stirred under a hydrogen atmosphere at room temperature for 2 hours. The reaction solution was filtrated with Celite, and the filtrate was concentrated under reduced pressure, thereby obtaining a yellow solid, Compound 16-15 (38 mg, 100%).

1H-NMR ((CD3)2SO) δ 11.25 (s, 1H), 8.43 (s, 1H), 8.15 (s, 1H), 7.41 (d, J=8.5 Hz, 2H), 7.16 (d, J=8.5 Hz, 2H), 2.93-2.74 (m, 1H), 2.38 (s, 3H), 2.13 (d, J=10.1 Hz, 6H), 1.18 (d, J=6.9 Hz, 6H) ppm.

<Example 17-31> Preparation of N-((5-benzyloxy-3,4,6-trimethylpyridin-2-yl)carbamoyl)benzamide (15-16)

40 μl (0.309 mmol) of benzoyl isocyanate was added to 2 mL of a CH2Cl2 solution of Compound 7a (50 mg, 0.206 mmol), and stirred at room temperature for 10 hours. After the reaction, a solid precipitated from the reaction solution was filtered, thereby obtaining a white solid, Compound 15-16 (44 mg, 56%).

1H-NMR (CDCl3) δ 10.72 (brs, 1H), 8.87 (brs, 1H), 7.96 (d, J=6.3 Hz, 2H), 7.66-7.30 (m, 8H), 4.80 (s, 2H), 2.49 (s, 3H), 2.27 (d, J=5.5 Hz, 6H) ppm.

<Example 17-32> Preparation of N-((5-hydroxy-3,4,6-trimethylpyridin-2-yl)carbamoyl)benzamide (16-16)

9 mg of 10% palladium on activated carbon was added to 3 mL of a MeOH suspension containing Compound 15-16 (42 mg, 0.109 mmol), and stirred under a hydrogen atmosphere at room temperature for 2 hours. The reaction solution was filtrated with Celite, and the filtrate was concentrated under reduced pressure, thereby obtaining a white solid, Compound 16-16 (23 mg, 69%).

1H-NMR ((CD3)2SO) δ 11.06 (s, 1H), 10.26 (s, 1H), 8.61 (s, 1H), 8.02 (d, J=7.2 Hz, 2H), 7.60 (dt, J=29.5, 7.4 Hz, 3H), 2.31 (s, 3H), 2.16 (s, 3H), 2.08 (s, 3H) ppm.

Example 18. Preparation of pyridinol-thiourea derivatives

<Example 18-1> Preparation of 1-(5-benzyloxy-3,4,6-trimethylpyridin-2-yl)-3-butylthiourea (17-1a)

38.3 μl (0.318 mmol) of butyl isothiocyanate was added to 1.5 mL of an EtOH suspension containing Compound 7a (70 mg, 0.289 mmol), and stirred for 5 hours while heating at 60° C. The reaction solution was cooled to room temperature and concentrated under reduced pressure, and a residue was purified by column chromatography (EtAOc:Hex=1:5), thereby obtaining a pale yellow solid, Compound 17-1a (81 mg, 78%).

1H-NMR (CDCl3) δ 12.06 (s, 1H), 7.83 (s, 1H), 7.44-7.36 (m, 5H), 4.74 (s, 2H), 3.73 (dd, J=11.8, 6.7 Hz, 2H), 2.37 (s, 3H), 2.23 (s, 3H), 2.14 (s, 3H), 1.77-1.63 (m, 2H), 1.55-1.41 (m, 2H), 0.98 (t, J=7.3 Hz, 3H) ppm.

<Example 18-2> Preparation of 1-butyl-3-(5-hydroxy-3,4,6-trimethylpyridin-2-yl)thiourea (18-1)

79 mg (0.534 mmol) of pentamethylbenzene was added to 2 mL of a CH2Cl2 suspension containing Compound 17-1a (64 mg, 0.178 mmol), 0.36 mL of boron trichloride (1 M BCl3 in CH2Cl2) was slowly added thereto and stirred at 0° C. for 30 minutes. 2 mL of a CHCl3-MeOH solution (9:1) was added to the reaction solution, stirred for 30 minutes and then concentrated. A residue was purified by column chromatography (EtOAc:Hex=1:3→1:1), thereby obtaining a white solid, Compound 18-1 (28 mg, 61%).

1H-NMR (CDCl3) δ 11.89 (s, 1H), 7.76 (s, 1H), 4.74 (s, 1H), 3.72 (dd, J=11.9, 6.8 Hz, 2H), 2.38 (s, 3H), 2.23 (s, 3H), 2.14 (s, 3H), 1.73-1.67 (m, 2H), 1.56-1.39 (m, 2H), 0.98 (t, J=7.3 Hz, 3H) ppm.

<Example 18-3> Preparation of 1-(5-benzyloxy-3,4, 6-trimethylpyridin-2-yl)-3-isopropylthiourea (17-2a)

62 µL (0.578 mmol) of isopropyl isothiocyanate was added to 1.5 mL of a CH3CN suspension containing Compound 7a (70 mg, 0.289 mmol), and the resulting solution was stirred for 5 hours while refluxing. The reaction solution was cooled to room temperature and concentrated under reduced pressure, and a residue was purified by column chromatography (EtAOc:Hex=1:5→1:4), thereby obtaining a pale yellow solid, Compound 17-2a (88 mg, 89%).

1H-NMR (CDCl3) δ 12.06 (s, 1H), 7.76 (s, 1H), 7.46-7.36 (m, 5H), 4.75 (s, 2H), 4.53 (dq, J=13.2, 6.6 Hz, 1H), 2.39 (s, 3H), 2.23 (s, 3H), 2.14 (s, 3H), 1.35 (d, J=6.5 Hz, 6H) ppm.

<Example 18-4> Preparation of 1-(5-hydroxy-3,4,6-trimethylpyridin-2-yl)-3-isopropylthiourea (18-2)

114 mg (0.771 mmol) of pentamethylbenzene was added to 2 mL of a CH2Cl2 suspension containing Compound 17-2a (88 mg, 0.257 mmol), 0.52 mL of boron trichloride (1 M BCl3 in CH2Cl2) was slowly added thereto, and then the resulting solution was stirred at 0° C. for 12 hours. 2 mL of a CHCl3-MeOH solution (9:1) was added to the reaction solution, stirred for 30 minutes and concentrated. A residue was purified by column chromatography (EtOAc:Hex=1: 3→2:1) and then recrystallized, thereby obtaining a white solid, Compound 18-2 (61 mg, 94%).

1H-NMR ((CD3)2SO) δ 11.23 (s, 1H), 8.40 (s, 1H), 4.35 (dq, J=13.4, 6.6 Hz, 1H), 2.32 (s, 3H), 2.15 (s, 3H), 2.11 (s, 3H), 1.24 (d, J=6.5 Hz, 6H) ppm.

<Example 18-5> Preparation of 1-(5-benzyloxy-3,4, 6-trimethylpyridin-2-yl)-3-cyclohexylthiourea (17-3a)

42 µL (0.309 mmol) of cyclohexyl isothiocyanate was added to 0.5 mL of a CH3CN suspension containing Compound 7a (50 mg, 0.206 mmol), and stirred for 21 hours while refluxing. The reaction solution was cooled to room temperature and concentrated under reduced pressure, a residue was purified by column chromatography (EtAOc:Hex=1:4→1:3), thereby obtaining a pale yellow solid, Compound 17-3a (56 mg, 70%).

1H-NMR (CDCl3) δ 12.14-12.11 (m, 1H), 7.76 (s, 1H), 7.45-7.33 (m, 5H), 4.73 (s, 2H), 4.33-4.29 (m, 1H), 2.37 (s, 3H), 2.21 (s, 3H), 2.12 (s, 3H), 2.08-2.02 (m, 2H), 1.75-1.63 (m, 3H), 1.50-1.35 (m, 5H) ppm.

<Example 18-6> Preparation of 1-cyclohexyl-3-(5-hydroxy-3,4,6-trimethylpyridin-2-yl)thiourea (18-3)

43 mg (0.288 mmol) of pentamethylbenzene was added to 2 mL of a CH2Cl2 suspension containing Compound 17-3a (37 mg, 0.096 mmol), 0.19 mL of boron trichloride (1 M BCl3 in CH2Cl2) was slowly added thereto, and then the resulting solution was stirred at 0° C. for 3 hours. 1 mL of a CHCl3-MeOH solution (9:1) was added to the reaction solution, stirred for 30 minutes, and then concentrated. A residue was purified by column chromatography (CH2Cl2: MeOH=50:1) and then recrystallized, thereby obtaining a white solid, Compound 18-3 (15 mg, 54%).

1H-NMR ((CD3)2SO) δ 11.49-11.45 (m, 1H), 8.47 (s, 2H), 4.20 (s, 1H), 2.32 (s, 3H), 2.15 (s, 3H), 2.11 (s, 3H), 1.99-1.85 (m, 3H), 1.70-1.59 (m, 2H), 1.44-1.30 (m, 5H) ppm.

<Example 18-7> Preparation of 1-(5-benzyloxy-3,4, 6-trimethylpyridin-2-yl)-3-phenylthiourea (17-4a)

37 µL (0.309 mmol) of cyclohexyl isothiocyanate phenyl isothiocyanate was added to 1 mL of a CH3CN suspension containing Compound 7a (50 mg, 0.206 mmol), and stirred for 10 hours while refluxing. The reaction solution was cooled to room temperature and concentrated under reduced pressure, a residue was purified by column chromatography (EtAOc:Hex=1:5→1:1), thereby obtaining a pale yellow solid, Compound 17-4a (66 mg, 85%).

1H-NMR (CDCl3) δ 14.17 (s, 1H), 7.99 (s, 1H), 7.76 (d, J=7.9 Hz, 2H), 7.47-7.35 (m, 7H), 7.25-7.19 (m, 1H), 4.79 (s, 2H), 2.44 (s, 3H), 2.27 (s, 3H), 2.22 (s, 3H) ppm.

<Example 18-8> Preparation of 1-(5-hydroxy-3,4,6-trimethylpyridin-2-yl)-3-phenylthiourea (18-4)

29 mg (0.198 mmol) of pentamethylbenzene was added to 1 mL of a CH2Cl2 suspension containing Compound 17-4a (25 mg, 0.066 mmol), 0.13 mL of boron trichloride (1 M BCl3 in CH2Cl2) was slowly added thereto, and the resulting solution was stirred at 0° C. for 1 hour. 1 mL of a CHCl3-MeOH solution (9:1) was added to the reaction solution, stirred for 30 minutes, and then concentrated. A residue was purified by column chromatography (CH2Cl2: MeOH=40:1), thereby obtaining a white solid, Compound 18-4 (13 mg, 66%).

1H-NMR ((CD3)2SO) δ 13.12 (s, 1H), 9.12 (s, 1H), 7.73-7.65 (m, 2H), 7.41-7.32 (m, 2H), 7.21-7.12 (m, 1H), 2.38 (s, 3H), 2.17 (s, 6H) ppm.

<Example 18-9> Preparation of 1-(5-((tert-butyldiphenylsilyl)oxy)-3,4,6-trimethylpyridin-2-yl)-3-(p-tolyl)thiourea (17-5c)

42 mg (0.28 mmol) of p-tolyl isothiocyanate was added to 5 mL of an EtOH solution containing Compound 7c (110 mg, 0.28 mmol) and stirred at room temperature for 18 hours. The reaction solution was concentrated under reduced pressure, and a residue was recrystallized with EtOH, thereby obtaining a white solid, Compound 17-5c (110 mg, 73%).

MS m/z 540 [M+H]+.

<Example 18-10> Preparation of 1-(5-hydroxy-3,4, 6-trimethylpyridin-2-yl)-3-(p-tolyl)thiourea (18-5)

0.22 mL of a tetrabutylammonium fluoride (TBAF, 1.0 M in THF) solution was added to 2 mL of a THF solution containing Compound 17-5c (108 mg, 0.20 mmol), and stirred at room temperature for 1 hour. After 1 mL of saturated brine was added to the reaction solution, the reaction solution was diluted with 50 mL of EtOAc, an aqueous layer was isolated, and then the EtOAc solution was washed with saturated brine, dried with anhydrous MgSO4, filtered and concentrated under reduced pressure. A residue was purified by column chromatography (EtOAc:Hex=2:3), thereby obtaining a yellow solid, Compound 18-5 (38 mg, 63%).

1H-NMR ((CD3)2SO) δ 13.05 (s, 1H), 9.25 (s, 1H), 8.68 (s, 1H), 7.54 (d, J=8.4 Hz, 2H), 7.16 (d, J=8.4 Hz, 2H), 2.37 (s, 3H), 2.29 (s, 3H), 2.17 (s, 6H) ppm.

<Example 18-11> Preparation of 1-(5-benzyloxy-3,4,6-trimethylpyridin-2-yl)-3-(4-chlorophenyl)thiourea (17-6a)

53.9 mg (0.318 mmol) of 4-chlorophenyl isothiocyanate was added to 1.5 mL of an EtOH suspension containing Compound 7a (50 mg, 0.206 mmol), and stirred at 50° C. for 11 hours. The reaction solution was cooled to room temperature and concentrated under reduced pressure, a residue was purified by column chromatography (EtAOc:Hex=1:5), thereby obtaining a pale yellow solid, Compound 17-6a (98 mg, 82%).

1H-NMR (CDCl3) δ 14.28 (s, 1H), 7.99 (s, 1H), 7.70 (d, J=8.7 Hz, 2H), 7.45-7.31 (m, 7H), 4.76 (s, 2H), 2.42 (s, 3H), 2.25 (s, 3H), 2.19 (s, 3H) ppm.

<Example 18-12> Preparation of 1-(4-chlorophenyl)-3-(5-hydroxy-3,4,6-trimethylpyridin-2-yl)thiourea (18-6)

101 mg (0.678 mmol) of pentamethylbenzene was added to 1.5 mL of a CH2Cl2 suspension containing Compound 17-6a (93 mg, 0.226 mmol), 0.45 mL of boron trichloride (1 M BCl3 in CH2Cl2) was slowly added thereto, and the resulting solution was stirred at 0° C. for 1 hour. 2 mL of a CHCl3-MeOH solution (9:1) was added to the reaction solution, stirred for 30 minutes, and concentrated. A residue was purified by column chromatography (EtOAc:Hex=1:2→2:1) and recrystallized, thereby obtaining a white solid, Compound 18-6 (54 mg, 74%).

1H-NMR ((CD3)2SO) δ 12.99 (s, 1H), 9.18 (s, 1H), 8.64 (s, 1H), 7.73 (d, J=8.8 Hz, 2H), 7.41 (d, J=8.8 Hz, 2H), 2.38 (s, 3H), 2.17 (s, 6H) ppm.

<Example 18-13> Preparation of 1-(4-bromophenyl)-3-(5-((tert-butyldiphenylsilyl)oxy)-3,4,6-trimethylpyridin-2-yl)thiourea (17-7c)

57 mg (0.27 mmol) of 4-bromophenyl isothiocyanate was added to 5 mL of an EtOH solution containing Compound 7c (104 mg, 0.27 mmol), and stirred at room temperature for 18 hours. The reaction solution was concentrated under reduced pressure, and a residue was recrystallized with EtOH, thereby obtaining a white solid, Compound 17-7c (126 mg, 77%).

MS m/z 604 [M+H]+.

<Example 18-14> Preparation of 1-(4-bromophenyl)-3-(5-hydroxy-3,4,6-trimethylpyridin-2-yl)thiourea (18-7)

0.23 mL of a tetrabutylammonium fluoride (TBAF, 1.0 M in THF) solution was added to 2 mL of a THF solution containing Compound 17-7c (126 mg, 0.21 mmol), and stirred at room temperature for 1 hour. After 1 mL of saturated brine was added to the reaction solution, the reaction solution was diluted with 50 mL of EtOAc, an aqueous layer was isolated, and the EtOAc solution was washed with saturated brine, dried with anhydrous MgSO4, filtered and concentrated under reduced pressure. A residue was purified by column chromatography (EtOAc:Hex=2:3), thereby obtaining a yellow solid, Compound 18-7 (45 mg, 59%).

1H-NMR ((CD3)2SO) δ 12.96 (s, 1H), 9.00 (s, 1H), 8.65 (s, 1H), 7.67 (d, J=8.8 Hz, 2H), 7.53 (d, J=8.8 Hz, 2H), 2.37 (s, 3H), 2.17 (s, 6H) ppm.

<Example 18-15> Preparation of 1-(5-benzyloxy-3,4,6-trimethylpyridin-2-yl)-3-(3,4-dichlorophenyl)thiourea (17-8a)

70 μl (0.50 mmol) of 3,4-dichlorophenyl isothiocyanate was added to 5 mL of an EtOH solution containing Compound 7a (121 mg, 0.50 mmol), and stirred at room temperature for 18 hours. The reaction solution was concentrated under reduced pressure, and a residue was purified by column chromatography (EtOAc:Hex=1:4), thereby obtaining a white solid, Compound 17-8a (152 mg, 68%).

1H-NMR ((CD3)2SO) δ 13.00 (s, 1H), 8.19 (s, 1H), 7.64-7.60 (m, 1H), 7.57-7.54 (m, 1H), 7.51-7.48 (m, 2H), 7.46-7.36 (m, 4H), 4.80 (s, 2H), 2.41 (s, 3H), 2.23 (s, 3H), 2.20 (s, 3H) ppm.

<Example 18-16> Preparation of 1-(3,4-dichlorophenyl)-3-(5-methoxy-3,4,6-trimethylpyridin-2-yl)thiourea (17-8b)

24 μL (0.16 mmol) of 3,4-dichlorophenyl isothiocyanate was added to 2 mL of an EtOH solution containing Compound 7b (25 mg, 0.15 mmol), and stirred at room temperature 48 hours. The reaction solution was concentrated under reduced pressure, and a residue was purified by column chromatography (EtOAc:Hex=1:4), thereby obtaining a white solid, Compound 17-8b (30 mg, 54%).

1H-NMR ((CD3)2SO) δ 13.05 (s, 1H), 9.54 (s, 1H), 8.22 (s, 1H), 7.81 (d, J=8.0 Hz, 1H), 7.59 (t, J=7.6 Hz, 1H), 7.55-7.47 (m, 1H), 3.66 (s, 3H), 2.41 (s, 3H), 2.21 (s, 3H), 2.19 (s, 3H) ppm.

<Example 18-17> Preparation of 1-(5-((tert-butyldiphenylsilyl)oxy)-3,4,6-trimethylpyridin-2-yl)-3-(3,4-dichlorophenyl)thiourea (17-8c)

70 μL (0.50 mmol) of 3,4-dichlorophenyl isothiocyanate was added to 5 mL of an EtOH solution containing Compound 7c (196 mg, 0.50 mmol), and stirred at room temperature for 18 hours. The reaction solution was concentrated under reduced pressure, and a residue was recrystallized with EtOH, thereby obtaining a white solid, Compound 17-8c (238 mg, 80%).

1H-NMR ((CD3)2SO) δ 12.77 (s, 1H), 9.51 (s, 1H), 8.14 (d, J=2.0 Hz, 1H), 7.69-7.62 (m, 4H), 7.68-7.40 (m, 8H), 2.11 (s, 3H), 2.06 (s, 3H), 2.04 (s, 3H), 1.07 (s, 9H) ppm.

<Example 18-18> Preparation of 1-(3,4-dichlorophenyl)-3-(5-hydroxy-3,4,6-trimethylpyridin-2-yl)thiourea (18-8)

0.24 mL of a tetrabutylammonium fluoride (TBAF, 1.0 M in THF) solution was added to 2 mL of a THF solution containing Compound 17-8c (120 mg, 0.22 mmol), and stirred at room temperature for 1 hour. After 1 mL of saturated saline was added to the reaction solution, the reaction solution was diluted with 50 mL of EtOAc, an aqueous layer was isolated, the EtOAc solution was washed with saturated brine, dried with anhydrous MgSO4, filtered and concentrated under reduced pressure. A residue was purified by column chromatography (EtOAc:Hex=1:4), thereby obtaining a gray solid, Compound 18-8 (44 mg, 63%).

1H-NMR ((CD3)2SO) δ 12.81 (s, 1H), 9.45 (s, 1H), 8.71 (s, 1H), 8.19 (d, J=1.6 Hz, 1H), 7.63-7.52 (m, 2H), 2.37 (s, 3H), 2.16 (m, 6H) ppm.

<Example 18-19> Preparation of 1-(5-benzyloxy-3,4,6-trimethylpyridin-2-yl)-3-(3-(trifluoromethyl)phenyl)thiourea (17-9a)

76 μl (0.5 mmol) of 3-(trifluoromethyl)phenyl isothiocyanate was added to 5 mL of an EtOH solution containing Compound 7a (121 mg, 0.5 mmol), and stirred at room temperature for 18 hours. The reaction product was concentrated under reduced pressure, and a residue was purified by column chromatography (EtOAc:Hex=1:4), thereby obtaining a white solid, Compound 17-9a (91 mg, 76%).

1H-NMR ((CD3)2SO) δ 13.11 (s, 1H), 9.54 (s, 1H), 8.28 (s, 1H), 7.82 (d, J=7.7 Hz, 1H), 7.64-7.58 (m, 1H), 7.51 (m, 3H), 7.46-7.35 (m, 3H), 4.81 (s, 2H), 2.42 (s, 3H), 2.23 (s, 3H), 2.21 (s, 3H) ppm.

<Example 18-20> Preparation of 1-(5-Methoxy-3,4,6-trimethylpyridin-2-yl)-3-(3-(trifluoromethyl)phenyl)thiourea (17-9b)

24 μL (0.16 mmol) of 3-(trifluoromethyl)phenyl isothiocyanate was added to 2 mL of an EtOH solution containing Compound 7b (25 mg, 0.15 mmol), and stirred at room temperature for 48 hours. The reaction product was concentrated under reduced pressure, and a residue was purified by column chromatography (EtOAc:Hex=1:4), thereby obtaining a white solid, Compound 17-9b (30 mg, 54%).

1H-NMR ((CD3)2SO) δ 13.05 (s, 1H), 9.54 (s, 1H), 8.22 (s, 1H), 7.81 (d, J=8.0 Hz, 1H), 7.59 (t, J=7.6 Hz, 1H), 7.55-7.47 (m, 1H), 3.66 (s, 3H), 2.41 (s, 3H), 2.21 (s, 3H), 2.19 (s, 3H) ppm.

<Example 18-21> Preparation of 1-(5-((tert-Butyldiphenylsilyl)oxy)-3,4,6-trimethylpyridin-2-yl)-3-(3-(trifluoromethyl)phenyl)thiourea (17-9c)

76 μL (0.50 mmol) of 3-(trifluoromethyl)phenyl isothiocyanate was added to 5 mL of an EtOH solution containing Compound 7c (196 mg, 0.50 mmol), and stirred at 60° C. for 18 hours. The reaction product was concentrated under reduced pressure, and a residue was purified by column chromatography (EtOAc:Hex=1:9), thereby obtaining a white solid, Compound 17-9c (201 mg, 64%).

1H-NMR ((CD3)2SO) δ 12.85 (s, 1H), 9.49 (s, 1H), 8.23 (s, 1H), 7.77-7.71 (m, 1H), 7.70-7.63 (m, 4H), 7.58-7.41 (m, 8H), 2.13 (s, 3H), 2.07 (s, 3H), 2.04 (s, 3H), 1.08 (s, 9H) ppm.

<Example 18-22> Preparation of 1-(5-Hydroxy-3,4,6-trimethylpyridin-2-yl)-3-(3-(trifluoromethyl)phenyl)thiourea (18-9)

0.22 mL of a tetrabutylammonium fluoride (TBAF, 1.0 M in THF) solution was added to 2 mL of a THF solution containing Compound 17-9c (109 mg, 0.18 mmol), and stirred at room temperature for 1 hour. After 1 mL of saturated brine was added to the reaction solution, the reaction solution was diluted with 50 mL of EtOAc, an aqueous layer was isolated, and the EtOAc solution was washed with saturated brine, dried with anhydrous MgSO4, filtered and concentrated under reduced pressure. A residue was purified by column chromatography (EtOAc:Hex=3:7), thereby obtaining a white solid, Compound 18-9 (42 mg, 66%).

1H-NMR ((CD3)2SO) δ 12.85 (s, 1H), 9.44 (s, 1H), 8.71 (s, 1H), 8.27 (s, 1H), 7.79 (d, J=8.4 Hz, 1H), 7.62-7.57 (m, 1H), 7.49 (d, J=7.6 Hz, 1H), 2.38 (s, 3H), 2.17 (s, 6H) ppm.

<Example 18-23> Preparation of 1-(5-((tert-Butyldiphenylsilyl)oxy)-3,4,6-trimethylpyridin-2-yl)-3-(4-(trifluoromethyl)phenyl)thiourea (17-10c)

60 mg (0.30 mmol) of 4-(trifluoromethyl)phenyl isothiocyanate was added to 5 mL of an EtOH solution containing Compound 7c (113 mg, 0.29 mmol), and stirred at room temperature for 18 hours. The reaction solution was concentrated under reduced pressure, and a residue was recrystallized with EtOH, thereby obtaining a white solid, Compound 17-10c (140 mg, 81%).

MS m/z 594 [M+H]+.

<Example 18-24> Preparation of 1-(5-Hydroxy-3,4,6-trimethylpyridin-2-yl)-3-(4-(trifluoromethyl)phenyl)thiourea (18-10)

0.26 mL of a tetrabutylammonium fluoride (TBAF, 1.0 M in THF) solution was added to 3 mL of a THF solution containing Compound 17-10c (140 mg, 0.24 mmol), and stirred at room temperature for 1 hour. After 1 mL of saturated brine was added to the reaction solution, the aqueous solution was diluted with 50 mL of EtOAc, an aqueous layer was isolated, the EtOAc solution was washed with saturated brine, dried with anhydrous MgSO4, filtered and concentrated under reduced pressure. A residue was purified by column chromatography (EtOAc:Hex=2:3), thereby obtaining a gray solid, Compound 18-10 (54 mg, 64%).

1H-NMR ((CD3)2SO) δ 13.10 (s, 1H), 9.43 (s, 1H), 8.73 (s, 1H), 7.96 (d, J=8.4 Hz, 2H), 7.71 (d, J=8.4 Hz, 2H), 2.39 (s, 3H), 2.17 (s, 6H) ppm.

<Example 18-25> Preparation of 1-(5-((tert-Butyldiphenylsilyl)oxy)-3,4,6-trimethylpyridin-2-yl)-3-(4-nitrophenyl)thiourea (17-11c)

49 mg (0.27 mmol) of 4-nitrophenyl isothiocyanate was added to 5 mL of an EtOH solution containing Compound 7c (105 mg, 0.27 mmol), and stirred at room temperature for 18 hours. The reaction solution was concentrated under reduced pressure, and a residue was recrystallized with EtOH, thereby obtaining a white solid, Compound 17-11c (106 mg, 69%).

MS m/z 571 [M+H]+.

<Example 18-26> Preparation of 1-(5-Hydroxy-3,4,6-trimethylpyridin-2-yl)-3-(4-nitrophenyl)thiourea (18-11)

0.20 mL of a tetrabutylammonium fluoride (TBAF, 1.0 M in THF) solution was added to 2 mL of a THF solution containing Compound 17-11c (106 mg, 0.19 mmol), and stirred at room temperature for 1 hour. After 1 mL of saturated brine was added to the reaction solution, the reaction solution was diluted with 50 mL of EtOAc, an aqueous layer was isolated, and the EtOAc solution was washed with saturated brine, dried with anhydrous MgSO4, filtered and concentrated under reduced pressure. A residue was purified by column chromatography (EtOAc:Hex=2:3), thereby obtaining a yellow solid, Compound 18-11 (32 mg, 54%).

1H-NMR ((CD3)2SO) δ 13.11 (s, 1H), 9.67 (s, 1H), 8.76 (s, 1H), 8.22 (d, J=9.2 Hz, 2H), 8.04 (d, J=9.2 Hz, 2H), 2.40 (s, 3H), 2.17 (s, 6H) ppm.

<Example 18-27> Preparation of 1-(5-((tert-Butyl-diphenylsilyl)oxy)-3,4,6-trimethylpyridin-2-yl)-3-(4-methoxyphenyl)thiourea (17-12c)

83 μL (0.60 mmol) of 4-methoxyphenyl isothiocyanate was added to 6 mL of an EtOH solution containing Compound 7c (234 mg, 0.60 mmol), and stirred at 70° C. for 18 hours. The reaction product was concentrated under reduced pressure, and a residue was purified by column chromatography (EtOAc:Hex=1:9), thereby obtaining a white solid, Compound 17-12c (132 mg, 43%).

1H-NMR ((CD3)2SO) δ 12.79 (s, 1H), 9.06 (s, 1H), 7.69-7.63 (m, 4H), 7.51-7.40 (m, 8H), 6.90 (d, J=8.8 Hz, 2H), 3.74 (s, 3H), 2.21 (s, 3H), 2.04 (s, 6H), 1.07 (s, 9H) ppm.

<Example 18-28> Preparation of 1-(5-Hydroxy-3,4,6-trimethylpyridin-2-yl)-3-(4-methoxyphenyl)thiourea (18-12)

0.25 mL of a tetrabutylammonium fluoride (TBAF, 1.0 M in THF) solution was added to 2 mL of THF solution containing Compound 17-12c (107 mg, 0.21 mmol), and stirred at room temperature for 1 hour. After 1 mL of saturated saline was added to the reaction solution, the reaction solution was diluted with EtOAc (50 mL), an aqueous layer was isolated, and the EtOAc solution was washed with saturated brine, dried with anhydrous MgSO4, filtered and concentrated under reduced pressure. A residue was purified by column chromatography (EtOAc:Hex=2:3), thereby obtaining a white solid, Compound 18-12 (30 mg, 52%).

1H-NMR ((CD3)2SO) δ 12.88 (s, 1H), 8.99 (s, 1H), 8.64 (s, 1H), 7.52 (d, J=6.8 Hz, 2H), 6.93 (d, J=6.8 Hz, 2H), 3.75 (s, 3H), 2.36 (s, 3H), 2.17 (s, 6H) ppm.

<Example 18-29> Preparation of N-((5-benzyloxy-3,4,6-trimethylpyridin-2-yl)carbamothioyl)benzamide (17-13a)

42.7 μL (0.318 mmol) of benzoyl isothiocyanate was added to 1 mL of an EtOH suspension containing Compound 7a (70 mg, 0.289 mmol), and stirred at 50° C. for 10 hours. The reaction solution was cooled to room temperature and concentrated under reduced pressure, and a residue was purified by column chromatography (EtAOc:Hex=1:5→1:1), thereby obtaining a pale yellow solid, Compound 17-13a (117 mg, 99%).

1H-NMR (CDCl3) δ 12.17 (s, 1H), 9.14 (s, 1H), 7.89 (d, J=7.3 Hz, 2H), 7.68-7.60 (m, 1H), 7.58-7.51 (m, 2H), 7.48-7.37 (m, 5H), 4.85 (s, 2H), 2.52 (s, 3H), 2.28 (s, 3H), 2.26 (s, 3H) ppm.

<Example 18-30> Preparation of N-((5-Hydroxy-3,4,6-trimethylpyridin-2-yl)carbamothioyl)benzamide (18-13)

117 mg (0.792 mmol) of pentamethylbenzene was added to 2 mL of a CH2Cl2 suspension containing Compound 17-13a (107 mg, 0.264 mmol), 0.53 mL of boron trichloride (1 M BCl3 in CH2Cl2) was slowly added thereto, and then the resulting solution was stirred at 0° C. for 2 hours. 2 mL of a CHCl3-MeOH solution (9:1) was added to the reaction solution, stirred for 30 minutes and concentrated. A residue was purified by column chromatography (CHCl3:MeOH=40:1), thereby obtaining a white solid, Compound 18-13 (53 mg, 64%).

1H-NMR ((CD3)2SO) δ 12.12 (s, 1H), 11.52 (s, 1H), 8.69 (s, 1H), 7.99 (d, J=7.4 Hz, 2H), 7.67 (t, J=7.3 Hz, 1H), 7.54 (t, J=7.4 Hz, 2H), 2.33 (s, 3H), 2.16 (s, 3H), 2.11 (s, 3H) ppm.

Example 19. Preparation of pyridinol-carbamate derivatives

<Example 19-1> Preparation of methyl (5-benzyloxy-3,4,6-trimethylpyridin-2-yl)carbamate (19-1)

120 mg (0.864 mmol) of K2CO3 was added to 1 mL of an acetone suspension containing Compound 7a (70 mg, 0.289 mmol), and the reaction solution was cooled to 0° C. 112 μl (1.445 mmol) of methyl chloroformate was slowly added to the reaction solution, and stirred at room temperature for 24 hours. After the reaction solution was concentrated, a residue was washed with CH2Cl2 and water, and an aqueous layer was extracted with CH2Cl2 (3×30 mL). The CH2Cl2 solution was washed with saturated brine, dried with anhydrous MgSO4, filtered and concentrated under reduced pressure. A residue was purified by column chromatography (CH2Cl2:MeOH=30:1→20:1), thereby obtaining a pale yellow solid, Compound 19-1 (63 mg, 73%).

1H-NMR (CDCl3) δ 7.55-7.30 (m, 5H), 6.96 (s, 1H), 4.77 (s, 2H), 3.76 (s, 3H), 2.43 (s, 3H), 2.25 (s, 3H), 2.16 (s, 3H) ppm.

<Example 19-2> Preparation of methyl (5-hydroxy-3,4,6-trimethylpyridin-2-yl)carbamate (20-1)

12 mg of 10% palladium on activated carbon was added to 3 mL of a MeOH—CHCl3 suspension containing Compound 19-1 (55 mg, 0.184 mmol), and stirred under a hydrogen atmosphere at room temperature for 1 hour. The reaction solution was filtrated with Celite, and the filtrate was concentrated under reduced pressure. A residue was purified by column chromatography (CH2Cl2:MeOH=20:1→5:1), thereby obtaining a white solid, Compound 20-1 (37 mg, 96%).

1H-NMR ((CD3)2SO) δ 8.99 (s, 1H), 8.51 (s, 1H), 5.74 (s, 1H), 3.55 (s, 3H), 2.25 (s, 3H), 2.09 (s, 3H), 1.97 (s, 3H) ppm.

<Example 19-3> Preparation of butyl (5-benzyloxy-3,4,6-trimethylpyridin-2-yl)carbamate (19-2)

200 mg (1.445 mmol) of K2CO3 was added to 1 mL of an acetone suspension containing Compound 7a (70 mg, 0.289 mmol), and the reaction solution was cooled to 0° C. 183.8 μl (1.445 mmol) of butyl chloroformate was slowly added to the reaction solution, and stirred at room temperature for 24 hours. After the reaction solution was concentrated, a residue was diluted with CH2Cl2, and washed with a saturated NaHCO3 aqueous solution, water and saturated brine. The CH2Cl2 solution was dried with anhydrous MgSO4, filtered and concentrated under reduced pressure. A residue was purified by column chromatography (CH2Cl2:MeOH=30:1→20:1), thereby obtaining a white solid, Compound 19-2 (90 mg, 91%).

1H-NMR (CDCl3) δ 7.51-7.29 (m, 5H), 6.78 (s, 1H), 4.75 (s, 2H), 4.12 (t, J=6.6 Hz, 2H), 2.42 (s, 3H), 2.22 (s, 3H), 2.14 (s, 3H), 1.61 (dt, J=8.3, 5.6 Hz, 2H), 1.38 (dd, J=15.1, 7.4 Hz, 2H), 0.92 (t, J=7.3 Hz, 3H) ppm.

<Example 19-4> Preparation of butyl (5-hydroxy-3,4,6-trimethylpyridin-2-yl)carbamate (20-2)

16 mg of 10% palladium on activated carbon was added to 5 mL of a MeOH suspension containing Compound 19-2 (79 mg, 0.231 mmol), and stirred under a hydrogen atmosphere at room temperature for 1 hour. The reaction solution was filtrated with Celite, and the filtrate was concentrated under reduced pressure. A residue was dissolved in MeOH and filtrated with a membrane filter, and the filtrate was concentrated under reduced pressure, thereby obtaining a white solid, Compound 20-2 (54 mg, 92%).

1H-NMR ((CD3)2SO) δ 8.95 (s, 1H), 3.98 (t, J=6.5 Hz, 2H), 2.27 (s, 3H), 2.11 (s, 3H), 1.99 (s, 3H), 1.55 (dt, J=14.5, 6.6 Hz, 2H), 1.34 (dq, J=14.1, 7.1 Hz, 2H), 0.89 (t, J=7.3 Hz, 3H) ppm.

<Example 19-5> Preparation of isobutyl (5-benzyloxy-3,4,6-trimethylpyridin-2-yl)carbamate (19-3)

200 mg (1.445 mmol) of K2CO3 was added to 1 mL of an acetone suspension containing Compound 7a (70 mg, 0.289 mmol), and the reaction solution was cooled to 0° C. 187 μl (1.445 mmol) of isobutyl chloroformate was slowly added to the reaction solution. The reaction solution was stirred at room temperature for 23 hours, and further stirred at 50° C. for 4 hours. After the reaction solution was concentrated, a residue was diluted with CH2Cl2, and washed with a saturated NaHCO3 aqueous solution and a 6 M NaOH aqueous solution. An aqueous layer was extracted with CH2Cl2 (2×30 mL), and the CH2Cl2 solution was washed with saturated brine, dried with anhydrous MgSO4, filtered and concentrated under reduced pressure. A residue was purified by column chromatography (CH2Cl2:MeOH=40:1), thereby obtaining a yellow liquid, Compound 19-3 (94 mg, 93%).

1H-NMR (CDCl3) δ 7.46-7.30 (m, 5H), 4.75 (s, 2H), 3.91 (d, J=6.6 Hz, 2H), 2.42 (s, 3H), 2.21 (s, 3H), 2.14 (s, 3H), 1.94 (dt, J=13.4, 6.7 Hz, 1H), 0.92 (d, J=6.7 Hz, 6H) ppm.

<Example 19-6> Preparation of isobutyl (5-hydroxy-3,4,6-trimethylpyridin-2-yl)carbamate (20-3)

18 mg of 10% palladium on activated carbon was added to 5 mL of a MeOH suspension containing Compound 19-3 (91 mg, 0.266 mmol), and stirred under a hydrogen atmosphere at room temperature for 6 hours. The reaction solution was filtrated with Celite, and the filtrate was concentrated under reduced pressure. A residue was purified by column chromatography (CH2Cl2:MeOH=30:1→20:1), thereby obtaining a white solid, Compound 20-3 (34 mg, 50%).

1H-NMR ((CD3)2SO) δ 8.87 (s, 1H), 8.42 (s, 1H), 3.76 (d, J=6.6 Hz, 2H), 2.26 (s, 3H), 2.10 (s, 3H), 1.99 (s, 3H), 1.85 (td, J=13.3, 6.6 Hz, 1H), 0.87 (d, J=6.7 Hz, 6H) ppm.

<Example 19-7> Preparation of 2-chloroethyl (5-benzyloxy-3,4,6-trimethylpyridin-2-yl)carbamate (19-4)

200 mg (1.445 mmol) of K2CO3 was added to 1 mL of an acetone suspension containing Compound 7a (70 mg, 0.289 mmol), and then the reaction solution was cooled to 0° C. 149.2 μl (1.445 mmol) of 2-chloroethyl chloroformate was slowly added to the reaction solution, and stirred at room temperature for 9 hours.

After the reaction solution was concentrated, a residue was diluted with CH2Cl2 and washed with a saturated NaHCO3 aqueous solution and saturated brine. The CH2Cl2 solution was washed with saturated brine, dried with anhydrous MgSO4, filtered and concentrated under reduced pressure. A residue was purified by column chromatography (CH2Cl2:MeOH=50:1→30:1), thereby obtaining a white solid, Compound 19-4 (84 mg, 84%).

1H-NMR (CDCl3) δ 7.48-7.33 (m, 5H), 6.88 (s, 1H), 4.76 (s, 2H), 4.38 (t, J=5.8 Hz, 2H), 3.70 (t, J=6.0 Hz, 2H), 2.43 (s, 3H), 2.23 (s, 3H), 2.15 (s, 3H) ppm.

<Example 19-8> Preparation of 2-Chloroethyl (5-hydroxy-3,4,6-trimethylpyridin-2-yl)carbamate (20-4)

96 mg (0.645 mmol) of pentamethylbenzene was added to 2 mL of a CH2Cl2 suspension containing Compound 19-4 (75 mg, 0.215 mmol), 0.32 mL of boron trichloride (1 M BCl3 in CH2Cl2) was slowly added thereto, and the resulting solution was stirred at 0° C. for 30 minutes. 1 mL of a CHCl3-MeOH solution (9:1) was added to the reaction solution, stirred for 30 minutes, and then concentrated. A residue was purified by column chromatography (CHCl3:MeOH=30:1→10:1), thereby obtaining a white solid, Compound 20-4 (51 mg, 92%).

1H-NMR ((CD3)2SO) δ 9.11 (s, 1H), 8.48 (s, 1H), 4.31-4.21 (m, 2H), 3.86-3.76 (m, 2H), 2.28 (s, 3H), 2.12 (s, 3H), 2.02 (s, 3H) ppm.

<Example 19-9> Preparation of 2-methoxyethyl (5-benzyloxy-3,4,6-trimethylpyridin-2-yl)carbamate (19-5)

200 mg (1.445 mmol) of K2CO3 was added to 2 mL of an acetone suspension containing Compound 7a (70 mg, 0.289 mmol), and the reaction solution was cooled to 0° C. 168 μl (1.445 mmol) of 2-methoxyethyl chloroformate was slowly added to the reaction solution, and stirred at room temperature for 17 hours.

After the reaction solution was concentrated, a residue was diluted with CH2Cl2, and washed with a saturated NaHCO3 aqueous solution and saturated brine. The CH2Cl2 solution was washed with saturated brine, dried with anhydrous MgSO4, filtered and concentrated under reduced pressure. A residue was purified by column chromatography (CH2Cl2:MeOH=40:1), thereby obtaining a white solid, Compound 19-5 (72 mg, 72%).

1H-NMR (CDCl3) δ 7.49-7.35 (m, 5H), 6.94 (s, 1H), 4.77 (s, 2H), 4.35-4.26 (m, 2H), 3.67-3.58 (m, 2H), 3.41 (s, 3H), 2.44 (s, 3H), 2.24 (s, 3H), 2.16 (s, 3H) ppm.

<Example 19-10> Preparation of 2-methoxyethyl (5-hydroxy-3,4,6-trimethylpyridin-2-yl)carbamate (20-5)

19 mg of 10% palladium on activated carbon was added to 5 mL of a MeOH suspension containing Compound 19-5 (95 mg, 0.276 mmol), and stirred under a hydrogen atmosphere at room temperature for 1 hour. The reaction solution was filtrated with Celite, and the filtrate was concentrated under reduced pressure. A residue was dissolved in MeOH and filtrated with a membrane filter, and the filtrate was concentrated under reduced pressure, thereby obtaining a white solid, Compound 20-5 (70 mg, 99%).

1H-NMR ((CD3)2SO) δ 9.01 (s, 1H), 8.52 (s, 1H), 4.11 (dd, J=5.4, 3.9 Hz, 2H), 3.52 (dd, J=5.4, 4.0 Hz, 2H), 3.27 (s, 3H), 2.28 (s, 3H), 2.12 (s, 3H), 2.00 (s, 3H) ppm.

Example 20. Preparation of pyridinol-sulfonamide derivatives

<Example 20-1> Preparation of N-(5-benzyloxy-3,4,6-trimethylpyridin-2-yl)methanesulfonamide (21-1)

47.8 µl (0.618 mmol) of methanesulfonyl chloride was added to 2 mL of a pyridine suspension containing Compound 7a (50 mg, 0.206 mmol), and stirred at room temperature for 24 hours. After the reaction solution was concentrated, a residue was diluted with CH2Cl2, and washed with water and saturated brine. The CH2Cl2 solution was dried with anhydrous MgSO4, filtered and concentrated under reduced pressure. A residue was purified by column chromatography (CH2Cl2:MeOH=40:1→30:1), thereby obtaining a white solid, Compound 21-1 (34 mg, 52%).

1H-NMR (CDCl3) δ 7.43-7.37 (m, 5H), 4.72 (s, 2H), 3.20 (s, 3H), 2.30 (s, 3H), 2.21 (s, 3H), 2.13 (s, 3H) ppm.

<Example 20-2> Preparation of N-(5-hydroxy-3,4,6-trimethylpyridin-2-yl)methanesulfonamide (22-1)

5 mg of 10% palladium on activated carbon was added to 5 mL of a CH2Cl2-MeOH suspension containing Compound 21-1 (26 mg, 0.081 mmol), and stirred under a hydrogen atmosphere at room temperature for 1 hour. The reaction solution was filtrated with Celite, and the filtrate was concentrated under reduced pressure. A residue was dissolved in MeOH and filtrated with a membrane filter, and the filtrate was concentrated under reduced pressure, thereby obtaining a pale yellow solid, Compound 22-1 (19 mg, 100%).

1H-NMR ((CD3)2SO) δ 9.00 (br s, 1H), 3.20 (s, 3H), 2.30 (s, 3H), 2.10 (d, J=3.7 Hz, 6H) ppm.

<Example 20-3> Preparation of N-(5-benzyloxy-3,4,6-trimethylpyridin-2-yl)-4-methylbenzenesulfonamide (21-2)

86.5 mg (0.454 mmol) of tosyl chloride was added to 2 mL of a pyridine suspension containing Compound 7a (100 mg, 0.413 mmol), and stirred at room temperature for 2 hours. After the reaction solution was concentrated, a residue was diluted with CH2Cl2, and washed with water and saturated brine. The CH2Cl2 solution was dried with anhydrous MgSO4, filtered and concentrated under reduced pressure. A residue was purified by column chromatography (EtOAc:Hex=1:3), thereby obtaining a white solid, Compound 21-2 (82 mg, 50%).

1H-NMR (CDCl3) δ 7.81 (d, J=8.3 Hz, 2H), 7.39-7.35 (m, 5H), 7.22 (d, J=8.0 Hz, 2H), 4.70 (s, 2H), 2.37 (s, 3H), 2.23 (s, 3H), 2.19 (s, 3H), 2.14 (s, 3H) ppm.

<Example 20-4> Preparation of N-(5-hydroxy-3,4,6-trimethylpyridin-2-yl)-4-methylbenzenesulfonamide (22-2)

26 mg of 10% palladium on activated carbon was added to 10 mL of a MeOH suspension containing Compound 21-2 (130 mg, 0.328 mmol), and stirred under a hydrogen atmosphere at room temperature for 2 hours. The reaction solution was filtrated with Celite, and the filtrate was concentrated under reduced pressure. A residue was dissolved in MeOH, and filtrated with a membrane filter, and the filtrate was concentrated under reduced pressure, thereby obtaining a white solid, Compound 22-2 (186 mg, 85%).

1H-NMR ((CD3)2SO) δ 7.71 (d, J=8.3 Hz, 2H), 7.32 (d, J=8.0 Hz, 2H), 2.36 (s, 3H), 2.11 (s, 3H), 2.09 (s, 3H), 2.08 (s, 3H) ppm.

<Example 20-5> Preparation of N-(5-benzyloxy-3,4,6-trimethylpyridin-2-yl)-4-(trifluoromethyl)benzenesulfonamide (21-3)

227.1 mg (0.929 mmol) of 4-(trifluoromethyl)benzenesulfonyl chloride was added to 3 mL of a pyridine suspension containing Compound 7a (150 mg, 0.619 mmol), and stirred at room temperature for 24 hours. After the reaction solution was concentrated, a residue was diluted with CH2Cl2, and washed with water and a saturated NaHCO3 aqueous solution. An aqueous solution was extracted with CH2Cl2 (3×25 mL), and the CH2Cl2 solution was washed with saturated brine, dried with anhydrous MgSO4, filtered and concentrated under reduced pressure. A residue was purified by column chromatography (EtOAc:Hex=1:3), thereby obtaining a white solid, Compound 21-3 (231 mg, 83%).

1H-NMR (CDCl3) δ 8.05 (d, J=8.2 Hz, 2H), 7.68 (d, J=8.2 Hz, 2H), 7.41-7.31 (m, 5H), 4.72 (s, 2H), 2.25 (s, 3H), 2.22 (s, 3H), 2.14 (s, 3H) ppm.

<Example 20-6> Preparation of N-(5-hydroxy-3,4,6-trimethylpyridin-2-yl)-4-(trifluoromethyl)benzenesulfonamide (22-3)

23 mg of 10% palladium on activated carbon was added to 5 mL of a MeOH-THF suspension containing Compound 21-3 (146 mg, 0.324 mmol), and stirred under a hydrogen atmosphere at room temperature for 4 hours. The reaction solution was filtrated with Celite, and the filtrate was concentrated under reduced pressure. A residue was dissolved in MeOH, and filtrated with a membrane filter, and the filtrate was concentrated under reduced pressure, thereby obtaining a white solid, Compound 22-3 (182 mg, 98%).

1H-NMR ((CD3)2SO) δ 8.03 (d, J=8.3 Hz, 2H), 7.93 (d, J=8.4 Hz, 2H), 2.12 (s, 3H), 2.10 (s, 3H), 2.07 (s, 3H) ppm.

<Example 20-7> Preparation of N-(5-benzyloxy-3,4,6-trimethylpyridin-2-yl)-4-nitrobenzenesulfonamide (21-4)

219.5 mg (0.99 mmol) of 4-nitrobenzensulfonyl chloride was added to 3 mL of a pyridine suspension containing Compound 7a (200 mg, 0.825 mmol), and stirred at 70° C. for 48 hours. After the reaction solution was concentrated, a residue was diluted with CH2Cl2, and sequentially washed with water, a saturated NaHCO3 aqueous solution and saturated brine. The CH2Cl2 solution was dried with anhydrous MgSO4, filtered and concentrated under reduced pressure. A residue was purified by column chromatography (EtOAc:Hex=1:4), thereby obtaining a yellow solid, Compound 21-4 (233 mg, 66%).

1H-NMR (CDCl3) δ 11.94 (br s, 1H), 8.29-8.22 (m, 2H), 8.12-8.06 (m, 2H), 7.42-7.31 (m, 5H), 4.72 (s, 2H), 2.26 (s, 3H), 2.23 (s, 3H), 2.13 (s, 3H) ppm.

<Example 20-8> Preparation of N-(5-hydroxy-3,4,6-trimethylpyridin-2-yl)-4-nitrobenzenesulfonamide (22-4)

72.8 mg (0.491 mmol) of pentamethylbenzene was added to 1 mL of a CH2Cl2 suspension containing Compound 21-4 (70 mg, 0.164 mmol), 0.33 mL of boron trichloride (1 M BCl3 in CH2Cl2) was slowly added thereto, and the resulting solution was stirred at 0° C. for 30 minutes. 1 mL of a CHCl3-MeOH solution (9:1) was added to the reaction solution, stirred for 30 minutes and concentrated. A residue was purified by column chromatography (CHCl3:MeOH=30:1), thereby obtaining a yellow solid, Compound 22-4 (60 mg, 100%).

1H-NMR ((CD3)2SO) δ 10.11 (s, 1H), 8.60 (s, 1H), 8.39 (d, J=8.9 Hz, 2H), 8.08 (d, J=8.8 Hz, 2H), 2.13-2.07 (m, 9H) ppm.

<Example 20-9> Preparation of N-(5-benzyloxy-3,4,6-trimethylpyridin-2-yl)naphthalene-1-sulfonamide (21-5)

57.4 μL (0.412 mmol) of triethylamine and 70 mg (0.309 mmol) of 1-naphthalenesulfonyl chloride were added to 1 mL of a CH2Cl2 suspension containing Compound 7a (50 mg, 0.206 mmol), and stirred at room temperature for 70 hours. The reaction solution was diluted with CH2Cl2 and a saturated NaHCO3 aqueous solution, an aqueous layer was extracted with 3×30 mL of CH2Cl2, and the CH2Cl2 solution was washed with saturated brine, dried with anhydrous MgSO4, filtered and concentrated under reduced pressure. A residue was purified by column chromatography (EtOAc:Hex=1:15→1:2), thereby obtaining a pale yellow solid, Compound 21-5 (54 mg, 61%).

1H-NMR (CDCl3) δ 11.87 (s, 1H), 9.03 (d, J=8.6 Hz, 1H), 8.24 (d, J=7.2 Hz, 1H), 7.93 (d, J=8.2 Hz, 1H), 7.85 (d, J=8.1 Hz, 1H), 7.68-7.58 (m, 1H), 7.52 (t, J=7.4 Hz, 1H), 7.48-7.40 (m, 1H), 7.38-7.27 (m, 5H), 4.65 (s, 2H), 2.21 (s, 3H), 2.15 (s, 3H), 2.09 (s, 3H) ppm.

<Example 20-10> Preparation of N-(5-hydroxy-3,4,6-trimethylpyridin-2-yl)naphthalene-1-sulfonamide (22-5)

22 mg of 10% palladium on activated carbon was added to 5 mL of a MeOH suspension containing Compound 21-5 (109 mg, 0.252 mmol), and stirred under a hydrogen atmosphere at room temperature for 8 hours. The reaction solution was filtrated with Celite, and the filtrate was concentrated under reduced pressure. A residue was purified by column chromatography (EtOAc:Hex=1:2→1:1), thereby obtaining a pale yellow solid, Compound 22-5 (77 mg, 89%).

1H-NMR ((CD3)2SO) δ 8.75-8.65 (m, 1H), 8.22 (d, J=7.3 Hz, 1H), 8.14 (d, J=8.1 Hz, 1H), 8.06-8.01 (m, 1H), 7.63-7.57 (m, 3H), 2.07 (s, 3H), 2.06 (s, 3H), 1.96 (s, 3H) ppm.

Example 21. Preparation of pyridinol-sulfamide derivatives

<Example 21-1> Preparation of N-(5-benzyloxy-3,4,6-trimethylpyridin-2-yl)-2-oxooxazolidine-3-sulfonamide (23)

2 mL of a CH2Cl2 solution containing 360 μL (4.127 mmol) of chlorosulfonyl isocyanate was cooled to 0° C., and 277 μL (4.127 mmol) of 2-chloroethanol was added thereto, and the resulting solution was stirred at 0° C. for 2.5 hours. After 575 μL (4.127 mmol) of triethylamine was added to the reaction solution, 10 mL of a CH2Cl2 solution containing 500 mg (2.063 mmol) of Compound 7a was added dropwise at 0° C., and stirred at room temperature for 12 hours. The reaction solution was diluted with CH2Cl2, and washed with a saturated NaHCO3 aqueous solution. The CH2Cl2 solution was washed with saturated brine, dried with anhydrous MgSO4, filtered and concentrated under reduced pressure. A residue was purified by column chromatography (EtOAc:Hex=1:2→1:1), thereby obtaining a white solid, Compound 23 (592 mg, 73%).

1H-NMR (CDCl3) δ 7.38 (s, 5H), 4.75 (s, 2H), 4.29 (t, J=5.8 Hz, 2H), 3.61 (t, J=5.8 Hz, 2H), 2.32 (s, 3H), 2.24 (s, 3H), 2.16 (s, 3H) ppm.

<Example 21-2> Preparation of N-(5-benzyloxy-3,4,6-trimethyl-2-pyridinyl)-N'-(4-(tert-butyl)benzyl)sulfamide (24-1)

65 μL (0.488 mmol) of triethylamine and 55 μL (0.312 mmol) of tert-butylbenzylamine were added to 2 mL of 1,2-dichloroethane solution containing Compound 23 (61 mg, 0.159 mmol), and the reaction solution was stirred for 12 hours while refluxing. The reaction solution was diluted with CH2Cl2, and washed with a saturated NaHCO3 aqueous solution. The CH2Cl2 solution was washed with saturated brine, dried with anhydrous MgSO4, filtered and concentrated under reduced pressure. A residue was purified by column chromatography (EtOAc:Hex=1:5→1:3), thereby obtaining a pale yellow caramel, Compound 24-1 (26 mg, 35%).

1H-NMR (CDCl3) δ 7.45-7.36 (m, 5H), 7.31-7.26 (m, 2H), 7.23-7.16 (m, 2H), 5.76 (s, 1H), 4.71 (s, 2H), 4.20-4.18 (m, 2H), 2.34 (s, 3H), 2.19 (s, 3H), 2.03 (s, 3H), 1.26 (s, 9H) ppm.

<Example 21-3> Preparation of N-(5-hydroxy-3,4,6-trimethyl-2-pyridinyl)-N'-(4-(tert-butyl)benzyl)sulfamide (25-1)

6 mg of 10% palladium on activated carbon was added to 3 mL of a MeOH solution containing Compound 24-1 (26 mg, 0.056 mmol), and stirred under a hydrogen atmosphere at room temperature for 12 hours. The reaction solution was filtrated with Celite, and the filtrate was concentrated under reduced pressure. A residue was purified by column chromatography (EtOAc:Hex=1:2), thereby obtaining a pale yellow caramel, Compound 25-1 (8 mg, 38%).

1H-NMR (CDCl3) δ 7.35 (br s, 1H), 7.29-7.26 (m, 2H), 7.24-7.16 (m, 2H), 4.19 (s, 2H), 2.30 (s, 3H), 2.15 (s, 3H), 2.06 (s, 3H), 1.27 (s, 9H) ppm.

<Example 21-4> Preparation of N-(5-benzyloxy-3,4,6-trimethyl-2-pyridinyl)-N'-(4-chlorophenethyl)sulfamide (24-2)

54 μL (0.385 mmol) of triethylamine and 36 μL (0.257 mmol) of 2-(4-chlorophenyl)ethylamine were sequentially added to 1 mL of a CH3CN solution containing Compound 23 (50 mg, 0.128 mmol), and the reaction solution was stirred at 55° C. for 6 hours. After the reaction solution was concentrated, a residue was purified by column chromatography (EtOAc:Hex=1:5), thereby obtaining a pale yellow caramel, Compound 24-2 (14 mg, 24%).

1H-NMR (CDCl3) δ 7.49-7.39 (m, 5H), 7.29-7.27 (m, 2H), 7.16-7.12 (m, 2H), 4.73 (s, 2H), 3.39-3.29 (m, 2H), 2.89 (t, J=6.7 Hz, 2H), 2.23 (s, 3H), 2.20 (s, 3H), 2.11 (s, 3H) ppm.

<Example 21-5> Preparation of N-(5-hydroxy-3,4,6-trimethyl-2-pyridinyl)-N'-(4-chlorophenethyl)sulfamide (25-2)

13 mg (0.085 mmol) of pentamethylbenzene was added to 1 mL of a CH2Cl2 suspension containing Compound 24-2 (13 mg, 0.028 mmol), and 56 µL of boron trichloride (1 M BCl3 in CH2Cl2) was slowly added thereto and then stirred at 0° C. for 30 minutes. 1 mL of a CHCl3-MeOH solution (9:1) was added to the reaction solution and stirred for 30 minutes, and the reaction solution was concentrated. A residue was purified by column chromatography (CHCl3:MeOH=20:1), thereby obtaining a pale yellow caramel, Compound 25-2 (7 mg, 69%).
1H-NMR ((CD3)2SO) δ 7.37-7.30 (m, 2H), 7.27-7.19 (m, 2H), 3.13 (t, J=6.3 Hz, 2H), 2.77 (t, J=7.1 Hz, 2H), 2.13 (s, 3H), 2.07 (s, 3H), 2.06 (s, 3H) ppm.

Example 22. Preparation of pyridinol-alkoxide derivatives

<Example 22-1> Preparation of 5-benzyloxy-3,4,6-trimethylpyridin-2-ol (26)

2 g (8.253 mmol) of Compound 7a was dissolved in a mixed solvent of 100 mL of water and 3 mL of THF, and 1.1 mL (20.634 mmol) of a 10% H2SO4 aqueous solution was added thereto and cooled to 0° C. Here, 15 mL of an aqueous solution containing 285 mg of sodium nitrite (NaNO2, 4.127 mmol) was added thereto, slowly heated to room temperature while stirring for 2 hours. The reaction solution was diluted with CH2Cl2, and washed with a saturated NaHCO3 aqueous solution. An aqueous layer was extracted with CH2Cl2, the CH2Cl2 solution was washed with saturated brine, dried with anhydrous MgSO4, filtrated and concentrated under reduced pressure, thereby obtaining a yellow solid, Compound 26 (1.95 g, 98%).
1H-NMR (CDCl3) δ 7.43-7.32 (m, 5H), 4.69 (s, 2H), 2.23 (s, 3H), 2.17 (s, 3H), 2.09 (s, 3H) ppm.

<Example 22-2> Preparation of 2,5-Bis(benzyloxy)-3,4,6-trimethylpyridine (27-1)

23 mg of silver carbonate (Ag2CO3, 0.084 mmol) and 13 µL (0.105 mmol) of benzyl bromide were added to 2 mL of a THF-DMF (1:1) solution containing Compound 26 (17 mg, 0.070 mmol), and the reaction solution was stirred at room temperature for 20 hours. The reaction solution was filtrated with Celite, the filtrate was diluted with CH2Cl2 and water, and an aqueous layer was extracted with CH2Cl2. The CH2Cl2 solution was washed with water and saturated brine, dried with anhydrous MgSO4, filtered and concentrated under reduced pressure. A residue was purified by column chromatography (EtOAc:Hex=1:20), thereby obtaining a pale yellow liquid, Compound 27-1 (15 mg, 65%).
1H-NMR (CDCl3) δ 7.50-7.25 (m, 10H), 5.36 (s, 2H), 4.73 (s, 2H), 2.41 (s, 3H), 2.19 (s, 3H), 2.13 (s, 3H) ppm.

<Example 22-3> Preparation of 3,4,6-Trimethylpyridine-2,5-diol (28-1)

13 mg of 10% palladium on activated carbon was added to 2 mL of a MeOH solution containing Compound 27-1 (55 mg, 0.164 mmol) and stirred under a hydrogen atmosphere at room temperature for 1 hour. The reaction solution was filtrated with Celite, and the filtrate was concentrated under reduced pressure. A residue was dissolved in MeOH, and filtrated with a membrane filter, and the filtrate was concentrated under reduced pressure, thereby obtaining a yellow solid, Compound 28-1 (23 mg, 92%).
1H-NMR ((CD3)2SO) δ 2.08 (s, 3H), 2.03 (s, 3H), 1.90 (s, 3H) ppm.

<Example 22-4> Preparation of 3-benzyloxy-6-butoxy-2,4,5-trimethylpyridine (27-2)

136 mg of silver carbonate (Ag2CO3, 0.493 mmol) and 70 µL (0.617 mmol) of 1-iodobutane were added to 4 mL of a DMF solution containing Compound 26 (100 mg, 0.411 mmol), and the reaction solution was stirred at 40° C. for 2 hours.
The reaction solution was filtrated with Celite, and the filtrate was concentrated under reduced pressure. A residue was diluted with EtOAc, and washed with water and saturated brine. The EtOAc solution was dried with anhydrous MgSO4, filtered and concentrated under reduced pressure. A residue was purified by column chromatography (EtOAc:Hex=1:30), thereby obtaining a yellow liquid, Compound 27-2 (87 mg, 89%).
1H-NMR (CDCl3) δ 7.49-7.29 (m, 5H), 4.71 (s, 2H), 4.26 (t, J=6.5 Hz, 2H), 2.38 (s, 3H), 2.17 (s, 3H), 2.08 (s, 3H), 1.73 (dt, J=14.5, 6.7 Hz, 2H), 1.48 (dq, J=14.2, 7.2 Hz, 5H), 0.96 (t, J=7.3 Hz, 3H) ppm.

<Example 22-5> Preparation of 6-butoxy-2,4,5-trimethylpyridin-3-ol (28-2)

11 mg of 10% palladium on activated carbon was added to 2 mL of a MeOH solution containing Compound 27-2 (57 mg, 0.190 mmol), and stirred under a hydrogen atmosphere at room temperature for 1 hour. The reaction solution was filtrated with Celite, and the filtrate was concentrated under reduced pressure. A residue was dissolved in MeOH, and filtrated with a membrane filter, and the filtrate was concentrated under reduced pressure, thereby obtaining a yellow solid, Compound 28-2 (28 mg, 70%).
1H-NMR (CDCl3) δ 4.21 (t, J=6.5 Hz, 2H), 4.09 (s, 1H), 2.33 (s, 3H), 2.14 (s, 3H), 2.08 (s, 3H), 1.71 (dt, J=14.5, 6.6 Hz, 2H), 1.46 (dq, J=14.2, 7.2 Hz, 2H), 0.95 (t, J=7.3 Hz, 3H) ppm.

<Example 22-6> Preparation of 3-benzyloxy-2,4,5-trimethyl-6-(octyloxy)pyridine (27-3)

136 mg of silver carbonate (Ag2CO3, 0.493 mmol) and 111 µL (0.617 mmol) of 1-iodooctane were added to 4 mL of a DMF solution containing Compound 26 (100 mg, 0.411 mmol), and the reaction solution was stirred at 40° C. for 4 hours.
The reaction solution was filtrated with Celite, and the filtrate was concentrated under reduced pressure. A residue was diluted with EtOAc, and washed with water and saturated brine. The EtOAc solution was dried with anhydrous MgSO4, filtered and concentrated under reduced pressure. A residue was purified by column chromatography (EtOAc:Hex=1:30), thereby obtaining a yellow liquid, Compound 27-3 (131 mg, 90%).

1H-NMR (CDCl3) δ 7.48-7.29 (m, 5H), 4.71 (s, 2H), 4.25 (t, J=6.6 Hz, 2H), 2.38 (s, 3H), 2.17 (s, 3H), 2.08 (s, 3H), 1.79-1.63 (m, 2H), 1.47-1.25 (m, 10H), 0.88-0.83 (m, 3H) ppm.

<Example 22-7> Preparation of 2,4,5-Trimethyl-6-(octyloxy)pyridin-3-ol (28-3)

20 mg of 10% palladium on activated carbon was added to 20 mL of a MeOH solution containing Compound 27-3 (99 mg, 0.279 mmol), and stirred under a hydrogen atmosphere at room temperature for 1 hour. The reaction solution was filtrated with Celite, and the filtrate was concentrated under reduced pressure. A residue was dissolved in MeOH, filtrated with a membrane filter and concentrated under reduced pressure, thereby obtaining a yellow liquid, Compound 28-3 (70 mg, 95%).

1H-NMR (CDCl3) δ 4.20 (t, J=6.6 Hz, 2H), 4.04 (s, 1H), 2.33 (s, 3H), 2.14 (s, 3H), 2.08 (s, 3H), 1.76-1.68 (m, 2H), 1.44-1.25 (m, 10H), 0.92-0.85 (m, 3H) ppm.

<Example 22-8> Preparation of 3-benzyloxy-6-isopentyloxy-2,4,5-trimethylpyridine (27-4)

136 mg of silver carbonate (Ag2CO3, 0.493 mmol) and 71 μL (0.617 mmol) of 1-iodooctane were added to 4 mL of a DMF solution containing Compound 26 (100 mg, 0.411 mmol), and the reaction solution was stirred at 50° C. for 20 hours. The reaction solution was filtrated with Celite, and the filtrate was concentrated under reduced pressure. A residue was diluted with EtOAc, and washed with water and saturated brine. The EtOAc solution was dried with anhydrous MgSO4, filtered and concentrated under reduced pressure. A residue was purified by column chromatography (EtOAc:Hex=1:30), thereby obtaining a colorless liquid, Compound 27-4 (33 mg, 27%).

1H-NMR (CDCl3) δ 7.52-7.28 (m, 5H), 4.70 (s, 2H), 4.27 (t, J=6.6 Hz, 2H), 2.38 (s, 3H), 2.17 (s, 3H), 2.07 (s, 3H), 1.90-1.72 (m, 1H), 1.63 (q, J=6.7 Hz, 2H), 0.95 (d, J=6.6 Hz, 6H) ppm.

<Example 22-9> Preparation of 6-isopentyloxy-2,4,5-trimethylpyridin-3-ol (28-4)

14 mg of 10% palladium on activated carbon was added to 2 mL of a MeOH solution containing Compound 27-4 (72 mg, 0.230 mmol), and stirred under a hydrogen atmosphere at room temperature for 1 hour. The reaction solution was filtrated with Celite, and the filtrate was concentrated under reduced pressure. A residue was dissolved in MeOH, filtrated with a membrane filter and concentrated under reduced pressure, thereby obtaining a gray liquid, Compound 28-4 (40 mg, 78%).

1H-NMR (CDCl3) δ 4.24 (t, J=6.6 Hz, 2H), 4.08 (s, 1H), 2.33 (s, 3H), 2.14 (s, 3H), 2.07 (s, 3H), 1.78 (td, J=13.3, 6.6 Hz, 1H), 1.61 (dd, J=13.4, 6.7 Hz, 2H), 0.94 (d, J=6.6 Hz, 6H) ppm.

<Example 22-10> Preparation of 3-benzyloxy-6-cyclopentyloxy-2,4,5-trimethylpyridine (27-5)

136 mg of silver carbonate (Ag2CO3, 0.493 mmol) and 71 μL (0.617 mmol) of 1-iodocyclopentane were added to 4 mL of a DMF solution containing Compound 26 (100 mg, 0.411 mmol), and the reaction solution was stirred at 50° C. for 7 hours. The reaction solution was filtrated with Celite, and the filtrate was concentrated under reduced pressure. A residue was diluted with EtOAc, and washed with water and saturated brine. The EtOAc solution was dried with anhydrous MgSO4, filtered and concentrated under reduced pressure. A residue was purified by column chromatography (EtOAc:Hex=1:50), thereby obtaining a colorless liquid, Compound 27-5 (88 mg, 69%).

1H-NMR (CDCl3) δ 7.48-7.28 (m, 5H), 5.49-5.37 (m, 1H), 4.72 (s, 2H), 2.37 (s, 3H), 2.16 (s, 3H), 2.04 (s, 3H), 1.97-1.88 (m, 2H), 1.83-1.68 (m, 4H), 1.64-1.55 (m, 2H) ppm.

<Example 22-11> Preparation of 6-cyclopentyloxy-2,4,5-trimethylpyridin-3-ol (28-5)

13 mg of 10% palladium on activated carbon was added to 2 mL of a MeOH solution containing Compound 27-5 (63 mg, 0.202 mmol), and stirred under a hydrogen atmosphere at room temperature for 1 hour. The reaction solution was filtrated with Celite, and the filtrate was concentrated under reduced pressure. A residue was dissolved in MeOH, filtrated with a membrane filter and concentrated under reduced pressure, thereby obtaining a pale yellow solid, Compound 28-5 (39 mg, 87%).

1H-NMR (CDCl3) δ 5.39-5.35 (m, 1H), 4.05 (br s, 1H), 2.34 (s, 3H), 2.14 (s, 3H), 2.06 (s, 3H), 1.96-1.46 (m, 10H) ppm.

<Example 22-12> Preparation of 3-benzyloxy-2,4,5-trimethyl-6-(3-phenylpropoxy)pyridine (27-6)

136 mg of silver carbonate (Ag2CO3, 0.493 mmol) and 99 μL (0.617 mmol) of (3-iodopropyl)benzene were added to 4 mL of a DMF solution containing Compound 26 (100 mg, 0.411 mmol), and stirred at 50° C. for 4 hours. The reaction solution was filtrated with Celite, and the filtrate was concentrated under reduced pressure. A residue was diluted with EtOAc, and washed with water and saturated brine. The EtOAc solution was dried with anhydrous MgSO4, filtered and concentrated under reduced pressure. A residue was purified by column chromatography (EtOAc:Hex=1:50), thereby obtaining a colorless liquid, Compound 27-6 (101 mg, 68%).

1H-NMR (CDCl3) δ 7.49-7.26 (m, 6H), 7.24-7.11 (m, 4H), 4.72 (s, 2H), 4.32 (t, J=6.4 Hz, 2H), 2.85-2.73 (m, 2H), 2.37 (s, 3H), 2.18 (s, 3H), 2.13-2.01 (m, 5H) ppm.

<Example 22-13> Preparation of 2,4,5-Trimethyl-6-(3-phenylpropoxy)pyridin-3-ol (28-6)

15 mg of 10% palladium on activated carbon was added to 2 mL of a MeOH solution containing Compound 27-6 (77 mg, 0.202 mmol), and stirred under a hydrogen atmosphere at room temperature for 1 hour. The reaction solution was filtrated with Celite, and the filtrate was concentrated under reduced pressure. A residue was dissolved in MeOH, filtrated with a membrane filter and concentrated under reduced pressure, thereby obtaining a colorless liquid, Compound 28-6 (50 mg, 87%).

11H-NMR (CDCl3) δ 7.34-7.09 (m, 5H), 4.26 (t, J=6.3 Hz, 2H), 4.04 (s, 1H), 2.82-2.72 (m, 2H), 2.33 (s, 3H), 2.15 (s, 3H), 2.13-1.99 (m, 5H) ppm.

<Example 22-14> Preparation of 3-benzyloxy-6-((4-(tert-butyl)benzyl)oxy)-2,4,5-trimethylpyridine (27-7)

136 mg of silver carbonate (Ag2CO3, 0.493 mmol) and 113 μL (0.617 mmol) of 4-tert-butylbenzyl bromide were sequentially added to 4 mL of a DMF solution containing Compound 26 (100 mg, 0.411 mmol), and the reaction solution was stirred at 40° C. for 6 hours. The reaction solution was filtrated with Celite, and the filtrate was concentrated under reduced pressure. A residue was diluted with EtOAc, and washed with water and saturated brine. The EtOAc solution was dried with anhydrous MgSO4, filtered and concentrated under reduced pressure. A residue was purified by column chromatography (EtOAc:Hex=1:50), thereby obtaining a white solid, Compound 27-7 (143 mg, 89%).

1H-NMR (CDCl3) δ 7.48-7.30 (m, 9H), 5.34 (s, 2H), 4.73 (s, 2H), 2.41 (s, 3H), 2.18 (s, 3H), 2.12 (s, 3H), 1.32 (s, 9H) ppm.

<Experimental Example 1> Test for Inhibitory Activity Against TNF-α-Induced Adhesion of Monocytes to Intestinal Epithelial Cells <Test Method>

HT-29 human colorectal cancer-derived epithelial cells and U937 human-derived monocytic cells were cultured in an RPMI 1640 medium containing 10% FBS and 1% penicillin/streptomycin (PS) at 37° C. under a condition of 5% CO2, and when the cells were grown to 80% or more in a culture flask, they were subcultured in a ratio of 1:3 to be used in this test. The HT-29 cells were cultured in a 24-well plate at a concentration of 2×105 cells/cm2, and then the medium only containing 1% FBS and 1% PS was pretreated with a test drug for 1 hour. Afterward, BCECF-loaded U937 cells by being treated with 10 μg/mL of BCECF-AM at 37° C. for 30 minutes and 10 ng/mL of TNF-α reacted with the HT-29 cells previously treated with the test drug at 37° C. for 3 hours. After the reaction, the medium was removed, and then the cells were washed with PBS twice to remove U937 cells that were not adhered. In a subsequent step, for cell lysis, 0.1% Triton X-100 (0.1 M Tris) was treated to allow a reaction at room temperature for 30 minutes, and then fluorescence was measured using a Fluostar optima microplate reader (BMG LABTECH, Germany) to quantify the cells (Carvalho et al., 1996; Thapa et al., 2008).

Carvalho, D., Savage, C. O., Black, C. M. and Pearson, J. D., IgG antiendothelial cell autoantibodies from scleroderma patients induce leukocyte adhesion to human vascular endothelial cells in vitro. Induction of adhesion molecule expression and involvement of endothelium-derived cytokines. J. Clin. Invest. 97, 111-119 (1996).

Thapa, D., Lee, J. S., Park, S. Y., Bae, Y. H., Bae, S. K., Kwon, J. B., Kim, K. J., Kwak, M. K., Park, Y. J., Choi, H. G. and Kim, J. A., Clotrimazole Ameliorates Intestinal Inflammation and Abnormal Angiogenesis by Inhibiting Interleukin-8 Expression through a Nuclear Factor-kB-Dependent Manner. J. Pharmacol. Exp. Ther. 327, 353-364 (2008).

TABLE 7

| Compound | Inhibitory activity (%) |
|---|---|
| 5-ASA | 3.8 |
| GLPG | 30.9 |
| 16-1 | 18.2 |
| 16-2 | 79.3 |
| 16-3 | 7.7 |
| 16-4 | 34.3 |
| 16-5 | 20.2 |
| 16-6 | 17.5 |

TABLE 7-continued

| Compound | Inhibitory activity (%) |
|---|---|
| 16-7 | 14.6 |
| 16-8 | 17.2 |
| 16-9 | 20.1 |
| 16-10 | 12.6 |
| 16-11 | 52.7 |
| 16-12 | 79.0 |
| 16-13 | 12.6 |
| 16-14 | 4.9 |
| 16-15 | 11.5 |
| 16-16 | 34.2 |
| 17-8a | 17.3 |
| 17-8b | 39.5 |
| 17-8c | 18.8 |
| 17-9a | 19.6 |
| 17-9b | 39.0 |
| 17-9c | 25.9 |
| 17-12c | 16.0 |
| 18-1 | −19.9 |
| 18-2 | 63.0 |
| 18-3 | 65.9 |
| 18-4 | 49.7 |
| 18-5 | 19.2 |
| 18-6 | 51.6 |
| 18-7 | 27.8 |
| 18-8 | 87.2 |
| 18-9 | 93.0 |
| 18-10 | 77.4 |
| 18-11 | 76.0 |
| 18-12 | 13.3 |
| 18-13 | 66.3 |
| 20-1 | 9.8 |
| 20-2 | 26.9 |
| 20-3 | 6.0 |
| 20-4 | −1.5 |
| 20-5 | −22.5 |
| 22-1 | 18.7 |
| 22-2 | 42.1 |
| 22-3 | 87.3 |
| 22-4 | −2.3 |
| 22-5 | 80.6 |
| 28-1 | 66.6 |
| 28-2 | 48.2 |
| 28-3 | 30.4 |
| 28-4 | 33.2 |
| 28-5 | 28.8 |
| 28-6 | 58.3 |

A result of investigating the inhibitory activity of 1 μM of the test drug involved in the adhesion of the TNF-α-induced intestinal epithelial cells (HT-29) and the monocytic cells (U937) is shown in Table 7. Currently, in the clinic, 5-ASA (positive control), which is an active metabolite of a drug used in IBD treatment, that is, sulfasalazine, has an inhibition rate of 3.8% and is hardly effective at a concentration of 1 μM, and a GLPG compound, which is in clinical trials for developing an IBD therapeutic agent at Galapagos, showed an inhibition rate of 30.9%. On the other hand, a pyridinol derivative 18-9 compound had an inhibition rate of 93% and showed very excellent activity. Compound 22-3 showed an inhibition rate of 87.3%, and Compound 18-8 showed an inhibition rate of 87.2%. Compounds exhibiting an inhibition rate of 50% or more are listed in the order of increasing inhibitory activity as follows: Compounds 18-9>22-3>18-8>22-5>16-12>18-10>16-2>18-11>28-1>18-13>18-3>18-2>28-6>18-6. It was confirmed that, except some compounds, Compounds 18-1, 20-4 and 20-5, which had an inhibitory activity lower than that when a solvent was treated, other compounds had superior inhibitory activity to 5-ASA.

TABLE 8

| Compound | 1 µM concentration inhibitory activity | IC$_{50}$ |
| --- | --- | --- |
| 5-ASA | 3.8% | 18.1 mM |
| 16-2 | 76.3% | 0.41 µM |
| 22-3 | 87.3% | 0.32 µM |
| 22-5 | 80.6% | 0.23 µM |

Results of calculating the adhesion inhibition IC50 for three types of compounds having excellent inhibitory activity against TNF-α-induced intestine epithelial cell-monocyte adhesion are shown in Table 8. While the IC50 of 4-ASA used as a control drug was 18.1 mM, the IC50 of Compounds 16-2, 22-3 and 22-5 were 0.41 µM, 0.32 µM and 0.23 µM, respectively, which showed tens of thousand times more activity than 5-ASA.

<Experimental Example 2> Test for In Vivo Efficacy of Oral Administration of Compound in Animal Models with TNBS-Induced Inflammatory Bowel Disease <Test Method>

7 to 8-week-old Sprague Dawley rats were purchased from Orient Bio Korea, and after stabilization with typical solid feed for 3 days, were used as animals for the experiment. The animals were freely supplied with feed and water during the experiment, and a cage was maintained at a temperature of 25±1° C. and a relative humidity of 50±10%. Lighting was adjusted to a 12-hour light-dark cycle using an automatic lightening system. In regard to experimental groups, there were 5 groups each consisting of 6 rats having an average weight of 180±10 g (a control group, a group administered TNBS only, a group administered TNBS+300 mg/kg of sulfasalazine, a group administered TNBS+10 mg/kg of GLPG, and a group administered TNBS+1 mg/kg of test drug), which were divided according to a randomized block design.

(1) Induction of Colitis by Rectal Administration of TNBS

After rats that had been fasting for 24 hours were anesthetized with diethyl ether, a 1 mL syringe connected with a polyethylene catheter was used to slowly inject 0.8 mL of 5% TNBS diluted with 50v/v % ethanol into the lumen of a colon, and then the rats turned upside down and kept upright for 60 seconds to prevent the leakage of 5% TNBS from the anus. In the control group, only a vehicle [50 v/v % ethanol] was injected in the same manner as in the other groups (Thapa et al., 2008).

(2) Drug Administration

To examine a drug effect, for 5 days from the day following the TNBS treatment, a drug was administered at a predetermined time every day.

(3) Body Weight Observation

A change in the body weights of the rats was observed using a digital mass meter from the fasting stage to the end of the TNBS administration and drug administration processes.

(4) Measurement of Bowel Weight

The colon of each rat was extracted and tissue 5 to 6 cm from the anus was cut into 1-cm pieces, and then the weight of the tissue was measured.

TABLE 9

| Compound | Dosage | Bowel weight recovery rate (%) | Body weight recovery rate (%) |
| --- | --- | --- | --- |
| Sulfasalazine | 300 mg/kg | 69.6 | 50.5 |
| GLPG | 10 mg/kg | 71.8 | 50.0 |
| 16-2 | 1 mg/kg | 81.6 | 69.0 |
| 18-2 | 1 mg/kg | 81.6 | 72.0 |
| 18-8 | 1 mg/kg | 84.6 | 72.4 |
| 18-9 | 1 mg/kg | 87.2 | 74.9 |
| 18-13 | 1 mg/kg | 94.9 | 93.8 |
| 22-3 | 1 mg/kg | 50.3 | 25.0 |

<Effect of Oral Administration of Compound on TNBS-Induced Colitis>

In a test for inhibiting in vitro adhesion, in vivo colitis inhibitory activity was measured for the compounds having excellent activity, and is shown in Table 9.

A. Change in Body Weight

In a colitis model in which intestinal inflammation was induced in a rat having a body weight of 180 to 190 g with 5% TNBS, a change in the body weight were observed for 5 days at a predetermined time based on the body weight before the TNBS treatment, and therefore, in the vehicle-treated control group, the body weight kept increasing, and in the group treated with TNBS only, the body weight kept decreasing, but slightly recovered from the 5th day. However, it was still considerably smaller than the body weight of the normal group. In the group treated with 300 mg/kg of sulfasalazine as the positive control group, the body weight slowly recovered, but was still smaller than that of the vehicle-treated control group. However, compared to the group treated with TNBS only, the body weight considerably increased, and thus a body weight recovery rate was 50.5%. Even in the group treated with 10 mg/kg of GLPG, the body weight recovery rate was 50%. Although 1 mg/kg of each pyridinol compound was administered, the recovery rate was still 93.8% to 25.3%. The compounds are listed in the order of increasing body weight recovery rate as follows: Compounds 18-13>18-9>18-8>18-2, 16-2>22-3.

B. Morphology Observation

After 5-day drug administration, the colon was extracted and observed with the naked eye, the colon of the TNBS-treated rat showed edema and hyperemia compared with the control group, and the edema and congestion of the appendix and the adhesion of bowel tissue were also exhibited. In the group treated with 300 mg/kg of sulfasalazine as the positive control, visual symptoms, adhesion between other organs or intestinal hyperemia was also considerably inhibited, and the pyridinol compound-administered group was more improved in symptoms than the group treated with 300 mg/kg of sulfasalazine.

C. Measurement of Bowel Weight

The colon of a rat was extracted, and the body weight of tissue present 5 to 6 cm apart from the anus was measured. As a result, compared with the vehicle-treated control group, the group treated with TNBS only was significantly increased in the bowel weight due to edema, and the group treated with 300 mg/kg of sulfasalazine as the positive control group showed a bowel tissue weight recovery ratio of 69.6%.

The group treated with 10 mg/kg of GLPG also showed a bowel tissue weight recovery ratio of 71.8%. Although 1 mg/kg of each pyridinol compound was administered, the recovery rate was still 94.9% to 50.3%. The compounds are listed in the order of increasing bowel tissue weight recovery rate as follows: Compounds 18-13>18-9>18-8>18-2, 16-2>22-3.

<Experimental Example 3> Cytotoxicity Test

The human colorectal cancer cell line HT-29 and the monocytic blood cancer-derived cell line U937 were cultured in a RPMI 1640 medium containing 10% FBS and 1% penicillin/streptomycin (PS) at 37° C. under a condition of 5% CO2, and when the cells used herein were grown to 80% or more, they were subcultured at a ratio of 1:3.

Each type of cells were cultured in a 96 well plate at a concentration of 1×105 cells/cm2, treated with a test compound by concentration in a medium only containing 1% FBS and 1% PS at 37° C. under a condition of 5% CO2 for 48 hours and reacted with 5 mg/mL of a 3-[4,5-dimethyl-thiazol-2-yl]-2,5-diphenyltetrazolium bromide (MTT) reagent for 4 hours, and then the medium was completely removed, the cells were treated with DMSO, formazan crystals were dissolved for 30 minutes, and then absorbance was measured at 540 nm.

TABLE 10

Cell viability (% of control)

HT-29 (48 h)
Compound Concentration (μM)

| Compounds | 0 | 0.01 | 0.1 | 1 | 10 | 100 | IC$_{50}$ (μM) |
|---|---|---|---|---|---|---|---|
| 5-Fluorouracil | 100 ± 3.6 | 85.5 ± 3.9 | 77.6 ± 4.6 | 61.9 ± 4.2 | 48.3 ± 2.0 | 36.0 ± 2.5 | 7.6 |
| Doxorubicin | 100 ± 3.6 | 69.9 ± 1.1 | 66.9 ± 3.3 | 58.2 ± 6.4 | 53.2 ± 5.1 | 35.7 ± 2.0 | 12.9 |
| 16-1 | 100 ± 3.1 | 94.9 ± 6.5 | 84.4 ± 4.2 | 84.4 ± 4.2 | 70.9 ± 6.2 | 42.8 ± 2.7 | 64.6 |
| 16-2 | 100 ± 3.1 | 103.3 ± 1.9 | 102.8 ± 1.6 | 102.9 ± 3.5 | 93.4 ± 7.2 | 65.2 ± 6.6 | >100 |
| 16-3 | 100 ± 2.0 | 104.4 ± 6.1 | 102.5 ± 6.4 | 103.0 ± 11.1 | 89.3 ± 4.8 | 69.2 ± 6.1 | >100 |
| 16-4 | 100 ± 5.8 | 76.6 ± 6.9 | 76.8 ± 5.0 | 74.7 ± 6.0 | 62.1 ± 2.9 | 43.6 ± 1.8 | 34.7 |
| 16-5 | 100 ± 2.0 | 105.1 ± 1.1 | 94.3 ± 2.1 | 78.6 ± 10.1 | 73.4 ± 5.6 | 76.7 ± 1.1 | >100 |
| 16-6 | 100 ± 5.3 | 90.0 ± 3.5 | 85.4 ± 0.9 | 76.0 ± 7.2 | 77.9 ± 3.5 | 53.6 ± 2.5 | >100 |
| 18-1 | 100 ± 5.0 | 93.5 ± 3.4 | 95.2 ± 1.7 | 96.9 ± 1.4 | 96.5 ± 2.3 | 60.3 ± 0.5 | >100 |
| 18-2 | 100 ± 1.5 | 87.6 ± 4.8 | 87.3 ± 2.1 | 88.4 ± 4.2 | 87.6 ± 5.3 | 88.6 ± 1.3 | >100 |
| 18-3 | 100 ± 4.4 | 90.9 ± 5.1 | 80.5 ± 10.4 | 66.8 ± 6.2 | 67.0 ± 5.0 | 51.3 ± 6.7 | >100 |
| 18-4 | 100 ± 5.0 | 96.6 ± 2.1 | 97.0 ± 4.4 | 99.0 ± 5.0 | 96.6 ± 2.4 | 76.0 ± 4.9 | >100 |
| 18-6 | 100 ± 1.5 | 95.2 ± 3.2 | 86.6 ± 4.9 | 83.6 ± 3.3 | 72.8 ± 2.8 | 65.3 ± 1.9 | >100 |
| 18-13 | 100 ± 4.4 | 78.8 ± 3.3 | 75.4 ± 1.3 | 75.4 ± 4.1 | 57.9 ± 5.8 | 36.4 ± 6.1 | 19.1 |
| 20-1 | 100 ± 3.8 | 89.7 ± 6.3 | 84.9 ± 1.9 | 85.0 ± 3.4 | 82.6 ± 1.3 | 73.7 ± 4.5 | >100 |
| 20-2 | 100 ± 0.5 | 102.1 ± 1.4 | 101.9 ± 3.2 | 98.1 ± 3.4 | 98.3 ± 3.8 | 67.6 ± 1.9 | >100 |
| 20-3 | 100 ± 0.5 | 100.8 ± 1.9 | 91.0 ± 3.6 | 93.3 ± 4.7 | 83.7 ± 3.3 | 71.2 ± 3.4 | >100 |
| 20-4 | 100 ± 2.8 | 97.4 ± 2.2 | 94.7 ± 3.3 | 88.6 ± 2.2 | 90.2 ± 5.3 | 86.7 ± 3.1 | >100 |
| 20-5 | 100 ± 2.8 | 89.7 ± 1.2 | 83.2 ± 2.6 | 84.7 ± 1.6 | 85.5 ± 3.3 | 82.3 ± 1.1 | >100 |
| 22-1 | 100 ± 0.8 | 87.6 ± 3.3 | 75.7 ± 8.2 | 76.1 ± 3.6 | 63.5 ± 1.8 | 43.0 ± 1.9 | 50.1 |
| 22-2 | 100 ± 0.8 | 77.1 ± 3.0 | 76.9 ± 4.0 | 73.8 ± 5.8 | 71.5 ± 4.6 | 62.8 ± 0.5 | >100 |
| 22-3 | 100 ± 0.5 | 92.5 ± 1.5 | 95.0 ± 0.9 | 89.3 ± 4.7 | 91.8 ± 1.8 | 72.6 ± 3.2 | >100 |
| 22-4 | 100 ± 3.8 | 96.6 ± 1.3 | 97.8 ± 2.4 | 96.3 ± 1.7 | 85.4 ± 6.7 | 64.8 ± 7.1 | >100 |
| 22-5 | 100 ± 0.5 | 95.2 ± 3.3 | 86.7 ± 6.5 | 87.8 ± 3.2 | 89.1 ± 3.5 | 88.8 ± 1.2 | >100 |

TABLE 11

Cell viability (% of control)

U937 (48 h)
Compound Concentration (μM)

| Compounds | 0 | 0.01 | 0.1 | 1 | 10 | 100 | IC$_{50}$ (μM) |
|---|---|---|---|---|---|---|---|
| 5-Fluorouracil | 100 ± 4.0 | 93.0 ± 2.7 | 89.8 ± 2.7 | 75.7 ± 0.6 | 71.3 ± 1.7 | 59.7 ± 0.2 | >100 |
| Doxorubicin | 100 ± 1.0 | 93.6 ± 1.8 | 91.4 ± 3.3 | 42.2 ± 1.3 | 38.3 ± 0.6 | 33.2 ± 1.3 | 0.6 |
| 16-1 | 100 ± 0.7 | 89.1 ± 3.5 | 88.4 ± 3.5 | 90.0 ± 4.8 | 75.2 ± 0.9 | 44.2 ± 0.7 | 15.4 |
| 16-2 | 100 ± 0.7 | 89.9 ± 2.6 | 88.9 ± 1.9 | 87.1 ± 2.0 | 81.7 ± 2.0 | 78.0 ± 0.6 | >100 |
| 16-3 | 100 ± 1.3 | 89.4 ± 2.7 | 89.7 ± 3.1 | 81.0 ± 3.1 | 81.0 ± 2.2 | 66.0 ± 0.1 | >100 |
| 16-4 | 100 ± 3.6 | 95.0 ± 2.9 | 91.2 ± 1.9 | 91.3 ± 1.2 | 85.4 ± 0.2 | 75.5 ± 1.7 | >100 |
| 16-5 | 100 ± 1.3 | 88.1 ± 1.9 | 85.4 ± 6.4 | 90.9 ± 1.2 | 88.5 ± 2.8 | 79.6 ± 2.7 | >100 |
| 16-6 | 100 ± 3.6 | 91.6 ± 2.6 | 94.3 ± 2.6 | 85.8 ± 2.7 | 83.5 ± 1.1 | 84.9 ± 2.0 | >100 |
| 18-1 | 100 ± 0.5 | 95.4 ± 0.6 | 94.9 ± 1.2 | 92.9 ± 0.6 | 91.0 ± 0.9 | 55.0 ± 1.1 | >100 |
| 18-2 | 100 ± 0.6 | 97.0 ± 3.5 | 99.4 ± 3.9 | 99.1 ± 1.4 | 90.8 ± 2.2 | 63.6 ± 0.8 | >100 |
| 18-3 | 100 ± 1.5 | 88.8 ± 7.0 | 93.1 ± 1.0 | 97.6 ± 1.3 | 87.7 ± 2.0 | 84.3 ± 1.5 | >100 |
| 18-4 | 100 ± 0.5 | 99.5 ± 2.1 | 100.9 ± 1.9 | 96.7 ± 1.7 | 96.1 ± 1.4 | 70.6 ± 0.8 | >100 |
| 18-6 | 100 ± 0.6 | 99.6 ± 0.5 | 96.8 ± 1.9 | 91.6 ± 2.6 | 86.4 ± 1.7 | 80.7 ± 2.5 | >100 |
| 18-13 | 100 ± 1.5 | 99.9 ± 1.3 | 96.8 ± 1.8 | 91.7 ± 3.6 | 79.0 ± 0.8 | 60.6 ± 0.5 | >100 |
| 20-1 | 100 ± 7.0 | 97.5 ± 1.6 | 95.1 ± 5.3 | 93.7 ± 1.2 | 80.9 ± 12.8 | 89.6 ± 1.0 | >100 |
| 20-2 | 100 ± 0.7 | 87.4 ± 1.3 | 84.4 ± 2.3 | 84.6 ± 2.0 | 80.7 ± 0.8 | 74.4 ± 3.8 | >100 |
| 20-3 | 100 ± 1.5 | 86.3 ± 0.4 | 86.3 ± 0.9 | 80.9 ± 2.1 | 82.2 ± 0.5 | 72.5 ± 1.9 | >100 |
| 20-4 | 100 ± 1.5 | 86.1 ± 3.1 | 82.7 ± 1.0 | 83.4 ± 1.3 | 83.0 ± 0.5 | 79.2 ± 1.3 | >100 |
| 20-5 | 100 ± 0.7 | 85.4 ± 4.4 | 84.2 ± 4.1 | 81.2 ± 0.7 | 79.9 ± 0.8 | 77.9 ± 0.8 | >100 |
| 22-1 | 100 ± 3.3 | 97.6 ± 5.0 | 94.8 ± 3.8 | 95.7 ± 2.4 | 94.4 ± 0.4 | 94.4 ± 2.5 | >100 |
| 22-2 | 100 ± 3.9 | 96.6 ± 1.6 | 94.5 ± 6.3 | 96.1 ± 3.8 | 90.5 ± 1.7 | 60.9 ± 1.7 | >100 |

TABLE 11-continued

| | Cell viability (% of control) | | | | | | |
|---|---|---|---|---|---|---|---|
| | U937 (48 h) Compound Concentration (μM) | | | | | | |
| Compounds | 0 | 0.01 | 0.1 | 1 | 10 | 100 | IC$_{50}$ (μM) |
| 22-3 | 100 ± 3.4 | 96.9 ± 1.5 | 93.0 ± 1.5 | 87.5 ± 2.2 | 75.5 ± 1.9 | 53.3 ± 1.5 | >100 |
| 22-4 | 100 ± 7.0 | 95.2 ± 4.6 | 93.3 ± 0.8 | 80.2 ± 11.7 | 84.7 ± 1.7 | 70.6 ± 0.4 | >100 |
| 22-5 | 100 ± 3.4 | 101.8 ± 5.4 | 93.4 ± 1.2 | 92.6 ± 0.9 | 85.1 ± 3.1 | 62.5 ± 2.0 | >100 |

To confirm that the inhibitory activity of pyridinol derivative compounds against intestinal epithelial cells-monocyte adhesion was not due to the toxic effect on the cells, cytotoxicity of the compounds affecting the survival rates of the intestinal epithelial cells (HT-29) and the monocytes (U937) was examined, and the results are shown in Table 10 and Table 11. In the test for inhibitory activity against intestine epithelial cells-monocyte adhesion, the time for culturing with a pyridinol derivative compound was four hours, but to confirm the absence or presence of cytotoxicity of the compound, cytotoxicity was measured when each compound was cultured for 48 hours. As a result, regarding the cytotoxicity IC50 for HT-29, the cytotoxicity IC50 of Compounds 16-1, 16-4, 18-13 and 22-1 were 64.6 M, 34.7 μM, 19.1 μM and 50.1 μM, respectively, and the cytotoxicity IC50 of other compounds were all 100 μM or more, which were 19- to 100-fold higher than the intestine epithelial cells-monocyte adhesion inhibitory activity concentration, that is, 1 M. For U937, the cytotoxicity IC50 of Compound 16-1 was 15.4 μM, and the cytotoxicity IC50 of the other compounds were 100 μM or more. From the above-mentioned IC50 measurement results, it was confirmed that the pyridinol compounds are very safe compounds that have no cytotoxicity in the effective concentration range of an intestine epithelial cells-monocyte adhesion inhibitory activity.

INDUSTRIAL APPLICABILITY

Since a pyridinol derivative or a pharmaceutically acceptable salt thereof according to the present invention inhibits colitis in an IBD model, it can be effectively used as a drug for preventing or treating IBD.

What is claimed is:

1. A compound represented by Formula 1 or pharmaceutically acceptable salt thereof:

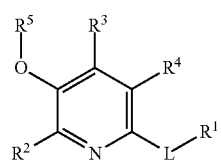

[Formula 1]

wherein R$^2$, R$^3$ and R$^4$ are each independently alkyl having 1 to 8 carbon atoms,
R$^5$ is any one selected from the group consisting of hydrogen; alkyl having 1 to 8 carbon atoms which is substituted by a phenyl; —Si(R$^6$)$_3$,
R$^6$ is any one selected from the group consisting of alkyl having 1 to 8 carbon atoms and phenyl,
R$^1$ is any one selected from the group consisting of hydrogen; sulfonyl which is substituted by a phenyl; carbonyl which is substituted by a phenyl; alkyl having 1 to 12 carbon atoms; phenyl; and naphthyl,
the alkyl having 1 to 12 carbon atoms of R$^1$ is substituted or not substituted with one or more selected from the group consisting of halogen; alkoxy having 1 to 4 carbon atoms; and phenyl which is substituted or not substituted with alkyl having 1 to 4 carbon atoms or halogen,
the phenyl or naphthyl of R$^1$ is each independently substituted or not substituted with one or more selected from the group consisting of halogen; —NO$_2$; alkyl having 1 to 4 carbon atoms, which is substituted or not substituted with halogen; alkoxy having 1 to 4 carbon atoms, which is substituted or not substituted with halogen,
L is a linker represented by Formula 2 below,

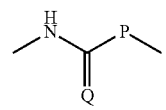

[Formula 2]

wherein Q is O or S, and P is —NH— or —O—.

2. The compound according to claim 1, wherein R$^2$, R$^3$ and R$^4$ are each independently alkyl having 1 to 4 carbon atoms,
R$^5$ is any one selected from the group consisting of hydrogen; alkyl having 1 to 4 carbon atoms, which is substituted or not substituted with phenyl; and —Si(R$^6$)$_3$,
R$^6$ is alkyl having 1 to 6 carbon atoms or phenyl, and
L is —NH—C(O)—NH—, —NH—C(S)—NH—, or —NH—C(O)—.

3. The compound according to claim 1, wherein R$^2$, R$^3$ and R$^4$ are each independently methyl,
R$^5$ is any one selected from the group consisting of hydrogen; methyl substituted or not substituted with phenyl; and —Si(R$^6$)$_3$, and
R$^6$ is butyl or phenyl.

4. The compound of claim 1, wherein R$^1$ is any one selected from the group consisting of hydrogen; sulfonyl, which is substituted with phenyl; carbonyl, which is substituted with phenyl; alkyl having 1 to 10 carbon atoms; phenyl; and naphthyl,
the alkyl having 1 to 10 carbon atoms is substituted or not substituted with one or more substituents selected from the group consisting of halogen; alkoxy having 1 to 4 carbon atoms; and phenyl, which is substituted or not substituted with alkyl having 1 to 4 carbon atoms or halogen, and
the phenyl or naphthyl is each independently substituted or not substituted with one or more substituents selected from the group consisting of halogen; —NO$_2$; alkyl having 1 to 4 carbon atoms, which is substituted or not substituted with halogen; and alkoxy having 1 to 4 carbon atoms, which is substituted or not substituted with halogen.

5. The compound according to claim 1, wherein R$^1$ is any one selected from the group consisting of hydrogen; sulfonyl, which is substituted with phenyl; carbonyl, which is substituted with phenyl; alkyl having 1 to 8 carbon atoms; phenyl; and naphthyl, the alkyl having 1 to 8 carbon atoms is substituted or not substituted with one or more substituents selected from the group consisting of halogen; methoxy; ethoxy; propoxy; and phenyl substituted or not substituted with alkyl having 1 to 4 carbon atoms or halogen, and the phenyl or naphthyl is each independently substituted or not substituted with one or more substituents selected from the group consisting of halogen; —NO$_2$; alkyl having 1 to 4 carbon atoms, which is substituted or not substituted with halogen; and alkoxy having 1 to 4 carbon atoms, which is substituted or not substituted with halogen.

6. The compound according to claim 1, wherein R$^2$, R$^3$ and R$^4$ are each independently methyl, R$^5$ is hydrogen; methyl substituted or not substituted with phenyl; or a silyl substituted with phenyl and butyl, and R$^1$ is hydrogen; carbonyl substituted with phenyl; sulfonyl substituted with phenyl; alkyl having 1 to 8 carbon atoms, which is substituted or not substituted with one or more substituents selected from the group consisting of chloro, methoxy, phenyl, chlorophenyl and butylphenyl; phenyl or naphthyl substituted or not substituted with one or more substituents selected from the group consisting of chloro, fluoro, bromo, methyl, ethyl, propyl, butyl, trifluoromethyl, nitro, methoxy and trifluoromethoxy.

7. The compound according to claim 1, wherein the compound represented by Formula 1 is any one selected from the group consisting of compounds represented by the following formulas:

[Formula 16-6]

[Formula 15-7]

[Formula 16-7]

[Formula 15-8]

[Formula 16-8]

[Formula 15-9]

[Formula 16-9]

[Formula 15-10]

[Formula 16-10]

[Formula 15-11]

[Formula 16-11]

[Formula 15-12]

[Formula 16-12]

[Formula 15-13]

[Formula 16-13]

[Formula 15-14]

[Formula 16-14]

[Formula 15-15]

[Formula 16-15]

[Formula 15-16]

[Formula 16-16]

[Formula 17-1a]

[Formula 18-1]

[Formula 17-2a]

[Formula 18-2]

[Formula 17-3a]

[Formula 18-3]

[Formula 17-4a]

[Formula 18-4]

[Formula 17-5c]

[Formula 18-5]

[Formula 17-6a]

[Formula 18-6]

[Formula 17-7c]

[Formula 18-7]
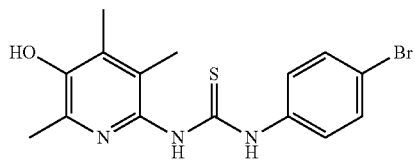
[Formula 17-8a]
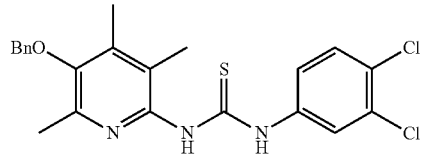
[Formula 17-8b]
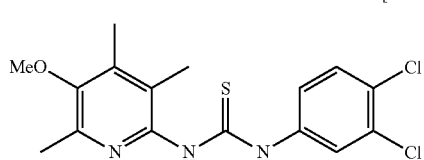
[Formula 17-8c]
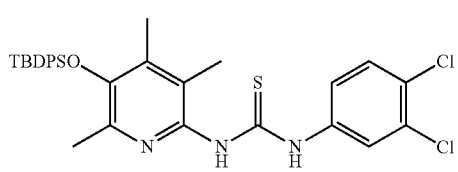
[Formula 18-8]
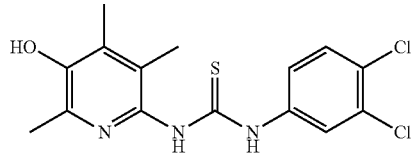
[Formula 17-9a]
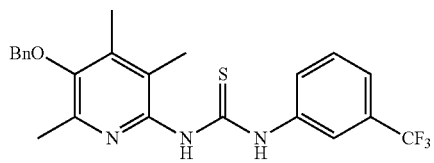
[Formula 17-9b]
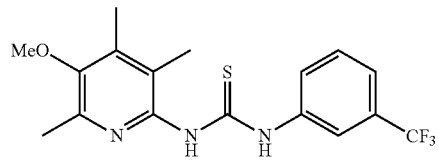
[Formula 17-9c]
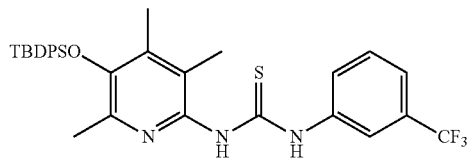
[Formula 18-9]
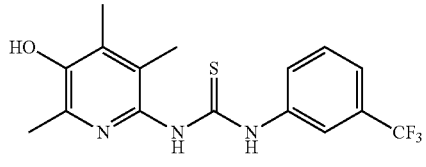
[Formula 17-10c]
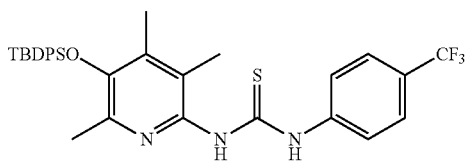
[Formula 18-10]
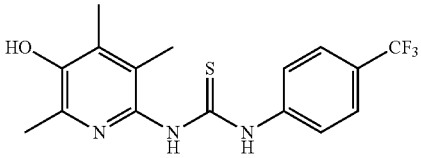
[Formula 17-11c]
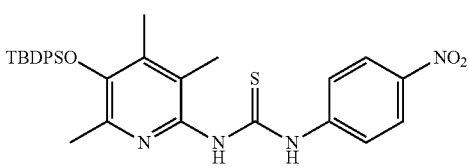
[Formula 18-11]
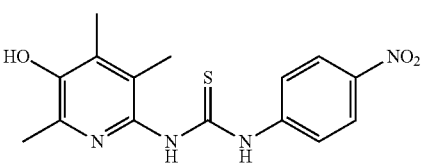
[Formula 17-12c]
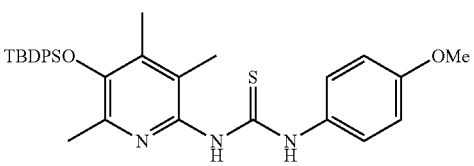
[Formula 18-12]
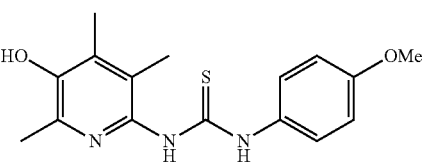
[Formula 17-13a]
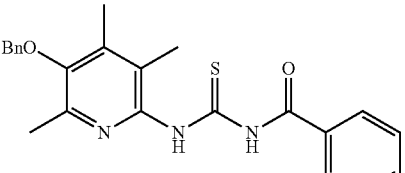
[Formula 18-13]
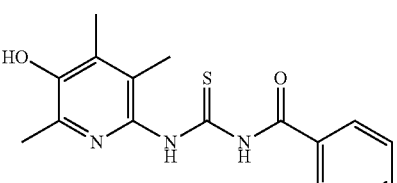

-continued

[Formula 19-1]

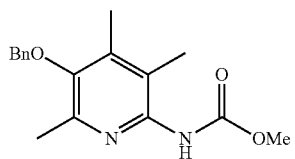

[Formula 20-1]

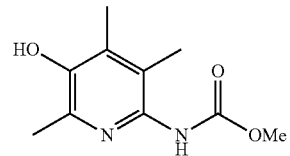

[Formula 19-2]

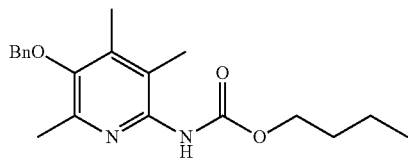

[Formula 20-2]

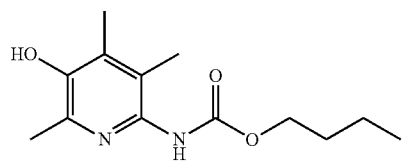

[Formula 19-3]

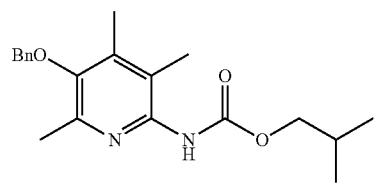

[Formula 20-3]

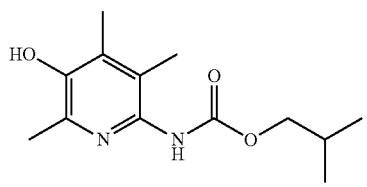

[Formula 19-4]

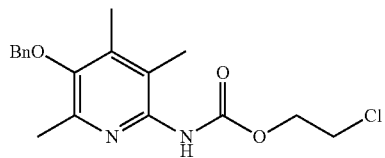

[Formula 20-4]

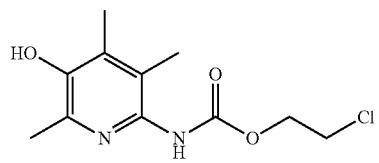

-continued

[Formula 19-5]

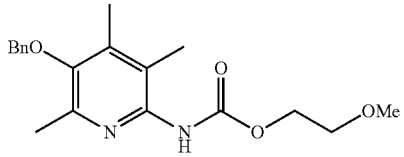

[Formula 20-5]

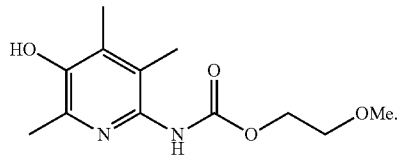

8. The compound according to claim 1, wherein the pharmaceutically acceptable salt is the form of an acid addition salt formed by an organic acid selected from the group consisting of oxalic acid, maleic acid, fumaric acid, malic acid, tartaric acid, citric acid and benzoic acid, or an inorganic acid selected from the group consisting of hydrochloric acid, sulfuric acid, phosphoric acid and hydrobromic acid.

9. A method for preparing a compound of Formula 1 below, comprising:
reacting a compound of Formula 4 below with a compound of Formula 5 or 6 below:

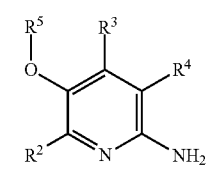
[Formula 4]

[Formula 5]

[Formula 6]

[Formula 1]

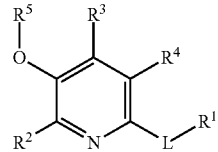

in Formulas 1 and 4 to 9,
$R^1$ to $R^5$, and Q and L are as defined in claim 1, and R is carbonyl or sulfonyl, and X is halogen.

10. A pharmaceutical composition for treating an inflammatory bowel disease, comprising:
the compound or pharmaceutically acceptable salt thereof according to claim 1.

* * * * *